US005565584A

United States Patent [19]
Tegeler et al.

[11] Patent Number: 5,565,584
[45] Date of Patent: Oct. 15, 1996

[54] 1-ALKYL-, 1-ALKENYL-, AND 1-ALKYLNLARYL-2-AMINO-1,3-PROPANEDIOLS AND RELATED COMPOUNDS

[75] Inventors: John J. Tegeler, Bridgewater; Barbara S. Rauckman, Flemington; Russell R. L. Hamer, Lebanon; Brian S. Freed, Phillipsburg, all of N.J.; Gregory H. Merriman, Fairfield, Ohio

[73] Assignee: Hoechst-Roussel Pharmaceuticals, Inc., Somerville, N.J.

[21] Appl. No.: 425,531

[22] Filed: Apr. 20, 1995

Related U.S. Application Data

[60] Division of Ser. No. 942,908, Sep. 10, 1992, Pat. No. 5,360,811, which is a continuation-in-part of Ser. No. 840,236, Feb. 24, 1992, abandoned, which is a continuation of Ser. No. 632,910, Dec. 24, 1990, abandoned, which is a continuation-in-part of Ser. No. 596,448, Oct. 12, 1990, abandoned, which is a continuation-in-part of Ser. No. 492,200, Mar. 13, 1990, abandoned.

[51] Int. Cl.$^6$ ................................................. C07D 303/36
[52] U.S. Cl. ....................... 549/551; 546/281.7; 548/214; 548/247; 549/60
[58] Field of Search ........................... 546/268; 548/214, 548/247; 549/60, 551

[56] References Cited

U.S. PATENT DOCUMENTS

| | | | |
|---|---|---|---|
| 2,723,270 | 11/1955 | Scudi | 546/331 |
| 3,094,553 | 6/1973 | Hellman et al. | 546/335 |
| 3,539,589 | 11/1970 | Teotino et al. | 548/561 |
| 3,558,652 | 1/1971 | Teotino et al. | 548/561 |
| 3,871,958 | 3/1975 | Nakazawa et al. | 435/106 |
| 3,992,420 | 11/1976 | Lind et al. | 549/555 |
| 4,609,668 | 9/1986 | Schaub et al. | 514/383 |
| 4,732,901 | 3/1988 | Buckle | 514/277 |
| 4,935,101 | 6/1990 | Shum et al. | 203/48 |

FOREIGN PATENT DOCUMENTS

| | | |
|---|---|---|
| 0079390 | 5/1975 | European Pat. Off. . |
| 0185814 | 7/1986 | European Pat. Off. . |
| 2195634 | 4/1988 | United Kingdom . |
| 8808169 | 3/1988 | WIPO . |

OTHER PUBLICATIONS

A. Hajos, Acta Chimica Academiae Scientarum Hungaricae, 84, 471 (1975) published in Hungary & entitled "Synthesis of threo–and erythro–β–o–tolylserine and their derivatives".

S. Van Der Meer, et al., Recueil, 72, 236 (1953) published in the Netherlands and entitled "Chloramphenicol Analogues I".

J. Morris & D. G. Wishka, Tetrahedron Letters, 29, 143 (1988) published in Great Britain and entitled "Synthesis of Novel Antagonists of Leukotriene B$_4$".

K. Sonogashira, et al. Tetrahedron Letters, 50, 4467 (1975) published in Great Britain and entitled "A Convenient Synthesis of Acetylenes: Catalytic Substitutions of Acetylenic Hydrogen wth Bromoalkenes, Iodoarenes, and Bromopyrdines".

J. E. Parks, et al., Inorganic Chemistry, 10, 2472 (1971) published in the United States of America and entitled "Three–Dimensional Macrocyclic Encapsulation reactions, II. Synthesis and Properties of Nonoetahedral Clathro Chelates Derived from Tris(2–aldoximo–6–pyridyl) phosphine and Boron Trifluoride or Tetrafluoroborate".

E. L., Smith and J. J. Tegeler, Annual Reports in Medicinal Chemistry, 24, 13 (1989) published in the United States of America and entitled "Chapter 19, Advances in Dermatology".

A. K. Gupta, et al., The Journal of Investigation Dermatology, 91, 486 (1988) published in the United States of America and entitled "Sphingosine Inhibits Phorbol Ester–Induced Inflammation, Ornithine Decarboxylase Activity, and Activation of Protein Kinase C in Mouse Skin".

Ng, Ph. Buu Hoi, et al., Chemical Abstracts, 45, 9005i (1951) published in the United States of America and entitled "Three new analogs of chloramphenicol".

H. M. Crooks, Jr., et al., Chemical Abstracts, 46, 9602c (1952) published in the United States of America and entitled "Diarylphenylpropaneaminodiols".

Parke, Davis & Co., Chemical Abstracts, 48, 8823g (1954) published in the United States of America and entitled "Organic amino diols".

Parke, Davs & Co., Chemical Abstracts, 47, 3347d (1952) published in the United States of America and entitled "Amino diols".

H. M. Crooks, Jr., et al., Chemical Abstracts, 45, 633a (1951) published in the United States of America and entitled "(Nitrophenyl)acylamioalkane diols".

L. M. Long and N. D. Jenesel, Chemical Abstracts, 45, 9564b (1951) published in the United States of America and entitled "Furan compounds".

E. C. Hermann, Chemical Abstracts, 50, 5760c (1956) published in the United States of America and entitled "Thienyl amido–1,3–propanediols".

Duke Univ., Derwent 88–091694113 published May. 25, 1988 in Great Britain and entitled "Inhibition of protein kinase C with amphiphatic long–chain base–esp. with sphingosine, for treating asthma, inflammation, psoriasis or tumour metastasis".

M. Miyoshi, et al., Chemical Abstracts, 92, 198778a (1980) published in the United States of America and entitled "β–Hydroxyamino acids".

F. A. Arena, et al., Chemical Abstracts, 89, 59826q (1978) published in the United States of America and entitled "Structure–activity relations in acetylcholinesterase reactivators inhibited by phosphoric esters. XII. Hydroxyiminomethyalkylpiridine methiodides".

(List continued on next page.)

*Primary Examiner*—Ceila Chang
*Attorney, Agent, or Firm*—Raymond R. Wittekind

[57] ABSTRACT

Novel 1-alkyl-, 1-alkenyl-, and 1-alkynylaryl-2-amino-1,3-propanediols, intermediates and processes for the preparation thereof, and methods of reducing inflammation and cell proliferation, and relieving memory dysfunction, and inhibiting bacterial and fungal growth are disclosed.

5 Claims, No Drawings

OTHER PUBLICATIONS

S. Nimkar, et al., Tetrahedron Letters, 29, 3037 (1988) published in Great Britain and entitled "A Stereoselective Synthesis of Sphingosine, A Protein Kinase C Inhibitor".

Y. Gao, et al., Journal of the American Chemical Society, 109, 5765 (1987) published in the United States of America and entitled "Catalytic Asymmetric Epoxidation and Kinetic Resolution: Modified Procedures Including in Situ Derivatization".

S. Knapp, et al., Journal of Organic Chemistry, 55, 5700 (1990) published in the United States of America entitled "Amino Alcohol and Amino Sugar Synthesis by Benzoylcarbamate Cyclization".

P. Garner & J. M. Park, Journal of Organic Chemistry, 52, 2361 (1987) published in the United States of America & entitled "The Synthesis and Configurational Stability of Differentially Protected β-Hydroxy-α-amino Aldehydes".

D. P. Schumacher, et al., Journal of Organic Chemistry, 55, 5291 (1990) published in the United States of America & entitled "An Efficient Synthesis of Florfenicol".

D. A. Evans & A. E. Weber, Journal of the Am. Chem. Soc., 109, 7151 (1987) published in the United States of America & entitled "Synthesis of the Cyclic Hexapeptide Echinocandin D. New Approaches to the Asymmetric Synthesis of β-Hydroxy α-Amino Acids".

Y. Nishizuka, Nature, 308, 693 (1984) published in Great Britain & entitled "The role of protein kinase C in cell surface signal transduction and tumour promotion".

L. Hegemann, et al., Archives of Dermatological Rsearch, 281, 561 (1990) published in Germany & entitled "Inhibitors of proteinkinase C express antiproliferative properties in keratinocytes in vitro".

L. Hegemann and G. Mahrle in "Pharmacology of the Skin", H. Muktar, Ed; CRC Press, Ann Arbor, Michigan, pp. 357 to 368, 1992.

J. J. Tegeler, et al., Chemical Abstracts, published in the United States of America and entitled "Preparation of Heteroarylaminoalkanols".

1-ALKYL-, 1-ALKENYL-, AND 1-ALKYLNLARYL-2-AMINO-1,3-PROPANEDIOLS AND RELATED COMPOUNDS

This is a division of prior application Ser. No. 07/942,908 filed Sep. 10, 1992, now U.S. Pat. No. 5,360,811 which is a continuation-in-part of prior application Ser. No. 07/840,236 filed Feb. 24, 1992, now abandoned, which is a continuation of prior application Ser. No. 07/632,910 filed Dec. 24, 1990, now abandoned, which is a continuation-in-part of prior application Ser. No. 07/596,448 filed Oct. 12, 1990, now abandoned, which is a continuation-in-part of application Ser. No. 07/492,200 filed Mar. 13, 1990, now abandoned.

The present invention relates to 1-alkyl-, 1-alkenyl-, and 1-alkynylaryl-2-amino-1,3-propanediols. More particularly, the present invention relates to 1-alkyl-, 1-alkenyl-, and 1-alkylnylaryl-2-amino-1,3-propanediols of formula 1.

$$RCH(OR^1)CH(NR^2R^3)R^4$$

or $$RCH_2CR^{35}(NR^2R^3)R^4$$

wherein R is

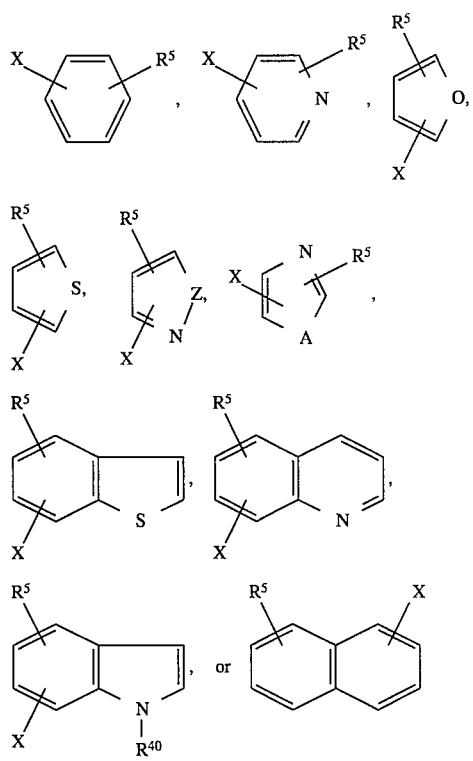

wherein $R^5$ is $CH_3(CH_2)_mC\equiv C$, $CH_3(CH_2)_mCH=CH$, $CH_3(CH_2)_mCH_2CH_2$,

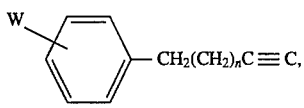

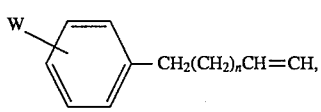

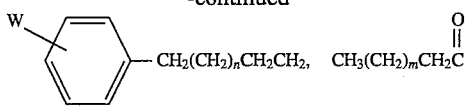

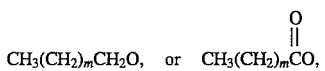

wherein m is 3 to 15, n is 0 to 12, and W and X are independently hydrogen, hydroxy, alkyl, alkoxy, halogen, or trifluoromethyl, or

wherein $R^{23}$ is loweralkyl; Z is S, O, or C=O; and A is S or O; $R^1$ is hydrogen, alkyl, $Si(R^{23})_2C(R^{23})_3$ wherein $R^{23}$ is alkyl,

wherein $R^{24}$ isalkyl or

wherein $R^6$ is hydrogen, alkyl, alkoxy, $N(R^{21})_2$ wherein $R^{21}$ is hydrogen, alkyl, or

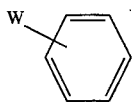

wherein W is as above, or

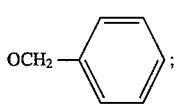

$R^2$ is hydrogen or alkyl; $R^3$ is hydrogen, alkyl or

wherein $R^6$ is as above or $NHR^{27}$ wherein $R^{27}$ is alkyl; $R^{35}$ is

wherein $R^{36}$ is alkyl; $R^4$ is

wherein $R^7$ is hydrogen or alkyl, $C(R^{25})_2OR^8$ wherein $R^8$ is hydrogen, alkyl, or

wherein $R^6$ is as above and $R^{25}$ is hydrogen or alkyl; $R^{40}$ is alkyl or a group of the formula

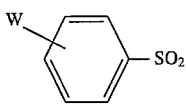

wherein W is as above; $R^1$ and $R^8$ taken together with the oxygen to which they are attached form a group of the formula

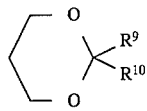

wherein $R^9$ and $R^{10}$ are independently hydrogen or alkyl; $R^2$, $R^3$ and $R^4$ taken together with the nitrogen and oxygen to which they are attached form a group of the formula

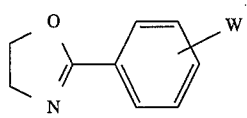

wherein W is as above; $R_3$ and $R_4$ taken together with the nitrogen and oxygen atoms to which they are attached form a group of the formula

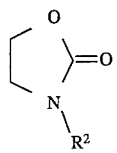

wherein $R^2$ is as above; $R^2$ and $R^3$ taken together with the nitrogen atom to which it is attached form a group of the formula

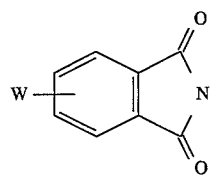

wherein W is as above; $R^3$ and $R^4$ taken together with the nitrogen and oxygen atoms to which they are attached form a group of the formula

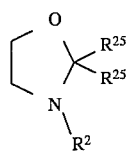

wherein $R^2$ is as above and $R^{25}$ is alkyl; $R^1$, $R^2$ and $R^3$ taken together with the nitrogen and oxygen atoms to which they are attached form a group of the formula

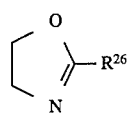

wherein $R^{26}$ is alkyl; the optical isomers thereof, or the pharmaceutically acceptable salts thereof, which are useful for reducing inflammation by virtue of their ability to inhibit protein kinase C and thus indicated for the treatment of psoriasis and other skin disorders, for inhibiting tumor or neoplastic cell growth by virtue of their ability to reduce cell proliferation and thus indicated in cancer therapy, and relieving memory dysfunction and thus indicated in the treatment of Alzheimer's disease, and as antibacterial and antifungal agents, alone or in combination with adjuvants.

Preferred 2-amino-1,3-propanediols of the present invention are those wherein R is

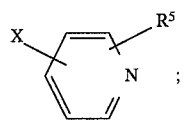

$R^1$, $R^2$, and $R^3$ are hydrogen and $R^5$ is $CH_3(CH_2)_mCH_2CH_2$ or

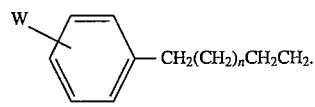

Also preferred are compounds wherein R is

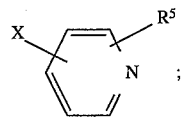

$R^1$ and $R^2$ are hydrogen; $R^4$ is

and $R^5$ is $CH_3(CH_2)_mC\equiv C$.

The present invention also relates to compounds of the formulas wherein R is

RCHO wherein R is

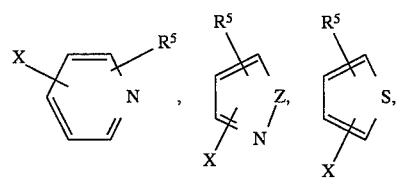

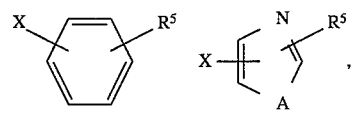

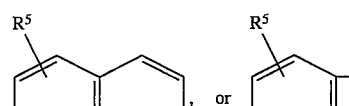

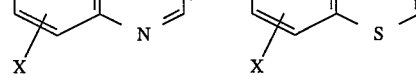

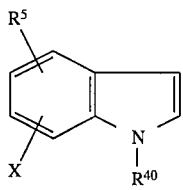

wherein $R^5$ is $CH_3(CH_2)_mC\equiv C$, $CH_3(CH_2)_mCH=CH$, $CH_3(CH_2)_mCH_2CH_2$, or

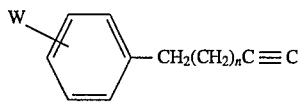

wherein m is 3 to 15, n is 0 to 12, W and X are independently hydrogen, alkyl, alkoxy, halogen, or trifluoromethyl and Z is S or O; A is S or O; $R^{40}$ is alkyl or a group of the formula

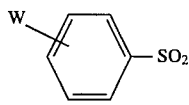

wherein W is as above;

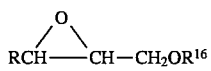

wherein R is

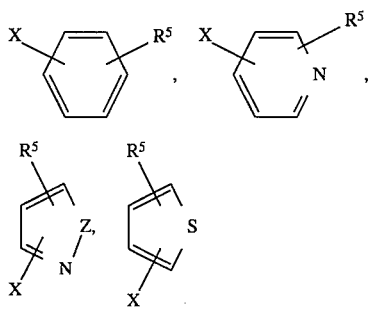

wherein $R^5$ is $CH_3(CH_2)_mC\equiv C$, $CH_3(CH_2)_mCH=CH$, $CH_3(CH_2)_mCH_2CH_2$, or

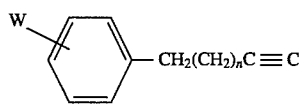

wherein m is 3 to 15, n is 0 to 12, $R^{16}$ is hydrogen or a group of the formula

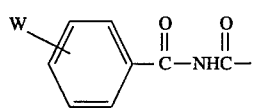

W and X are independently hydrogen, alkyl, alkoxy, halogen, or trifluoromethyl, and Z is O; and wherein R is

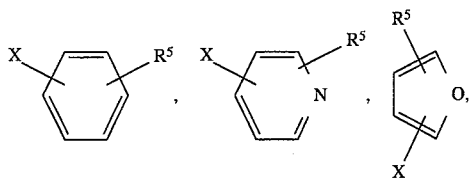

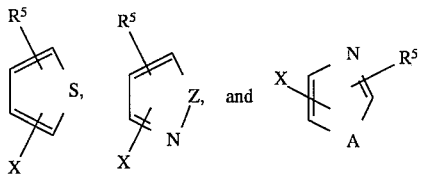

wherein $R^5$ is $CH_3(CH_2)_mC\equiv C$, $CH_3(CH_2)_mCH=CH$, $CH_3(CH_2)_mCH_2CH_2$,

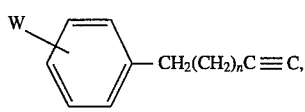

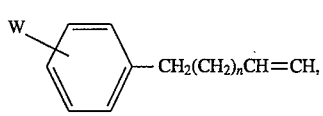

or

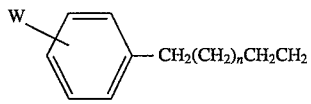

wherein m is 3 to 15, n is 0 to 12, and W and X are independently hydrogen, loweralkyl, loweralkoxy, halogen, or trifluoromethyl, Z is S, O, or C=O; and A is S or O, and $R^4$ is

wherein is $R^7$ is hydrogen or loweralkyl, $C(R^{25})_2OR^8$ wherein $R^8$ is hydrogen, loweralkyl, or

is as above; and

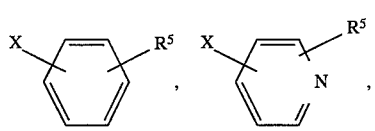

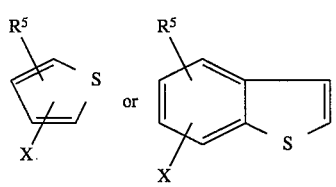

wherein $R^5$ is $CH_3(CH_2)_mC\equiv C$, $CH_3(CH_2)_mCH=CH$, $CH_3(CH_2)_mCH_2CH_2$,

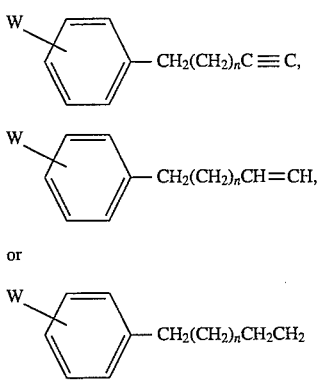

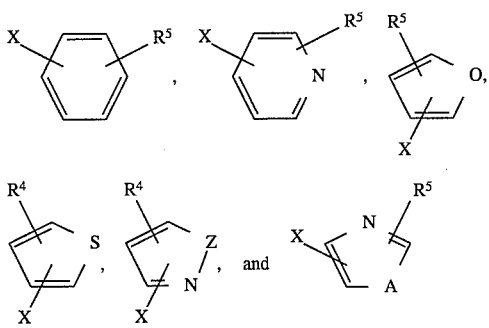

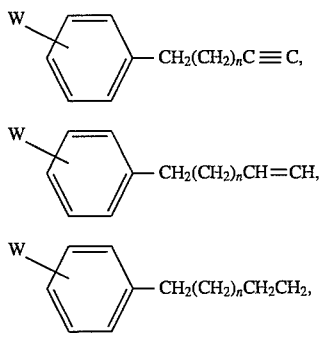

wherein m is 3 to 15, n is 0 to 12, and W and X are independently hydrogen, loweralkyl, loweralkoxy, halogen, or trifluoromethyl which are useful as intermediates for the preparation of the present 2-amino-1,3-propanediols.

Also included as intermediates for the preparation of the present 2-amino-1,3-propanediols are oxazolidinones of the formula wherein R is wherein $R^5$ is $CH_3(CH_2)_mC{\equiv}C$, $CH_3(CH_2)_mCH{=}CH$, $CH_3(CH_2)_mCH_2CH_2$, wherein m is 3 to 25, n is 0 to 12, and W and X are independently hydrogen, alkyl, alkoxy, halogen, or trifluoromethyl, Z is S, O, or C=O; and A is S or O; $R^1$ is hydrogen or

CR⁶ wherein $R^6$ is hydrogen, alkyl, alkoxy, or

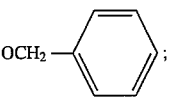

$R^{18}$ is halogen or $N_3$; and $R^{19}$ is a group of the formula

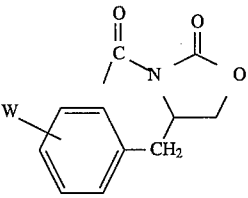

wherein W is hydrogen, loweralkyl, loweralkoxy, halogen, or trifluoromethyl; or a group of the formula

—COR²⁰ wherein $R^{20}$ is loweralkyl.

As used through the specification and appended claims, the term "alkyl" refers to a straight or branched chain hydrocarbon radical containing no unsaturation and having 1 to 10 carbon atoms. Examples of alkyl groups are methyl, ethyl, 1-propyl, 2-propyl, 1-butyl, 1-pentyl, 3-hexyl, 4-heptyl, 2-octyl, 3-nonyl, 4-decyl and the like. The term "alkanol" refers to a compound formed by a combination of an alkyl group and hydroxy radical. Examples of alkanols are methanol, ethanol, 1- and 2-propanol, 2,2-dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like. The term "halogen" refers to a member of the family fluorine, chlorine, bromine, or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, decanoyl and the like. The term "lower" as applied to any of the aforementioned groups refers to a group having a carbon skeleton containing up to and including 8 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diastereomeric salts of those instant compounds characterized by the presence of a basic amino group and an optically active acid, those instant compounds characterized by the presence of a carboxylic acid group and an optically active base, or by synthesis from optically active precursors.

The present invention comprehends all optical isomers and racemic forms thereof and all geometric isomers of the compounds disclosed and claimed herein. The formulas of the compounds shown herein are intended to encompass all possible geometric and optical isomers of the compounds so depicted.

The compounds of the present invention that have adjacent chiral centers exist as diastereomers and are distinguished as the erythro- and threo-isomers. The erythro diastereomers are those that become meso, i.e., optically inactive, by virtue of having an element of symmetry in one of the possible conformations, when one of the dissimilar substituents is replaced by the other. The threo diastereomers are those that remain enantiomeric, i.e., optically active, by virtue of lacking an element of symmetry in one of the possible conformations, when one of the dissimilar substitutents is replaced by the other. For example, replacement of the amino group of an erythro-2-amino-1,3-propanediol 9a of the present invention by a hydroxyl group creates a meso-1,2,3-propanetriol 9b, having a plane of symmetry through the carbon backbone of the molecule, as shown below,

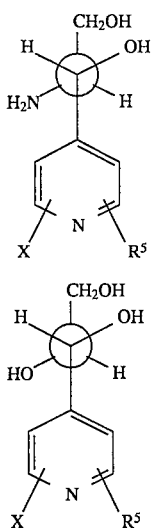

and replacement of the amino group of a threo-2-amino-1,3-propanediol 9c of the present invention by a hydroxy group creates an enantiomer 9d, lacking an element of symmetry in all conformations, one of which is 9d.

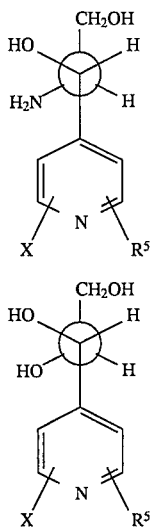

The chirality of the enantiomeric compounds of the present invention, prepared by asymmetric induction, is designated by the symbols "R" and "S" and is determined by application of the sequence-rule of Cahn-Ingold- and Prelog (see R. S. Cahn, C. Ingold, and v. Prelog, Angewandte Chemie, International Edition English, 5, 385 (1966) and 5, 511 (1966). Thus, for example, the handedness of the chiral centers at the 2- and 3-positions of the 2-amino-1,3-propanediol 9e

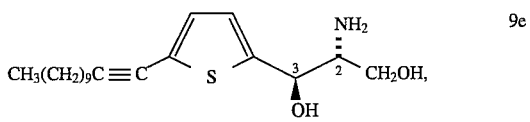

prepared from (4S)-3-(bromoacetyl)-4-(phenylmethyl)-2-oxazolidinone, is designated 2R (right) and 3S (left). The centers of the enantiomeric 2-amino-1,3-propanediol 9f,

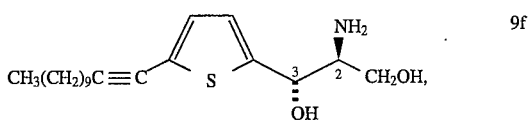

prepared from the enantiomeric (4R)-3-(bromoacetyl)-4-(phenylmethyl)-2-oxazolidinone, is designated 2S and 3R.

The novel 1-alkyl-, 1-alkenyl-, and 1-alkynylaryl-2-amino-1,3-propanediols of the present invention are prepared by the processes illustrated in Reaction Schemes A, B, and C for the pyridine series, D to L for the thiophene series, and M and N for the phenyl series, having an aralkyl side-chain. The transformations shown therein are applicable to the preparation of compounds of the invention wherein the aryl group is, among others, substituted and unsubstituted phenyl, furyl, thienyl, isoxazolyl, isothiazolyl, and pyrrolyl, thiazolyl, and oxazolyl, having a 1-alkyl, 1-alkenyl, or 1-alkynyl-side chain.

To prepare a 1-alkynylpyridinyl-2-amino-1,3-propanediol 7 wherein W and X are hydrogen, alkyl, alkoxy, halogen, or trifluoromethyl, a pyridinylcarboxaldehyde 2 wherein W and X are as above and Y is halogen is condensed with an amidomalonic acid ester 3 wherein $R^{11}$ and $R^{12}$ are alkyl to provide an alkyl pyridinylpropionate 4 wherein $R^{11}$, $R^{12}$, X, and Y are as above, which is alkynylated to alkynylpyridine 5 wherein $R^{11}$, $R^{12}$, W and X are as above and n is 3 to 15 and, in turn, reduced to pyridinyl-1,3-propanediol 6 wherein $R^{12}$, W, and X are as above and hydrolyzed to 7.

The condensation of carboxaldehyde 2 and malonate 3 is conducted in an ethereal solvent in the presence of a tertiary amine. Among ethereal solvents there may be mentioned diethyl ether, methyl tert-butyl ether, 1,2-dimethyoxyethane, 2-methoxyethyl ether, dioxane, and tetrahydrofuran. Among tertiary amines there may be mentioned pyridines (pyridine, picoline, lutidine, and collidine) and trialkylamines (trimethylamine, triethylamine, and tripropylamine). Tetrahydrofuran and triethylamine are the preferred solvent and tertiary amine, respectively. While the condensation temperature is not critical, the reaction is preferably performed at about ambient temperature (25° C.), although reduced temperatures (about 0° C. to about 25° C.) or elevated temperatures (about 25° C. to the boiling point of the reaction mixture) may be employed.

The alkynylation is performed by treating a halopyridine 4 with an alkyne 13

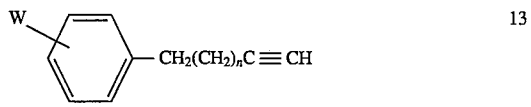

wherein W and n are as above in an acid acceptor, e.g., a di- or trialkylamine, such as, diethylamine, dipropylamine, trimethylamine, triethylamine, or tripropylamine, in the presence of bis(triphenylphosphine)palladium dichloride cuprous iodide at a temperature of about 0° to about 75° C. Triethylamine is the preferred acceptor. A temperature of about 50° to 60° C. is the preferred alkynylation temperature. An ethereal solvent may be employed. Ethereal solvents include diethyl ether, methyl tert-butyl ether, 1,2-dimethoxyethane, 2-methoxyethyl-ether, dioxane, and tetrahydrofuran. Tetrahydrofuran is the preferred solvent.

The reduction of an alkyl pyridinylpropionate 5 to a propanediol 6 is accomplished by means of an alkali borohydride in an ethereal solvent at a reduction temperature within the range of about 0° to about 50° C. Included among alkali borohydrides are calcium borohydride, lithium borohydride, potassium borohydride, and sodium borohydride. Included among ethereal solvents are diethyl ether, methyl tert-butyl ether, 1,2-dimethoxyethane, 2-methoxyethyl ether, dioxane, and tetrahydrofuran. A reducing system of lithium borohydride or calcium borohydride in tetrahydrofuran at a temperature of from about 0° to 25° C. is preferred.

The hydrolysis of a carboxamide 6 to an aminodiol 7 may be carded out by conventional hydrolysis techniques. For example, carboxamide 6 may be hydrolyzed by an alkali metal hydroxide, i.e., lithium hydroxide, sodium hydroxide, or potassium hydroxide, in an aqueous alkanol, i.e., methanol, ethanol, or 1- or 2-propanol, at a hydrolysis temperature of about 0° C. to about 100° C.

To prepare a 1-alkylpyridinyl-2-amino-1,3-propanediol 9 wherein W, X, and m are as hereinbeforedescribed, a 1-alkynylpyridinyl-2-amido-1,3-propanediol 6 is hydrogenated to a 1-alkylpyridinyl-2-amido-1,3-propanediol 8, which is converted to a 1-alkylpyridinyl-2-amino-1,3-propanediol 9.

The hydrogenation is effected by treating an alkyne 6 with hydrogen at about atmospheric pressure to about 60 psi, a pressure of about 40 psi being preferred, in the presence of a metal catalyst, e.g., platinum, palladium, rhodium, or ruthenium, unsupported or supported on carbon or calcium carbonate, palladium-on-carbon being preferred, in an alkanol, e.g., methanol, ethanol, or 1- or 2-propanol, ethanol being preferred, at a hydrogenation temperature of about 25° to about 50° C., a temperature of about 25° C. being preferred.

The conversion of pyridinylamidodiol 8 to pyridinylaminodiol 9, i.e., the hydrazinolysis of 8, is conducted with hydrazine, free or in its hydrated form, in an alkanol such as, for example, methanol, ethanol, or 1- or 2-propanol, at a temperature of from about 25° C. to the reflux temperature of the reaction mixture. Ethanol is the preferred solvent. A hydrazinolysis temperature of about the reflux temperature of the reaction mixture is also preferred.

Alternatively, entry into the 1-alkynyl- and 1-alkylpyridinyl-2-amino-1,3-propanediol systems, i.e., systems of formulas 7 and 9, respectively, wherein W, X, and m are as hereinbeforedescibed may be achieved by alkynylation of pyridinylcarboxaldehyde 2 wherein W, X, and Y are as above to alkynylpyridinylcarboxaldehyde 10 wherein W, X, and m are as above followed by conversion of pyridinylcarboxaldehyde 10 to alkyl pyridinylpropionate 5 wherein $R^{11}$, $R^{12}$, W, X, and m are as above and hydrogenation of an alkynylpyridine 5 wherein $R^{11}$, $R^{12}$, W, X, and m are as above to 11 wherein $R^{11}$, $R^{12}$, W, X, and m are as above. The alkynylation, conversion, and hydrogenation, i.e., the transformations of 2 to 5 and 11, via 10, are accomplished by processes substantially similar to the corresponding transformations of 4 to 5, 2 to 4, and 6 to 8.

Alkyl 1-alkylpyridinylpropionate 11 wherein $R^{11}$, $R^{12}$, W, X, and m are as above may be reduced to 1-alkyl pyridinylpropanediol 8 by the process essentially the same as that employed for the reduction of alkyl pyridinylpropionate 5 to propanediol 6.

Entry into the 1-alkynylpyridinyl-2-amino-1,3-propanediol series, i.e., the series encompassing compounds of formulas 5, 6, and 7, is also attained by reducing an alkyl pyridinylpropionate 4 wherein $R^{11}$, $R^{12}$, W, X and Y are as hereinbeforedescribed to a pyridinylpropanediol 12 and alkynylating a pyridinyldiol 12, so obtained, to alkynylpyridinyldiol 6. As described above, amidopropanediol 6 is convened to amino propanediol 7 by hydrolysis. Similarly, the reduction of 4 to 12 and the alkynylation of 12 to 6 are performed by processes substantially the same as those utilized for the conversion of 5 to 6 and 4 to 5.

Derivatives of an alkynylpyridinyl-2-amino-1,3-diol 7 are prepared from amidopropanediol 6 by acylation of 6 wherein $R^{12}$, W, X, and m are as hereinbeforedescribed to an amidodiacyloxypropane 15 wherein $R^{12}$, $R^{13}$, $R^{14}$, W, and m are as hereinbeforedescribed with, for example, an alkanoic acid anhydride such as acetic anhydride in the presence of triethylamine and 4-dimethylaminopyridine to 15, and dioxanylation of 6 to amidodioxane 14 wherein $R^{12}$, $R^{15}$, $R^{16}$, W, X, and m are as hereinbeforedescribed with, for example, 2,2-dimethoxypropane in the presence of para-toluene sulfuric acid. Hydrolysis of 15 as described for the conversion of 6 to 7 provides aminopropanediol 7. An amidodiacyloxypropane 15 is selectively hydrolyzed to an amidodihydroxy propane 20 by, for example, an alkali metal carbonate such as lithium, sodium, or potassium carbonate in an alkanol such as methanol, ethanol, or 2-propanol. Potassium carbonate in methanol is the preferred hydrolysis medium. The hydrolysis proceeds readily at ambient temperature. Elevated temperatures to the reflux temperature of the hydrolysis medium may be employed.

Acyl derivatives of amidopropanediol 12 wherein $R^{12}$, X, and Y are as hereinbeforedescribed are prepared by treating 12 with an alkanoic acid anhydride under the conditions for the conversion of 6 to 15.

To prepare a 1-alkenyl-2-amino-1,3-propanediol 17 wherein W, X, and m are as hereinbeforedescribed a 1-alkynyl-2-amino-1,3-propanediol 6 wherein $R^{12}$, W, X, and m are as above is hydrogenated to a 1-alkenyl-2-amino-1,3-propanediol 16 wherein $R^{12}$, W, X, and m are as above and the configuration of the hydrogen atoms of the carbon-to-carbon double bond is cis, which is hydrolyzed to 17 wherein W, X, and m are also as above.

To fabricate an N,O,O-tribenzyloxycarbonyl-2-amino-1,3-propane 18 wherein $R^{15}$ is

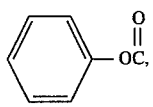

and 2-amino-1,3-propanediol 9 is treated with N-benzyloxycarbonyloxysuccinimide 20

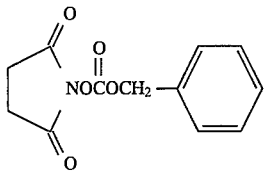

in the presence of a tertiary amine, e.g., triethyl amine in an ethereal solvent, e.g., tetrahydrofuran at about ambient temperature.

To synthesize a 2-amino-1,3-propanediol 19, a 1,3-diacyloxy-2-propanylacetamide 13 is hydrolyzed by hydrazine hydrate in the presence of ethanol according to the procedure for the conversion of 8 or 9.

Generally, the ultimate 1-alkylaryl-2-amino-1,3-propanediols of the present invention are prepared from 1-alkynylarylcarboxaldehydes. See Reaction Scheme A for the conversion of 10 to 9 in the pyridine series. In the isoxazole series, the ultimate 1-alkylisoxazolyl-2-amino-1,3-propanediols may be prepared, for example, from a 5-(1-alkyl)-3-isoxazolecarboxaldehyde 21 wherein $R^5$ is dodecyl.

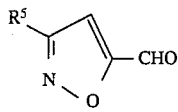
21

A 3-isoxazolecarboxaldehyde 21 wherein $R^5$ is dodecyl, in turn, is synthesized, for example, by condensing 1-nitrotridecane with O-trimethylsilylpropynol in the presence of phenylisocyanate and triethylamine followed tetrabutylammonium fluoride to afford isoxazolemethanol 22

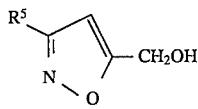
22 wherein $R^5$ is dodecyl, which is oxidized by oxalyl chloride:dimethylsulfoxide to 21.

To prepare a 2-alkoxycarbonylamino-1,3-propanediol, for example, 1-alkynyl-2-t-butyloxycarbonylamino-1,3-propanediol 6 wherein $R^{12}$ is $OC(CH_3)_3$, a 1-alkynyl-2-amino-1,3-propanediol 7 is acylated with di-t-butyldicarbonate in the presence of a base such as sodium bicarbonate in a halocarbon solvent such as chloroform at an elevated temperature of about 60° C.

To prepare a 2-dialkylamino-1,3-propanediol, for example, a 1-alkenyl-2-dimethylamino-1,3-propanediol 23, a 1-alkenyl-2-amino-1,3-propanediol 17 is reductively alkylated with formaldehyde such as formalin in the presence of a reducing agent such as sodium cyanoborohydride in a solvent such as acetonitrile at ambient temperature.

Additional N-substituted 2-amino-1,3-propanediols of the present invention are prepared by acylation of an aminodiol, for example, a thienylaminodiol 30. Thus, treatment of amino 30 with an isocyanate 34

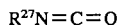
34 wherein $R^{27}$ is as hereinbeforedescribed affords a urea 31 wherein $R^5$, $R^{27}$, and X are as hereinbeforedescribed, with an acyl halide 35

35 wherein $R^6$ is as hereinbeforedescribed affords an amide 32 wherein $R^6$ is as hereinbeforedescribed and Hal is chloro or bromo, and with haloformate 36

36 wherein $R^{28}$ and Hal are as hereinbeforedescribed affords a urethane 33. More specifically, treatment of amine 30 with an isocyanate 34 in a dipolar aprotic solvent (e.g., dimethylacetamide, dimethylformamide, hexamethylphosphoramide, or dimethylsulfoxide) in the presence of an acid acceptor (e.g., pyridine, 4-dimethylaminopyridine, triethylamine, or tripropylamine), or in a halocarbon (dichloromethane, trichloromethane, or 1,1- or 1,2-dichloroethane) affords urea 31. Similarly, treatment of amine 30 with a carboxylic acid halide 35 or a haloformate 36 in a dipolar aprotic solvent and acid acceptor such as those mentioned above provides amide 32 and urethane 33, respectively. While the reaction temperature at which the acylations are preformed are not narrowly critical, the transformations proceed at a reasonable rate at a temperature between about −10° C. and about ambient temperature. A reaction temperature of about −10° C. or about ambient temperature is preferred. The preferred dipolar aprotic solvent is dimethylformamide; the preferred halocarbon is dichloromethane.

The conversion of an N-acyl-2-amino-1,3-diol 6 to a 5-acylamino-2,2-dialkyl-1,3-dioxane 14 is depicted in Reaction Scheme B and described hereinbefore in the specification. A 5-amino-2,2-dialkyl-1,3-dioxane 37 is prepared form 2-amino-1,3-diol 30 by employing substantially the same conditions as hereinbeforementioned. A cosolvent such as a halocarbon, i.e., dichloromethane may be utilized. See Reaction Scheme E.

To prepare an oxazolinylmethane 38, a 2-amino-1,3-diol 30 is condensed with a benzonitrile 39

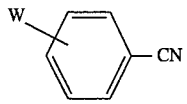
39 wherein W is an hereinbeforedescribed in the presence of a base, for example, an alkali metal carbonate such as lithium, sodium, or potassium carbonate, potassium carbonate being preferred, at an elevated temperature within the range of about 80° C. to about 140° C., a condensation temperature of about 110° C. being preferred, in a high boiling solvent system consistent with the reaction temperature chosen to provide a reasonable rate of reaction. Included among such solvent systems are mixtures of trihydric alcohols, e.g., glycerol, and dihydric alcohols, e.g., ethylene glycol, suitable for maintaining a condensation temperature of about 110° C.

To protect the arylic hydroxyl group, i.e., the hydroxyl group at the 1-position of the propane chain of an amidic propanoic ester for envisioned transformations, compound 40, for example, is treated with a silyl halide 43

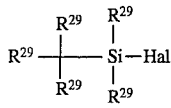
43 wherein $R^{29}$ is alkyl and Hal is chloro or bromo, preferably t-butyldimethylsilyl chloride, in the presence of a acid acceptor such as an imidazole, including imidazole itself, in a dipolar aprotic solvent comprising dimethylacetamide, dimethylformamide, hexamethylphosphoramide, or dimethylsulfoxide, dimethylformamide being preferred, to provide a silyloxy ester 41. The introduction of the protecting group proceeds readily at ambient temperature; however, reduced or elevated temperatures within the range of about 10° C. to 40° C. may be employed. Silyloxy ester 41 is then reduced to silyloxy carbinol 42 by processes such as those hereinbeforedescribed to the conversion of 5 to 6.

The transformations depicted in Reaction Schemes A to E refer to conversions in both the erythro- and threo- series. See pages 5 and 6 for a discussion of this nomenclature. threo-Compounds are prepared from the corresponding erythro-anologs by the conversions shown in Reaction Scheme F. Treatment of an erythro-hydroxyamide 43 with triphenylphosphine and diethyl azodicarboxylate in an ethereal solvent such as, e.g., tetrahydrofuran, provides, with inversion at the arylic position, a threo-carbalkoxyoxazoline 44, which is hydrolyzed under acidic conditions, i.e., aqueous acetic acid, at a hydrolysis temperature within the range of about ambient temperature to about 75° C., a reaction temperature of about 50° C. being preferred, to a threo-hydroxyester 45. Reduction of the ester group of an amidic ester 45 with, for example, lithium borohydride, as hereinbeforedescribed for the conversion of 5 to 6, affords a threo-amidic diol, which is hydrolyzed by, for example, aqueous sodium hydroxide to a threo-aminodiol 47.

To fabricate a dialkylaminoalkoxypropanol 49 wherein $R^{15}$ is alkyl and R and X are as hereinbeforedescribed, an aminodiol 30 is N-dialkylated by the process for the conversion of 17 to 23 to provide a dialkylaminodiol 48, which is O-alkylated to provide a dialkylaminoalkoxycarbinol 49. The O-alkylation is accomplished by treating 48 with an alkali metal hydride such as lithium, sodium, or potassium hydride, potassium hydride being preferred, in a dipolar aprotic solvent (e.g., dimethylacetamide, dimethylformamide, hexamethylphosphoramide, dimethylsulfoxide) to form an alkoxy anion, which in turn is treated with a dialkyl sulfate 51

  51 wherein $R^{15}$ is as hereinbeforementioned at ambient temperature to form an alkoxycarbinol 49.

An isoindoledione 50 is prepared by heating an aminodiol 30 with a phthalic anhydride 52

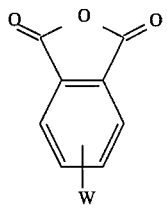  52 wherein W is as hereinbeforedesribed at an elevated temperature of about 100° C.

Various other N-substituted derivatives of a 2-amino-1,3-propanediol 30 are prepared by the processes shown in Reaction Schemes H and I. Thus, alkylation of a oxazolinylmethanol 38 with an alkyl halide 57

  57 wherein $R^{15}$ is as hereinbeforedescribed and Hal is bromo, chloro, or iodo followed by hydrolysis affords an alkylaminopropanediol 56 wherein $R^{15}$ is alkyl. The alkylation is performed in a dipolar aprotic solvent such as, for example, dimethylsulfoxide at about ambient temperature. The hydrolysis is effected without isolation of the alkylation product by means of an aqueous alkali metal hydroxide such as, for example, sodium hydroxide at a temperature within the range of about ambient temperature to about 100° C., a hydrolysis temperature of about 60° C. being preferred.

In contrast to the abovementioned process, alkylation of 38 with an alkyl halide 57 provides a methoxymethyloxazoline 53, which is hydrolyzed first to a methoxybenzamide 54 and then to a methoxyamine 55. The alkylation is carried out by forming the alkoxide ion of 38 of means of an alkali metal hydride such as sodium hydride in a dipolar aprotic solvent such as dimethylformamide at about ambient temperature to provide an O-alkoxymethyl oxazoline 53.

The first hydrolysis, i.e., the conversion of an oxazoline 53 to an amide 54 is accomplished under acidic conditions, for example, by an aqueous carboxylic acid such as aqueous acetic acid at a hydrolysis temperature of about 25° to about 75° C. The preferred hydrolysis temperature is about 50° C. The second hydrolysis is effected by an aqueous alkali metal hydroxide such as aqueous sodium hydroxide in an alkanol (e.g., methanol, ethanol, 1- or 2-propanol, or 1,1-dimethylethanol) at a hydrolysis temperature with in the range of about 50° to about 90° C. Ethanol is the preferred solvent. A hydrolysis temperature of about 70° C. is the preferred.

Additional N-substituted derivatives of a 2-aminopropanediol 30 are prepared by the methods outlined in Reaction Scheme I. Thus, acylation of a 1,3-propanediol 33 by the procedure hereinbeforedescribed for the conversion of 6 to 15 gives a 1,3-dialkanoyloxycarbamate 58 which is alkylated and hydrolyzed to a 1,3-dihydroxy N-alkylcarbamate 59. The alkylation is achieved by the procedure described for the conversion of 48 to 49. The hydrolysis of 58 by aqueous potassium carbonate in an alkanol (e.g., methanol, ethanol, 1- or 2. propanol, or 1,1-dimethylethanol). Methanol is preferred; a hydrolysis temperature of about ambient temperature is also preferred.

Similarly, reduction of a dihydroxyamide 60 with an alkali metal aluminum hydride, for example, lithium aluminum hydride in an ethereal solvent, for example, diethyl ether tetrahydrofuran at about ambient temperature affords an N-ethyldihydroxyamine 61, which is acylated with a carboxylic acid anhydride 64

  64 wherein $R^{31}$ is alkyl in the presence of a base, for example, a mixture of triethylamine and 4-dimethylaminopyridine in an ethereal solvent, for example, tetrahydrofuran to provide an O,O-dialkanoyloxyamide 62. An amide 62 is then hydrolyzed under basic conditions, for example, potassium carbonate in methanol to give a dihydroxy-N-ethylamide 63.

The presence of chiral centers at positions 1 and 2 of the present 2-amino-1,3-propanediols, and derivatives thereof, provides an opportunity to prepare stereochemical isomers of the ultimate products and thereby adduce whether the enantiomers of this series of compounds exhibit different pharmacological properties, as has been generally deserved in the art. Significantly, desirable properties generally reside in an enantiomer, while adverse properties inhere in the other.

To gain access to the enantiomers of the present 2-amino-1,2-propanediols, and derivatives thereof, a thiophene 64 wherein R is as hereinbeforedescribed is condensed with a chiral 1,1-dialkylalkyl-4-formyl-2,2-dialkyl-3-oxazolidinecarboxylate 70

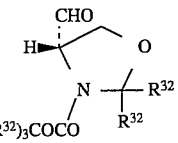  70 wherein $R^{32}$ is alkyl, the preparation of which is described in G. Garner and J. M. Park, Journal of Organic Chemistry, 52, 2761 to 2367 (1987), to afford a mixture of diastereomeric hydroxyoxazolidines 65a and 65b, i.e., erythro- and threo- isomers, wherein $R^{32}$ is as above, which is acylated to a mixture acyloxyoxazolidines 66a and 66b, separated into a pure enantiomer 66b, and hydrolyzed to an enantiomeric hydroxyoxazolidine 67, then to an N-acyloxydiol 68, and finally to an enantiomeric 2-amino-1,3-propanediol 69.

The condensation is effected by treating a thiophene 64 with a strong base, for example, an alkyl- or arylalkali metal such as n-butyllithium, sec-butyllithium or phenyllithium in an ethereal solvent such as 1,2-dimethoxyethane, 2-methoxyethylether, dioxane, or tetrahydrofuran, followed by adding, in this case, chiral oxazolidine 70, also in an ethereal solvent to the salt so formed to a afford a mixture of the erythro- and threohydroxyoxazolidines 65a and 65b. The condensation is generally carried out at a reduced temperature in the range of about −100° to −50° C., a reaction temperature of about −78° C. being preferred.

The acylation is readily achieved by processes hereinbeforedescribed for the conversion of 6 to 15, namely, by treating a mixture of 65a and 65b with a carboxylic acid anhydride 71

$(R^{32}CO)_2$         71 wherein $R^{32}$ is alkyl in an ethereal solvent (e.g., tetrahydrofuran) in the presence of a base or combination of bases (e.g., triethylamine and/or 4-dimethylaminopyridine) at room temperature to yield a mixture of O-acyloxyoxazolidines 66a and 66b.

The separation of the diastereomeric mixture is accomplished by selective crystallization techniques or chromatographic methods, for example, thin-layer, column, including high pressure and flash chromatography, using suitable absorbents and elements. Among absorbents, there may be mentioned silica gel, cellulose, magnesium silicate, activated aluminum oxide and resins (e.g., Amberlite and Dowex ion exchange resins). Among suitable chromatography solvents, these may be mentioned acetone, dichloromethane, ethyl acetate, 2-ethoxyethyl ether, ethanol, hexanes, and heptane. Particularly suitable absorbent and solvent for the separation of the diastereomeric acylates are silica gel and ethyl acetate heptane in a flash chromatographic apparatus.

The hydrolysis of an enantiomer 66b to a hydroxyoxazolidine 67 is achieved by means of an alkali metal carbonate (e.g. lithium, potassium, or sodium carbonate) in an alkanol (e.g., methanol, ethanol, 1- or 2- propanol, or 1,1-dimethylethanol) at about ambient temperature; reduced temperatures in the range of about 0° C. to about ambient temperature and elevated temperatures in the range of about ambient temperature to about 50° C. may be employed to effect the hydrolysis.

The hydrolysis of a hydroxyoxazolidine 67 to an N-acyloxydiol 68 is preformed in an alkanol (e.g., methanol, ethanol, 1- or 2-propanol, or 1,1-dimethylethanol) in the presence of an organic acid (e.g., sulfonic acids, such as methanesulfonic acid, benzenesulfonic acid, or 4-methylbenzenesulfonic acid, or a carboxylic acid, such as trifluoroacetic acid). Sulfonic acids are preferred; 4-methylbenzenesulfonic acid is most preferred. Methanol is also preferred. The hydrolysis of occurs readily at ambient temperature. Reduced temperatures in the range of about 0° C. to ambient temperature and elevated temperatures in the range of about ambient temperature to about 50° C. may be employed, however.

The hydrolysis of an N-acyloxydiol 68 to a 2-aminopropan-1,3-diol 69 is achieved by means of a mineral acid in an alkanol, or mixtures thereof. Included among mineral acids are hydrochloric, hydrobromic, and hydroiodic acids. Hydrochloric acid is preferred. Included among alkanols are methanol, ethanol, 1- and 2-propanol, and 1,1-dimethylethanol. Mixtures of methanol and ethanol are preferred. While the hydrolysis temperature is not narrowly critical, it is convenient to carry out the hydrolysis at ambient temperature.

The enantiomers of the 2-amino-1,2-propanediols of the present invention, and derivatives thereof, are also prepared by condensing a carboxaldehyde 72 with, for example, a chiral haloacetyl-4-phenylmethyloxazolidinone 77a.

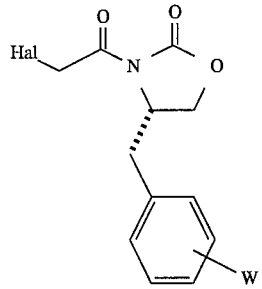
        77a wherein Hal is chloro, bromo, or iodo, and W is as hereinbeforedescribed, having the S-configuration at the 4-position, the preparation of which is described in D. A. Evans and A. E. Weber, Journal of the American Chemical Society, 109, 7151 (1981), to provide an oxazolidinylhalohydrin 73, which is converted to an azidohydroxyoxazolidine 74, cleaved to an azidohydroxypropionate 75, and reduced to an aminodiol 76. The condensation is effected by treating an aldehyde 72 with a haloacetyloxazolidinone 73 in the presence of a condensing agent, for example, a dialkyl borontriflate 78

$CF_3SO_3B(R^{34})_2$         78 wherein $R^{34}$ is alkyl, such as di-n-butyl borontriflate and an acid acceptor, for example, a trialkylamine such as triethylamine or 4-dimethylaminopyridine, triethylamine being preferred, in ethereal solvent. Among ethereal solvents, there may be mentioned diethyl ether, 1,2-dimethoxyethane, 2-methoxyethyl ether, dioxane, and tetrahydrofuran. Diethyl is preferred. The condensation is generally carried out at a reduced temperature within the range of about −25° to about 100° C., a condensation temperature of about −78° C. being preferred.

The conversion of a halohydrin 73 to an azidohydrin 74 is accomplished by treating a halo derivative 73 with an alkali metal azide, e.g., lithium, sodium or potassium azide, sodium azide being preferred, in a dipolar aprotic solvent, e.g., dimethylacetamide, dimethylformamide, hexamethylphosphoramide, N-methylpyrrolidione, or dimethylsulfoxide, dimethylsulfoxide being preferred, at about ambient temperature, although reduced temperatures (about 0° C. to about ambient temperature) or elevated temperatures (about ambient temperature to about 50° C.) may be employed.

The cleavage of a 4(S)-phenylmethyloxazolidinone 74 to an ester 75 is achieved by treating an oxazolidinone 74 with an alkoxymagnesium halide, for example, methoxymagnesium bromide, prepared in situ from an alkylmagnesium halide, for example, methylmagnesium bromine, and an alkanol, for example, methanol in an alkanol/halocarbon solvent, for example methanol/dichloromethane at about 0° C. Elevated temperatures up to about 50° C. may be employed to effect the cleavage.

The reduction of an azidoester 75 to an enantiomeric 2-amino-1,3-propanediol 76 having the S-absolute configuration is realized by treating an azidoester 75 with an alkali metal hydride, for example, lithium aluminum hydride (although sodium or potassium alumina hydride may be used), in diethyl ether (although other ethereal solvents such as 1,2-dimethoxyethane, 2-methoxyethyl ether, tetrahydrofuran or dioxane may also be used). The reduction of both the azido and ester groups proceeds smoothly at about 0° C. Elevated temperatures dependent upon the boiling point of the solvent system may also be employed.

A 2-aminopropane-1,3-diol 82, having the R- absolute configuration, is prepared by the aforementioned processes starting from carboxaldehyde 72 and haloacetyl-4-phenylmethyloxazolidinone 77b

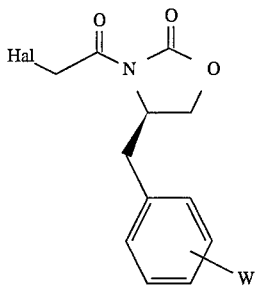

77b wherein Hal is as hereinbeforementioned and W is as hereinbeforedescried, having the R-configuration at the 4-position.

Alternatively, an enantiomeric 2-aminopropane-1,3-diol of the present invention is prepared by reducing a trans-propenoate 83, prepared from an appropriate aldehyde and a (carbalkoxymethylene)triphenylphosphorane in a conventional Wittig reaction, is reduced to a carbinol 84 and epoxidized under asymmetric conditions to an epoxycarbinol 85, which in turn, is condensed with a benzoylisocyanate to provide a benzoylcarbamate, 86 cyclized to an oxazolidinone 87, and cleaved to an aminopropanediol 88.

The reduction is achieved by treating an alkyl propenoate 83 with an aluminum hydride such as, for example, diisobutylaluminium hydride in an ethereal solvent such as, for example, tetrahydrofuran, at a reduced temperature of about −78° C. to provide a carbinol 84.

The asymmetrically induced expoxidation of a trans-alkyl propenate 84 to a 2S-trans-oxirane 85 is accomplished by means of a reaction system containing a base, an epoxidizing agent, and a chiral reagent in a suitable solvent. Among bases, there may be mentioned alkoxides such as alkali metal alkoxides, alkaline earth alkoxides, and transition metal alkoxides. Examples of alkali metal alkoxides include lithium, sodium, and potassium alkoxides. Examples of alkaline earth alkoxides include magnesium and calcium alkoxides. Examples of transition alkoxides include titanium, nickel, zinc alkoxides. Examples of alkoxy groups include methoxide, ethoxide, 1- and 2-propoxide, and 2,2-dimethylethoxide. Transition metal alkoxides are preferred; titanium (IV) 2-propoxide is most preferred.

A variety of epoxidizing agents may be used in this enantioselective synthesis. Among these are organic peracids, for example, perbenzoic acid, peracetic acid, performic acid, and monoperththalic acid, hydrogen peroxide and alkylhydroperoxides derivatives thereof such as tert-butylhydroxyperoxide, the preferred reagent.

The key reagent in this heterogeneous asymmetric epoxidation, the chiral reagent, may be selected from a wide group of optically active organic acids and ester or amide derivatives thereof. Included within this group are tartaric acid and dialkyltartrates, and camphoric acid and dialkyl camphorates. Optically active dialkyltartrates are preferred; di-2-propyltartrate is most preferred. When (+)-di-2-propyltartrate is used, a 2S-trans-oxirane 85 is formed selectively.

Suitable solvents for the expoxidation include halocarbons such as for example dichloromethane, 1,1- and 1,2-dichloroethane and ethylene dichloride. Dichloromethane is preferred.

The epoxidation is generally conducted at a reduced temperature of about −78° to about 0° C., a reaction temperature of about −20° C. being preferred.

The condensation of an optically active hydroxyoxirane 85 with a benzoylisocyanote 89

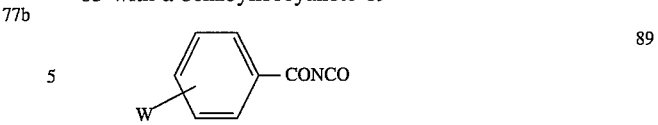

89 wherein W is as hereinbeforedefined is conveniently carried out in a halocarbon solvent of the type mentioned immediately above, generally in dichloromethane at about ambient temperature, which temperature is not narrowly critical.

The cyclization of a carbamate 86 to a hydroxyoxazolidinone 87 is effected by an alkali metal hydride selected from the group comprising lithium, sodium, or potassium hydride in a ethereal solvent selected from the group comprising diethyl ether, 2-methoxyethyl ether, 1,2-dimethoxyether, tetrahydrofuran, or dioxane. Sodium hydride suspended in tetrahydrofuran is preferred, as is a cyclization temperature of about the reflux temperature of the reaction medium, although the reaction proceeds readily at reduced temperatures to about ambient temperature.

The hydrolysis of hydroxyoxazolidinone 87 to aminopropanediol 88 is achieved in an alkanol solvent, e.g., methanol, ethanol, 1-, 2-propanol or 2,2-dimethylethanol, by means of a base such as aqueous alkali metal hydroxide, e.g., sodium or potassium hydroxide, about ambient temperature. Ethanol and aqueous sodium hydroxide are the preferred solvent and base.

By applying the aforedescribed process depicted in Reaction Scheme M and employing the antipode of the chiral reagent, e.g., (−)-diethyltartrate in the preferred synthesis, 2-amino-1,3-propanediol 93 is obtained via hydroxy oxirane 90, benzoylcarbamate 91, hydroxyoxazolidinone 92

A 1-alkenyl-2-amino-1,3-propanediol, e.g., a 1-alkenylpyridinyl-2-amino-1,3-propanediol 17, is prepared by reduction of a 1-alkynylpyridinyl-2-acylamino-1,3-propanediol 6 via a 1-alkenylpyridinyl-2-acylamino-1,3-propanediol 16. See Reaction Scheme C. Alternatively, a 1-alkenyl-2-amino-1,3-propanediol, e.g., a 1-alkenylthienyl-2-amino-1,3-propanediol 27, is prepared by condensation of a halothiophenecarboxyaldehyde 25 wherein X is bromo with a tri-n-butyl-1-alkenylstannane 24 in the presence of 2,6-di-t-butyl-4-methylphenol and tetrakis(triphenylphosphine-)palladium(O) in an aromatic solvent such as toluene at room temperature to a 1-alkenylthiophenecarboxaldehyde 26 (see Reaction Scheme D), which, in turn, is converted to a 2-amino-1,3-diol 27 and derivatives thereof by the processes outlined in Reaction Schemes A, B, and C.

The requisite tri-n-butyl-1-alkenylstannane 24 is prepared by reductive condensation of an alkyne 28 with tri-t-butylhydride in the presence of azobisisobutyronitrile.

To synthesize a 2-amino-1-propanol 98 of the present invention, an aldehyde 94 is reduced to a methanol 95 wherein $R^{38}$ is hydrogen by conventional methods, which is converted to an amidomalonate 96 wherein $R^5$ and X are as hereinbeforedescribed and $R^{37}$ is alkyl via a sulfonate 95 wherein $R^{38}$ is $SO_2R^{39}$ wherein $R^{39}$ is alkyl and, in turn, reduced to a hydroxyamide 97 and hydrolyzed to an aminocarbinol 98. The conversion is carried out by treating a methanol 95 ($R^{38}$ is hydrogen) with an alkylsulfonyl halide 99a $R^{39}SO_2Hal$          99a wherein $R^{39}$ is alkyl and Hal is chloro or bromo in a halocarbon solvent, e.g., dichloromethane, trichloromethane, 1,1- and 1,2-dichloroethane, dichloromethane being preferred, in the presence of an acid acceptor, e.g., a tertiary amine such as triethylamine, pyridine, and 4-dimethylpyridine, triethylamine being preferred, at about ambient temperature to provide a sulfonate 95 ($R^{38}$ is $SO_2R^{39}$). Optionally, without isolation, the sulfonate 95 is then treated with an amidomalonate 100

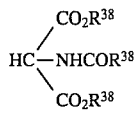
 100 wherein $R^{38}$ is alkyl in an alkanol in the presence of a corresponding alkali metal alkoxide. Included among alkanols and corresponding alkali metal alkoxides are methanol and lithium, sodium, and potassium methoxide, ethanol and lithium, sodium, and potassium ethoxide, 1- and 2- propanol and lithium, sodium, and potassium 1- and 2-propoxide, and 1,1-dimethyl ethanol and lithium, sodium, and potassium 1,1-dimethylethoxide. Sodium ethoxide in ethanol is preferred. This step of the conversion proceeds readily at about ambient temperature.

The reduction of a malonate 96 to an amido alcohol 97 is performed by treating the former with an alkali metal borohydride such as, for example, sodium or lithium borohydride, lithium borohydride being preferred, in an ethereal solvent such as, for example, diethylether, 2-methoxyethyl ether, 1,2-dimethoxyethane, tetrahydrofuran, and dioxane, tetrahydrofuran being preferred, at a reduction temperature within a range compatible with the reaction medium. When tetrahydrofuran is used as the solvent, a reaction temperature within the range of about 40° to about 80° C. is preferred, a reaction temperature of about 60° C. is most preferred.

The hydrolysis of an amide 97 to an amino alcohol 98 is achieved by treating an amide 97 with an alkali metal hydroxide, for example, lithium, sodium, or potassium hydroxide, sodium hydroxide being preferred in alkanol, for example, methanol, ethanol, 1- or 2-propanol, or 1,1-dimethylethanol, ethanol being preferred, at a hydrolysis temperature of about 65° C., when ethanol is used as the solvent.

To gain entry into the indole series, i.e., to prepare a 2-amino-1,3-propanediol 104 characterized by the presence of an indole moiety, the nitrogen of an indole carboxaldehyde 101 is protected by, for example, a sulfonyl function to provide a protected indolecarboxaldehyde 102, which may be converted to an indolyaminopropanediol 104 by the processes described herein and conventional methods. To protect the indole function prior to subsequent transformations, an indole carboxaldehyde 101 wherein X is bromo is treated with a sulfonyl halide 99b

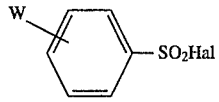
 99b wherein W is a hereinbeforedescribed and Hal is bromo or chloro in an ethereal solvent, for example, tetrahydrofuran in the presence of an acid acceptor, for example, triethylamine at a reaction temperature about 65° C. Other ethereal solvents and acid acceptors may be employed, however. Among them may be mentioned dioxane, 1,2-dimethoxyethane and 2-methoxyethyl ether, and pyridine and 2-dimethylaminopyridine, respectively. Other reaction temperatures, among them temperatures in the range of about 50° to 80° C., may also be employed.

To fabricate a 2-amino-1,3-propanediol having an alkanoylaryl substituent at the 3-position of the aminodiole side-chain, i.e., to prepare, for example, an alkanoylphenylaminopropanediol 106 wherein $R^{5'}$ is alkyl, alkynylphenylaminopropanediol is hydrolyzed in an ethereal solvent, for example, tetrahydrofuran in the presence of mercuric oxide and a mineral acid, for example, sulfuric acid at a preferred reaction temperature of about room temperature.

To construct a 2-aminopropane-1,3-diol having an alkoxyaryl moiety at the 3-position of the aminodiol side-chain, i.e., to prepare, for example, alkoxy phenylaminopropanediol 111 wherein $R^5$ is as hereinbeforedescribed, an alkanoyloxy benzaldehyde 107 wherein $R^{41}$ ia alkyl is converted to an amidoester 108 wherein $R^{11}$, $R^{12}$, and $R^{41}$ are as hereinbeforedescribed by processes also hereinbeforedescribed, which is reduced to hydroxyphenyldiol 109 wherein $R^{12}$ is as hereinbeforedescribed and, in turn, alkylated to alkoxyphenyldiol 110 and hydrolyzed by processes hereinbeforedescribed to alkoxyphenylaminopropanediol 111. The reduction of an alkanoylphenylpropionate 108 is achieved by treating a propionate 108 with a alkali metal borohydride, e.g., lithium borohydride, in ethereal solvent, for example, tetrahydrofuran at a reduced temperature of about 0° C. The alkylation is performed by treating a phenol 109 with an alkyl halide 112

$R^5Hal$  112 wherein $R^5$ is as hereinbeforedescribed and Hal is bromo, chloro, or iodo in a dipolar aprotic solvent, e.g., dimethylacetamide, dimethylformamide, hexamethylphosphoramide, or dimethylsulfoxide, dimethylformamide being preferred, in the presence of an alkali metal carbonate, including lithium, sodium, potassium, and cesium carbonate, and cesium carbonate being preferred. The alkylation is preferrably carded out at about room temperature. Reduced temperatures within the range of about 0° C. to about room temperature and elevated temperatures form about room temperature to about 100° C. may be employed to effect the alkylation.

By employing the appropriate starting materials and the processes described herein, additional 2-amino-1,3-propanediols of the present invention may be fabricated. For instance, starting from available substituted naphthalenes, naphthylaminopropanediols 112

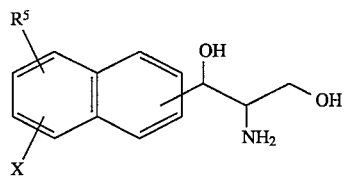
 112 wherein $R^5$ and X are as hereinbeforedescribed may be constructed.

The 1-alkyl-, 1-alkenyl-, and 1-alkynylaryl-2-amino-1,3-propanediols of the present invention are useful as agents for the relief of memory dysfunction, particularly dysfunctions associated with decreased cholinergic activity such as those found in Alzheimer's disease. Relief of memory dysfunction activity of the instant compounds is demonstrated in the dark avoidance assay, an assay for the determination of the reversal of the effects of scopolamine induced memory deficits associated with decreased levels of acetylcholine in the brain. In this assay, three groups of 15 male CFW mice were used—a vehicle/vehicle control group, a scopolamine/vehicle group, and a scopolamine drug group. Thirty minutes prior to training, the vehicle/vehicle control group received normal saline subcutaneously, and the scopolamine vehicle and scopolamine drug groups received scopolamine subcutaneously (3.0 mg kg, administered as scopolamine hydrobromide). Five minutes prior to training, the vehicle/vehicle control and scopolamine/vehicle groups received distilled water and the scopolamine drug group received the test compound in distilled water.

The training/testing apparatus consisted of a plexiglass box approximately 48 cm long, 30 cm high and tapering from 26 cm wide at the top to 3 cm wide at the bottom. The interior of the box was divided equally by a vertical barrier into a light compartment (illuminated by a 25-watt reflector lamp suspended 30 cm from the floor) and a dark compartment (covered). There was a hole at the bottom of the barrier 2.5 cm wide and 6 cm tall and a trap door which could be dropped to prevent an animal from passing between the two compartments. A Coulbourn Instruments small animal shocker was attached to two metal plates which ran the entire length of the apparatus, and a photocell was placed in the dark compartment 7.5 cm from the vertical barrier and 2 cm off the floor. The behavioral session was controlled by PDP 11/34 minicomputer.

At the end of the protreatment interval, an animal was placed in the light chamber directly under the light fixture, facing away from the door to the dark chamber. The apparatus was then covered and the system activated. If the mouse passed through the barrier to the dark compartment and broke the photocell beam within 180 seconds, the trap door dropped to block escape to the light compartment and an electric shock was administered at an intensity of 0.4 milliamps for three seconds. The animal was then immediately removed from the dark compartment and placed in its home cage. If the animal failed to break the photocell beam within 180 seconds, it was discarded. The latency is seconds for each mouse was recorded.

Twenty-four hours later, the animals were again tested in the same apparatus except that no injections were made and the mice did not receive a shock. The test day latency in seconds for each animal was recorded and the animals were then discarded.

The high degree of variability (due to season of the year, housing conditions, and handling) found in one trial passive avoidance paradigm is well known. To control for this fact, individual cutoff (CO) values were determined for each test, compensating for interest variability. Additionally, it was found that 5 to 7% of the mice in the scopolamine/vehicle control groups were insensitive to scopolamine at 3 mg/kg, sc. Thus, the CO value was defined as the second highest latency time in the control group to more accurately reflect the 1/15 expected control responders in each test group. Experiments with a variety of standards repeated under a number of environmental conditions led to the development of the following empirical criteria: for a valid test, the CO value had to be less than 120 sec and the vehicle control group had to have at least 5/15 animals with latencies greater than CO. For a compound to be considered active the scopolamine/compound group had to have at least 3/15 mice with latencies greater than CO.

The results of the dark avoidance test are expressed as the number of animals per group (%) in which this scopolamine induced memory deficit is blocked as measured by an increase in the latency period. Relief of memory dysfunction activity for representative compounds of the present invention is presented in Table 1.

TABLE 1

| Compound | Dose (mg/kg, sc) | Percent of Animals with Scopolamine Induced Memory Deficit Reversal |
| --- | --- | --- |
| ethyl erythro-2-acetamido-3-[6-(1-decynyl)-2-pyridinyl]-3-hydroxypropionate | 3.0 | 27 |
| erythro-N-{1-[6-(1-decynyl)- | 3.0 | 33 |

TABLE 1-continued

| Compound | Dose (mg/kg, sc) | Percent of Animals with Scopolamine Induced Memory Deficit Reversal |
| --- | --- | --- |
| 2-pyridinyl]-1,3-dihydroxy-2-propanyl}acetamide physostigmine | 0.31 | 20 |

Scopolamine induced memory deficit reversal is achieved when the present 1-alkyl-, 1-alkenyl-, and 1-alkynylaryl-2-amino-1,3-propanediol, and related compounds are administered to a subject requiring such treatment as an effective oral, parenteral or intravenous dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 1-alkyl-, 1-alkenyl-, and 1-alkynylaryl-2-amino-1,3-propanediols of the present invention are also useful as antiinflammatory agents due to their ability to reduce inflammation in mammals. The antiinflammatory activity is demonstrated in the TPA-induced ear edema assay and the arachidonic acid-induced ear edema test (see J. M. Young, et al., Journal Investigative Dermatology, 80, 48 (1983)).

In the TPA-induced ear edema assay, TPA (12-O-tetradecanoylphorbol-13-acetate) was dissolved in 30/70 propylene glycol/ethanol and was applied to the right ear of groups of 6 female Swiss Webster mice, which were housed together in a cage under standard conditions for 1 week prior to use with food and water ad lib, at a volume of 20 μl so that a total of 10 μg of TPA is delivered to the inner and outer surfaces of the ear. The test compound was dissolved in the vehicle and was applied to the right ear (the inner and outer surface) at a volume of 20 μl so that a total of 10 μg of the compound was delivered to the ear. After about 5 hours, the animals were sacrificed, a 4 mm diameter plug was taken from each ear and weighed. The difference between the right and left ear plug weights for each animal was determined. The antiinflammatory activity of the test compound is expressed as the mean percent change in the ear plug weight of the treated animals compared to the mean percent change in the plug weight of the control animals. Antiinflammatory activity of representative compounds of the instant invention as determined in this assay are presented below in Table 2.

TABLE 2

| Compound | Antiinflammatory Activity Percent Decrease in Ear Plug Weight at 10 μg/ear |
| --- | --- |
| erythro-2-amino-1-(6-decyl-2-pyridinyl)-1,3-dihydroxypropane | 66 |
| ethyl erythro-2-acetamido-3-[6-(1-dodecynyl)-2-pyridinyl]-3-hydroxypropionate | 50 |
| erythro-N-{1-[6-(1-dodecynyl)-2-pyridinyl]-1,3-dihydroxy-2-propanyl}acetamide | 59 |
| erythro-2-amino-1-(6-dodecyl-2-pyridinyl)-1,3-propanediol | 24 |

TABLE 2-continued

| Compound | Antiinflammatory Activity Percent Decrease in Ear Plug Weight at 10 μg/ear |
|---|---|
| threo-2-amino-1-(6-decyl)-2-pyridinyl)-1,3-propanediol | 30 |
| D-erythro-sphingosine | 46 |

In the arachidonic acid-induced ear edema assay, the test compound was dissolved in 30/70 propylene glycol ethanol and was applied to both ears of groups of 6 female Swiss Webster mice, which were housed together in a cage under standard conditions for 1 week prior to use with food and water ad lib, at a volume of 20 μl so that a total of 1.0 mg of test compound was delivered to each ear over the inner and outer surfaces. The same volume (20 μl) of vehicle was applied to each ear of a control group of mice. After 30 minutes, arachidonic acid was applied to the right ear of each mouse of each group in the amount of 4 mg/ear. Vehicle was applied to the left ear of each mouse of each group at a volume of 20 μl/ear. After an additional hour, the mice were sacrificed and a 4 mm plug was taken from each ear and weighed. The difference between the right and left ear plugs was determined for each animal. The antiinflammatory activity of the test compound is expressed as the mean percent change in the ear plug weight of the treated animals relative to the mean percent change in weights of control animals' ear. Antiinflammatory activity of representative compounds of the present invention as determined in this assay are presented below in Table 3.

TABLE 3

| Compound | Antiinflammatory Activity Percent Decrease in Ear Plug Weight at 1 mg/ear |
|---|---|
| erythro-2-amino-1-(6-decyl-2-pyridinyl)-1,3-dihydroxypropane | 32 |
| D-erythro-sphingosine | +9 |

Inflammation reduction is achieved when the present 1-alkyl-, 1-alkenyl-, and 1-alkynylaryl-2-amino-1,3-propanediols are administered topically, including ophthalmic administration, to a subject requiring such treatment as an effective topical dose of from 0.001 to 100 mg/kg of body weight per day. A particularly effective amount is about 25 mg/kg of body weight per day. It is to be understood however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 1-alkyl-, 1-alkenyl-, and 1-alkynyl-2-amino-1,3-propanediols of the present invention are also useful as inhibitors of tumor or neoplastic cell growth by virtue of their ability to reduce cell proliferation as demonstrated in the protein kinase C assay. (see U. Kikkawa, et al., Biochemical and Biophysical Research Communications, 135, 636 (1986) and R. M. Bell, et al. "Methods in Enzymology, Hormone Action," Part J, P. M. Conn, Ed., Academic Press, Inc., New York, N.Y. 1986, page 353).

Protein kinase C enzyme extract was prepared from the brain of male Wistar rats weighing 180 to 200 g and purified by the method of U. Kikkawa, et al., ibid. 636. The purified extract was stored at −80° C., and aliquots were used in the protein kinase C assay performed by a modification of the method of R. M. Bell, et al., ibid. al 354.

To perform the assay, duplicate aliquots of duplicate samples are employed. Basal or unstimulated protein kinase C, phosphatidylserine/diacylglycerol stimulated protein kinase C, and test samples are run in each assay. Protein kinase C extract (1–5 μg of protein; 10 μl); an 8 μl solution of N-2-hydroxyethylpiperazine-N'-2-ethylsulfonic acid (500 mM), magnesium chloride (40 mM), and ethylenediaminoetetraacetic acid (10 mM); dithiothreitol (20 mM; 8 μl), Type III histone (12 μg; 8 μl), and calcium chloride (11 mM; 8 μl) was added to each unstimulated protein kinase C sample assay tube, chilled in ice. Phosphatidylserine/diacylglycerol (4 μg; 8 μl) was added to each stimulated protein kinase sample assay tube, chilled in ice. The test compound ($10^{-04}$ to $10^{-12}$M in 4 μl dimethylsulfoxide) was added to the test sample tubes, chilled in ice. The volume for all sample tubes was brought to 72 μl with distilled water (18 μl for stimulated samples; 26 μl for unstimulated samples without 8 μl of phosphatidylserine/diacylglycerol). The assay tubes were allowed to warm to 25° C. and an 8 μl mixture of adenosine 5'-triphosphate (100 μM) and $^{32}$P-adenosine triphosphate (1 to $2 \times 10^5$ counts per minute) was added to each tube for a final volume of 80 μl per tube. After 2 min, the reaction (the incorporation of phosphorous into Type III histone) was terminated by spotting the assay mixture on phosphocellulose paper. The spots are cut out of the paper and the radioactivity (counts per min) of each spot was determined in a scintillation counter. Percent protein kinase C inhibitory activity, i.e., the percent inhibition of the incorporation of $^{32}$phosphorous from $^{32}$P-adenosine triphosphate into Type III histone, is calculated as follows:

$$\frac{\text{radioactively of test sample (cpm)}}{\text{radioactivity of stimulated sample (cpm)} - \text{radioactivity of unstimulated sample (cpm)}} \times 100\%$$

Protein kinase C inhibitory activity of representative compounds of the present invention expressed as the calculated concentration of test compound effecting a 50% inhibition of phosphorous uptake ($IC_{50}$) is presented below in Table 4.

TABLE 4

| Compound | Protein Kinase Inhibitory Activity $IC_{50}$ (μM) |
|---|---|
| ethyl erythro-2-acetamido-3-[6-(1-dodecynyl)-2-pyridinyl]-3-hydroxypropionate | 29 |
| cis-erythro-N-{1-[6-(1-dodecenyl)-2-pyridinyl]-1,3-dihydroxy-2-propanyl}-acetamide | 66% @ 100 μM |
| erythro-2-amino-1-(6-dodecyl-2-pyridinyl)-1,3-propanediol | 8.5 |
| erythro-2-amino-1-(6-decyl-2-pyridinyl)-1,3-dihydroxypropane | 48 |
| threo-2-amino-1-(6-decyl-2-pyridinyl)-1,3-dihydroxypropane | 25 |
| D-erythro-sphingosine | 6.7 |

Protein kinase C inhibition is achieved when the present 1-alkyl-, 1-alkenyl-, and 1-alkynylaryl-2-amino-1,3-propanediols, and related compounds are administered to a subject requiring such treatment as an effective oral, parenteral, intravenous, or topical dose of from 0.001 or 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 1-alkyl-, 1-alkenyl-, and 1-alkynylaryl-2-amino-1,3-propanediols of the present invention are also useful as antibacterial and antifungal agents due to their ability to inhibit bacterial and fungal growth in mammals. Antibacterial and antifungal activity are demonstrated in conventional antimicrobial assays (see D. J. Bibel, et al., The Journal of Investigative Dermatology, 92, 632 (1989).

In the aerobic antibacterial assay, the sensitivity of aerobic bacteria was tested by means of the agar dilution test in Mueller-Hinton agar. Plates were inoculated with a multipoint inoculator which delivered 5×10⁴ CFU spot of stationary, freshing diluted cultures of the strains concerned. The minimun inhibitory concentration (MIC) was taken as the lowest concentration at which no visible growth could be detected after 24 hours at 37° C.

In the anerobic assay, the susceptibility of obligate gram-positive and gram-negative anaerobes was tested using the agar dilution test on Wilkins-Chalgren agar. Overnight cultures of the appropriate test strains diluted 1:10 in fresh thioglycollate medium were used as the inoculum. The MICs of the antibiotics were determined after the plates had been incubated in anaerobic jars for 48 hours at 37° C.

Antibacterial activity of representative compounds of the instant invention as determined in this assay is presented below in Tables 5 and 6.

TABLE 5

Antibacterial activity (MIC, mg/l)

| Aerobic Bacteria Strain | | erythro-2-amino-1-(6-decyl-2-pyridinyl)-1,3-dihydroxypropane | D-erythro-sphingosine |
|---|---|---|---|
| Staph. aureus | SG511 | 12.50 | 25.0 |
| | 285 | 12.50 | 25.0 |
| | 503 | 6.25 | 25.0 |
| Strept. pyogenes | 308 A | 6.25 | 12.5 |
| | 77 A | 6.25 | 25.0 |
| Strept. faecium | D | 12.50 | 25.0 |
| E. coli | O 78 | 12.50 | >100.0 |
| | TEM | 25.00 | >100.0 |
| | 1507E | 12.50 | >100.0 |
| | DC0 | 12.50 | >100.0 |
| | DC2 | 6.25 | 25.0 |
| S. typhimurium | | 12.50 | >100.0 |
| Klebsiella spp. | 1082E | 12.50 | 25.0 |
| | 1522E | 12.50 | >100.0 |
| E. cloaceae | P99 | 12.50 | >100.0 |
| | 1321E | 12.50 | 50.0 |

TABLE 6

Antibacterial activity (MIC, mg/l)

| Anerobic Bacteria Strain | | Erythro-2-amino-1-(6-decyl-2-pyridinyl)-1,3-dihydroxypropane | Erythro-N-{1-[6-(1-docecynyl)-2-pyridinyl]-1,3-dihydoxy-2-propanyl}acetamide | Erytho-2-amino-1-[5-(1-dodecynyl)-2-thienyl]-1,3-propanediol | D-erythro-sphingosine |
|---|---|---|---|---|---|
| Bact. fragilis | 312 | 12.50 | 3.13 | 6.25 | 25.0 |
| | 960 | 6.25 | 3.13 | 6.25 | 12.5 |
| | 1313 | 12.50 | 6.25 | 6.25 | 25.0 |
| | 17390 | 12.50 | 6.25 | 3.13 | 25.0 |
| | 18125 | 12.50 | 3.13 | 3.13 | 25.0 |
| | 19016 | 12.50 | 6.25 | 6.25 | 25.0 |
| Bact. ovatus | 103 | 6.25 | 3.13 | 3.13 | 12.5 |
| Bact. vulgatus | 1446 | 12.50 | 3.13 | 3.13 | 25.0 |
| Bact. thetaiotaom. | 123 | 6.26 | 3.13 | 3.13 | 25.0 |
| | 1428 | 12.50 | 6.25 | 6.25 | 25.0 |
| | 1445 | 12.50 | 6.25 | 3.13 | 25.0 |
| Bact. distasonis | 1366 | 12.50 | 6.25 | 3.13 | 12.5 |
| Fusobact. varium | 5262 | 12.50 | 6.25 | 3.13 | 25.0 |
| | 3085 | 12.50 | 6.25 | 6.25 | 25.0 |
| Spaeroph. freundii | 1369 | 12.50 | 3.13 | 1.56 | |
| Peptostr. anaerobius | 932 | 12.50 | 6.25 | 6.25 | 12.5 |
| Propionibact. acnes | 6919 | 12.60 | 6.25 | 3.13 | 12.5 |
| | 6922 | 12.50 | 6.25 | 1.56 | 12.5 |
| Clost. tetani | 19406 | 12.50 | 12.50 | 6.25 | 50.0 |
| Clost. perfringens | 194 | 12.50 | 12.00 | 6.25 | 6.25 |

In the antifungal assay, utilizing a microtitration technique (U-shaped, 96 well-plate), the test compound (10 mg) is dissolved in a suitable solvent (10 ml dist. water, or 1 ml org. solvent +9 ml dist. water).

The microtiter plate is prepared as follows: The wells are each filled (2 rows/strain) with 50 µl neopeptone-dextrose broth (12-channel pipette). In addition, one row/strain is coated with 50 µl yeast-nitrogen base/well for yeasts and moulds. Subsequently, 50 µl compound solution are added to each well in the first row, mixed and diluted further by transferral of 50 µl respectively in the ratio 1:2. All wells are then inoculated with 150 µl standardized organism suspension (yeasts: 1×10³ organisms/ml suspension; cutaneous fungi and moulds: 1.6×10⁵ organisms/ml suspension); the total volume is 200 µl per well.

There is also a growth control (inoculated, not medicated), a solvent control (inoculated, not medicated, containing solvent as in medicated rows) and a negative control (not inoculated, not medicated).

Incubation for 5 days at 30° C. is followed by photometric evaluation. The obtained measurements are checked visually (macroscopically and microscopically) and corrected where necessary.

Criteria for Evaluation of the Antimycotic Effect a. Photometric measurements (matrix method)
b. Growth, macroscopic evaluation
c. Growth, microscopic evaluation (inversion light microscope, magn. 64×).

Antifungal activity of representative compounds of the instant invention as determined in the microtiter assay is presented below in Table 7.

TABLE 7

| Pathogen | Strain | Antifungal Activity MIC [µg/ml] |
|---|---|---|
| erythro-N-{1-[6-(1-Dodecynyl)-2-pyridinyl]-1,3-dihydroxy-2-propanyl}acetamide | | |
| Trichophyton Mentagrophytes | 100/25 | 7.810 |
| Trichophyton Rubrum | 101/85 | 31.250 |
| Microsporum Canis | 150/353 | 0.970 |
| Candida Albicans | 200/175 | 125.000 |
| Aspergillus Niger | 500/284 | 125.000 |
| Trichophyton Vaginalis | 111/216 | 15.625 |
| erythro-2-Amino-1-(6-decyl-2-pyridinyl)-1,3-dihydroxypropane | | |
| Trichophyton Mentagrophytes | 100/25 | 31.250 |
| Trichophyton Rubrum | 101/85 | 31.250 |
| Microsporum Canis | 150/353 | 31.250 |
| Candida. Albicans | 200/175 | 31.250 |
| Aspergillus Niger | 500/284 | 31.250 |
| Trichophyton Vaginalis | 111/216 | 15.625 |
| erythro-2-Amino-1-[5-(1-dodecynyl)-2-thienyl]-1,3-propanediol | | |
| Trichophyton Mentagrophytes | 100/25 | 3.900 |
| Trichophyton Rubrum | 101/85 | 15.625 |
| Microsporum Canis | 150/353 | 3.900 |
| Candida Albicans | 200/175 | 1.950 |
| Aspergillus Niger | 500/284 | 3.900 |
| Trichophyton Vaginalis | 111/216 | 15.625 |
| Cyclopirox | | |
| Trichophyton Mentagrophytes | 100/25 | 1.950 |
| Trichophyton Rubrum | 101/85 | 1.950 |
| Microsporum Canis | 150/353 | 1.950 |
| Candida Albicans | 200/175 | 1.950 |
| Aspergillus Niger | 500/284 | 0.970 |
| Trichophyton Vaginalis | 111/216 | 15.625 |
| Clotrimazol | | |
| Trichophyton Mentagrophytes | 100/25 | 0.970 |
| Trichophyton Rubrum | 101/85 | 0.240 |
| Microsporum Canis | 150/353 | 0.060 |
| Candida Albicans | 200/175 | 3.900 |
| Aspergillus Niger | 500/284 | 1.950 |
| Trichophyton Vaginalis | 111/216 | 62.500 |

Bacterial and fungal growth inhibition is achieved when the present 1-alkyl-, 1-alkenyl-, and 1-alkynylaryl-2-amino-1,3-propanediols, and related compounds are administered to a subject requiring such treatment as an effective oral, parenteral, intravenous, or topical, including ophthalimic administration, dose of from 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set for herein are exemplary only and that they do not, to any extent, limit the scope or practice of the invention.

Compounds of the present invention include:

a. erythro-2-amino-1-(5-decyl-2-furyl)-1,3-dihydroxypropane;

b. erythro-2-amino-1-(5-decyl-3-isothiazolyl)-1,3-dihydroxypropane;

c. threo-2-amino-1-[5-decyl-3-(2-oxopyrrolyl)]-1,3-dihydroxypropane;

d. erythro-2-amino-1-[6-decyl-2-(4-methylpyridin)]-1,3-dihydroxypropane;

e. threo-2-amino-1-[6-decyl-2-(4-methoxypyridinyl)]-1,3-dihydroxypropane;

f. erythro-2-amino-1-[6-decyl-2-(5-chloropyridinyl)]-1,3-dihydroxypropane;

g. threo-2-amino-1-[6-decyl-2-(4-trifluoromethylpyridinyl)]-1,3-dihydroxypropane;

h. erythro-2-amino-1-[6-(5-phenylpentyl-2-pyridinyl)-1,3-dihydroxypropane;

i. erythro-2-amino-1-(2-decyl-4-thiazolyl)-1,3-dihydroxypropane;

j. erythro-2-amino-1-(2-decyl-4-oxazolyl)-1,3-dihydroxypropane;

k. erythro-2-methylamino-1-(5-decyl-2-thienyl)-1,3-dihydroxypropane l. erythro-2-dimethylamino-1-(3-decyl)phenyl-1,3-dihydroxypropane;

m. erythro-2-(1,1-dimethylethoxy)carbonylamino-1-(2-dodecynyl-6-pyridinyl)-1,3-dihydroxypropane;

n. erythro-2-amino-1-(3-(1-decenyl)phenyl)-1,3-dihydroxypropane;

o. ethyl erythro-2-methoxycarbonylamino-3-(2-dodecynyl-6-pyridinyl)-3-hydroxypropionate;

p. erythro-2-amino-1-(3-(1-decynyl)phenyl)-1,3-dihydroxypropane;

q. erythro-2-amino-1-(3-(1-undecynyl)phenyl)-1,3-dihydroxypropane;

r. erythro-2-amino-1-(4-(1-nonyl)-2-thienyl)-1,3-dihydroxypropane;

s. erythro-2-ammo-1-(4-(1-dodecynyl)-2-thienyl)-1,3-dihydroxypropane;

t. erythro-2-amino-1-(4-(1-decyl)-2-thienyl)-1,3-dihydroxypropane;

u. erythro-2-amino-1-(5-nonyl-2-thienyl)-1,3-dihydroxypropane;

v. erythro-2-amino-1-(3-dodecyl-5-isoxazolyl)-1,3-dihydroxypropane;

w. erythro-2-amino-1-(3-decyl-5-isoxazolyl)-1,3-dihydroxypropane;

x. erythro-2-amino-1-(6-(1-dodecenyl)-2-pyridinyl)-1,3-dihydroxypropane;

y. erythro-2-amino-1-(3-(6-phenyl-1-hexynyl)phenyl)-1,3-dihydroxypropane; and z. erythro-2-amino-1-(5-(6-phenylhexyl)-2-thienyl)-1,3-dihydroxypropane.

Effective amounts of the compounds of the present invention may be administered topically to a subject in the form of sterile solutions, suspensions, ointments, creams, aerosols, or salves. The 1-alkyl-, 1-alkenyl, and 1-alkynylaryl-2-amino-1,3-propanediols of the present invention, while effective themselves, may be formulated and administered in the form of their pharmaceutically acceptable acid or base addition salts for purposes of stability, convenience or crystallization, increased solubility and the like.

Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like. Preferred pharmaceutically acceptable base addition salts include salts of alkali metals, e.g. sodium or potassium, alkaline earth metals, e.g. calcium or magnesium; or complex salts such as ammonium or substituted ammonium salts such as a mono-, di- or trialkylammonium salts or a mono, di- or trihydroxy-alkylammonium salts.

For the purpose of topical administration, the active compounds of the invention may be incorporated into a solution, suspension, ointment, cream, gel, aerosol, or salve. These preparations should contain at least 0.1% of active compound but may be varied to be between 0.05 and about 20% of the weight thereof. The amount of active compound in such compositions is such that a suitable dosage will be obtained. Preferred topically administered preparations should contain between 0.1 and 10% of active compound.

The topical compositions may also include the following components: water, fixed oils, polyethylene, glycols, glycerol, petroleum, stearic acid, beeswax, other synthetic solvents or mixtures thereof; antibacterial agents such as benzyl alcohol or methyl paraben; antioxidants such as $\alpha$-tocopherol acetate; chelating agents such as ethylenediaminetetraacetic acid; buffers such as acetates, citrates or phosphates; emulsifying agents such as polyoxyethylene monooleate and coloring materials and adjuvants such as ferric oxide or talc. The topical preparation can be enclosed in tubes, bottles, or jars made of metal, glass or plastic.

The active compounds of the present invention may also be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of present compound in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit is a capsule, it may contain, in addition to materials of the above type, a liquid carder such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The oral solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention.

EXAMPLE 1

6-(1-Dodecynyl)-2-pyridinecarboxaldehyde

To a solution of 6-bromo-2-pyridinecarboxaldehyde (3.0 g) in tetrahydrofuran (10 ml), was added sequentially bis-(triphenylphosphine)palladium(II) chloride (0.178 g), copper(I)iodide (0.024 g), 1-dodecyne (3.25 ml), and triethylamine (2.12 ml). The solution was stirred at 40° C. overnight. The reaction mixture was cooled to room temperature, charged again with bis(triphenylphosphine)palladium (II) chloride (0.024 g), copper (I) iodide (0.024 g), and triethylamine (2.12 ml), and 1-dodecyne (3.25 ml), and tetrahydrofuran (5.0 ml), and heated at 40° C. for 5 hrs. The reaction mixture was again cooled and recharged as above, and heated at 40° C. for 24 hrs. The cooled mixture was concentrated, taken up in ethyl acetate (100 ml), washed with water and saturated sodium chloride solution, dried over anhydrous magnesium sulfate, filtered, and the filtrate was concentrated. The residue was taken up in ethyl acetate (100 ml) and filtered. The filtrate was combined with material from a similar reaction run 1.43 g of the carboxaldehyde and proportionate amounts of the catalysts, 1-dodecyne, and solvent. The filtrate was concentrated. The residue was purified by flash chromatography using 1.5% ethyl acetate hexane followed by 1% ethyl acetate hexane as elements. The appropriate fractions were collected and concentrated to yield 2.24 g (29%) of product, as an oil.

Analysis: Calculated for $C_{18}H_{25}NO$: 79.66%C 9.28%H 5.16%N Found: 79.54%C 9.29%H 4.98%N

EXAMPLE 2 erythro-N-{1-[6-(1-Decynyl)-2-pyridinyl]-1,3-dihydroxy-2-propanyl}acetamide

Ethyl erythro-2-acetamido-3-[6-(1-decynyl)-2-pyridinyl]-3-hydroxypropionate (5.71 g) in dry tetrahydrofuran (75 ml) was slowly added to 2.0M lithium borohydride/tetrahydrofuran (7.6 ml) at 0° under nitrogen, and the mixture was stirred at room temperature overnight. The reaction mixture was chilled, and 1:1 methanol:water (50 ml) was added slowly followed by glacial acetic acid (0.5 ml) until pH 6.5 was obtained. The reaction mixture was concentrated, and the residue azeotroped with methanol (4×40 ml). The residue was slurried with 7.5% sodium bicarbonate solution (15 ml) (pH 8.5), extracted into 3:1-trichloromethane:isopropanol and concentrated. The appropriate fractions were collected and concentrated. The residue was purified by flash chromatography on silica gel eluting with 49:1-ethyl acetate:methanol. The appropriate fractions were collected and concentrated to give 4.74 g (93%) of product, mp 85°–87° C.

Analysis: Calculated for $C_{20}H_{30}N_2O_3$: 69.33%C 8.73%H 8.09%N Found: 69.44%C 8.84%H 8.07%N

EXAMPLE 3 erythro-N-{1-[6-(1-Decynyl)-2-pyridinyl]-1,3-diacetyloxy-2-propanyl}acetamide

N-{1-[6-(1-Decynyl)-2-pyridinyl]-1,3-dihydroxy-2-propanyl}acetamide (4.35 g), acetic anhydride (7.45 ml), triethylamine (16 ml), and 4-dimethylaminopyridine (0.24 g) in dry tetrahydrofuran (80 ml) was stirred at room temperature for 3 days. The reaction mixture was evaporated, and the residue was warmed with methanol for 20 mins, reevaporated, and the residue was azeotroped with toluene. The residue was taken up in trichloromethane, and 7.5% sodium bicarbonate solution was added until pH 8.5 was obtained. The mixture was extracted with trichloromethane, dried over anhydrous magnesium sulfate, filtered, and the filtrate was concentrated. The residue was combined with the residue (1.0 g) from a reaction, starting with 0.829 g of acetamide, and purified by flash chromatography on silica gel eluting with 1:1-hexane:ethyl acetate. The appropriate fractions were collected and concentrated to yield 1.61 g (25%) of product.

Analysis: Calculated for $C_{24}H_{34}N_2O_5$: 66.95%C 7.96%H 6.51%N Found: 66.65%C 8.04%H 6.36%N

EXAMPLE 4 threo-N-{1-[6-(1-Decynyl)-2-pyridinyl]-1,3-diacetyloxy-2-propanyl}acetamide

N-{1-[6-(1-Decynyl)-2-pyridinyl]-1,3-dihydroxy-2-propanyl}acetamide (4.35 g), acetic anhydride (7.45 ml), triethylamine (16 ml), and 4-dimethylaminopyridine (0.24 g) in dry tetrahydrofuran (80 ml) was stirred at room temperature for 3 days. The reaction mixture was evaporated, and the residue was warmed with methanol for 20 min, reevaporated and azeotroped with toluene. The residue was taken up in trichloromethane, and 7.5% sodium bicarbonate solution was added until pH 8.5 was obtained. The mixture was extracted with trichloromethane, dried over anhydrous magnesium sulfate, filtered, and concentrated. The residue was combined with 1.0 g of the residue from another reaction (0.829 g of acetamide), and purified by flash chromatography on silica gel, eluting with 1:1-hexane:ethyl acetate to yield 1.02 g (15.9%) of product, mp 59°–61° C.

Analysis: Calculated for $C_{24}H_{34}N_2O_5$: 66.95%C 7.96%H 6.51%N Found: 67.21%C 7.83%H 5.92%N

EXAMPLE 5

Ethyl erythro-2-acetamido-3-[6-(1-decynyl)-2-pyridinyl]-3-hydroxypropionate

A 2:1-erythro:threo mixture of ethyl 2-acetamido-3-(6-bromo-2-pyridinyl)-3-hydroxypropionate (10.0 g), 1-decyne (5.01 g), bis(triphenylphosphine)palladium chloride (0.42 g) and cuprous iodide (0.06 g) in triethylamine (50 ml) was heated at 50°–60° C. for 2.5 hrs. under nitrogen, and then at room temperature overnight. The reaction mixture was evaporated, water was added, and the mixture was extracted with ethyl acetate. The organic extract was purified by flash chromatography on silica gel, eluting with 1:1 hexane:ethyl acetate and collecting the appropriate fractions. The appropriate fractions were evaporated. Recrystallization of the residue from ethyl acetate gave 7.8 g (66%) of the product, mp 97°–99° C.

Analysis: Calculated for $C_{22}H_{32}N_2O_4$: 68.01%C 8.30%H 7.21%N Found: 68.23%C 8.28%H 7.22%N

EXAMPLE 6

Ethyl threo-2-acetamido-3-[6-(1-decynyl-2-pyridinyl]-3-hydroxypropionate

A mixture of ethyl 2-acetamido-3-(6-bromo-2-pyridinyl)-3-hydroxypropionate (17.3 g, 97% erythro), 1-decyne (8.67 g), bis(triphenylphosphine)palladium chloride (0.73 g), cuprous iodide (0.10 g), and triethylamine (13.2 g) in tetrahydrofuran (90 ml) was heated overnight at 50°–55° C., under nitrogen. The reaction mixture was evaporated, water was added, and the mixture was extracted with ethyl acetate, and concentrated. The residue was purified by flash chromatography on silica gel, eluting with 1:1-hexane:ethyl acetate. The appropriate fractions were collected and evaporated. Recrystallization of the residue from 1:2-hexane:ethyl acetate gave 14.7 g of 19:1-mixture erythro:threo-compounds, and from the mother liquors, 4.66 g of an 8:3 of mixture erythro:threo compounds. Flash chromatography of 2.63 g of the threo-enriched material on silica gel, eluting with 1:1-hexane:ethyl acetate, yielded 0.39 g (3.4%) of product, mp 97°–99.5° C.

Analysis: Calculated for $C_{22}H_{32}N_2O_4$: 68.01%C 8.30%H 7.21%N Found: 67.89%C 8.26%H 7.10%N

EXAMPLE 7 erythro-N-{4-[6-(1-Decynyl)-2-pyridinyl]-2,2-dimethyl-1,3-dioxan-5-yl}acetamide

N-{1-[6-(1-Decynyl)-2-pyridinyl]-1,3-dihydroxy-2-propanyl}acetamide (6.1 g, 3:1/erythro:threo mixture), p-toluenesulfonic acid (3.7 g), and 2,2-dimethoxypropane (43 ml) in dichloromethane (115 ml) were stirred at room temperature overnight, under nitrogen. The reaction mixture was extracted with 0.5M sodium bicarbonate solution and water, dried over anhydrous magnesium sulfate, filtered, and the filtrate was evaporated. The residue was chromatographed on silica gel, eluting with 2:1-hexane:ethyl acetate to give 2.4 g (35%) of product, as an oil.

Analysis: Calculated for $C_{23}H_{34}N_2O_3$: 71.47%C 8.87%H 7.25%N Found: 71.14%C 9.12%H 7.13%N

EXAMPLE 8 threo-N-{4-[6-(1-Decynyl)-2-pyridinyl]-2,2-dimethyl-1,3-dioxan-5-yl}acetamide

N-{1-[6-(1-Decynyl)-2-pyridinyl]-1,3-dihydroxy-2-propanyl}acetamide (6.1 g, 3:1-erythro:threo mixture), p-toluenesulfonic acid (3.7 g), and 2,2-dimethoxypropane (43 ml) in dichloromethane (115 ml) were stirred at room temperature overnight, under nitrogen. The reaction mixture was washed with 0.5M sodium bicarbonate solution and water, dried over anhydrous magnesium sulfate, filtered, and the filtrate was evaporated. The residue was chromatographed twice on silica gel, eluting with 2:1-hexane:ethyl acetate to 1:1-hexane:ethyl acetate to give 0.76 g (11%) of product, as an oil.

Analysis: Calculated for $C_{23}H_{34}N_2O_3$: 71.47%C 8.87%H 7.25%N Found: 71.15%C 8.91%H 7.06%N

EXAMPLE 9

Ethyl erythro-2-acetamido-3-[6-(1-dodecynyl)-2-pyridinyl]-3-hydroxypropionate

A solution of 6-(1-dodecynyl)-2-pyridinecarboxaldehyde (5.51 g), acetamidomalonic acid monoethyl ester (3.78 g), and triethylamine (2.8 ml) in dry tetrahydrofuran (30 ml) was stirred at room temperature overnight, under nitrogen. The reaction mixture was evaporated, and the residue was purified on a silica gel column eluting with 1:1-hexane:ethyl acetate to give 7.46 g (89.6%) of product (10:1-erythro:threo mixture). This product was combined with 7.40 g from a prior reaction run on the same scale, and the combined material was recrystallized from 2:1-ethyl acetate:hexane to give 9.62 g (57.7%) of the analytically pure product, mp 86°–87.5° C.

Analysis: Calculated for $C_{24}H_{36}N_2O_4$: 69.20%C 8.71%H 6.72%N Found: 69.40%C 8.72%H 6.68%N

EXAMPLE 10

Ethyl erythro-2-acetamido-3-[6-(1-hexynyl)-2-pyridinyl]-3-hydroxypropionate

An 11:1-erythro:threo mixture of ethyl 2-acetamido-3-(6-bromo-2-pyridinyl)-3-hydroxypropionate (24.9 g), 1-hexyne (7.39 g), triethylamine (19.0 g), bis(triphenylphosphine)palladium chloride (1.05 g) and cuprous iodide (0.14 g) in dry tetrahydrofuran (100 ml) was heated at 55° C. for 6 hrs, under nitrogen. Additional 1-hexyne (6.2 g), triethylamine (7.6 g), bis(triphenylphosphine)palladium chloride (0.53 g), and cuprous iodide (0.07 g) were added at room temperature and the reaction mixture was heated an additional 5.5 hrs. The mixture was evaporated, water was added, and the mixture was extracted with ethyl acetate. The extract was flash chromatographed (silica gel, 1:1-hexane:ethyl acetate). The appropriate fractions were collected and evaporated. Recrystallization of the residue from 1:1-hexane:ethyl acetate provided 3.8 g (15%) of product, 87°–88° C.

Analysis: Calculated for $C_{18}H_{24}N_2O_4$: 65.04%C 7.28%H 8.43%N Found: 65.19%C 7.31%H 8.37%N

EXAMPLE 11 erythro-N-{1,3-Diacetyloxy-1-[6-(1-hexynyl)-2-pyridinyl]-2-propanyl}acetamide

To ethyl erythro-2-acetamido-3-[6-(1-hexynyl)-2-pyridinyl]-3-hydroxypropionate (16.0 g) in dry tetrahydrofuran (140 ml) was added 2.0M lithium borohydride:tetrahydrofuran (24 ml) at 0° C., with stirring, under nitrogen. After the addition was complete, the mixture was allowed to warm to room temperature and was stirred overnight. The reaction mixture was chilled and 1:1-methanol:water (80 ml) was added slowly followed by acetic acid (2.8 ml) until a pH of 6.8 was obtained. The reaction mixture was stirred for 1 hr and evaporated. The residue was azeotroped several times with methanol. A 7.5% sodium bicarbonate solution was added to the residue until a pH of 8.5 was obtained, and the mixture was extracted with 3:1 trichloromethane:isopropanol and concentrated. The residue was flash chromatographed on silica gel eluting with 1% methanol:ethyl acetate to give 13.2 g (94%) of erythro-N-{1-[6-(1-hexynyl)-2-pyridinyl]-1,3-dihydroxy-2-propanyl}acetamide.

erythro-N-{1-[6-(1-hexynyl)-2-pyridinyl]-1,3-dihydroxy-2-propanyl}acetamide(10.3 g), acetic anhydride (21.8 g), triethylamine (32.4 g), and 4-dimethylaminopyridine (0.44 g) in tetrahydrofuran (150 ml) was stirred at room temperature overnight. The reaction mixture was evaporated, methanol was added to the residue, and the solution was warmed at 50° C. for 15 min. The mixture was evaporated. The residue was dissolved in chloroform, and 7.5% sodium bicarbonate solution was added until a pH 8 was obtained. The mixture was extracted with chloroform. The extract was dried over anhydrous magnesium sulfate, filtered, and the filtrate was concentrated. The residue was flash chromatographed, eluting with 1:1-hexane:ethyl acetate to yield 7.3 (55%) of product, mp 97°–99° C.

Analysis: Calculated for $C_{20}H_{26}N_2O_5$: 64.16%C 7.00%H 7.48%N Found: 64.17%C 7.00%H 7.44%N

EXAMPLE 12 erythro-N-{1-[6-(1-Hexynyl)-2-pyridinyl]-1,3-dihydroxy-2-propanyl}acetamide erythro-N-{1,3-Diacetyloxy-1-[6-(1-hexynyl)-2-pyridinyl]-2-propanyl}acetamide (6.7 g) and potassium carbonate (3.3 g) in methanol (100 ml) was stirred for 40 min. The precipitate was collected, and the filtrate was evaporated. A 7.5% sodium bicarbonate solution was added to pH 8.5, and the mixture was extracted with 3:1-trichloromethane:2-propanol, dried over anhydrous magnesium sulfate, filtered, and the filtrate was evaporated. Recrystallization of the residue from 1:1-hexane:ethyl acetate gave 4.6 g (88%) of product, mp 75°–77° C.

Analysis: Calculated for $C_{16}H_{22}N_2O_3$: 66.19%C 7.64%H 9.65%N Found: 65.99%C 7.55%H 9.65%N

EXAMPLE 13

Ethyl erythro-2-acetamido-3-hydroxy-3-[6-(1-octynyl)-2-pyridinyl]propionate

A mixture of an 11:-erythro:threo mixture of ethyl 2-acetamido-3-(6-bromo-2-pyridinyl)-3-hydroxypropionate (24.9 g), 1-octyne (9.9 g), triethylamine (19.0 g), bis(triphenylphosphine)palladium chloride (1.05 g) and cuprous iodide (0.14 g) in dry tetrahydrofuran (100 ml) was heated at 55° C. for 6 hrs, under nitrogen. Additional 1-octyne (4.1 g), triethylamine (3.8 g), bis(triphenylphosphine)palladium chloride (0.53 g), and cuprous iodide (0.07 g) were added at room temperature, and the reaction mixture was heated an additional 4 hrs. The mixture was evaporated, water was added, and the mixture was extracted with ethyl acetate. The solution was flash chromatographed on silica gel eluting with 1:1-hexane:ethyl acetate. The fractions, enriched in the erythro isomer, were evaporated and the residue was recrystallized from 1:1-isopropanol:water to give 3.2 g (12%) of product, mp 81°–83° C.

Analysis: Calculated for $C_{20}H_{28}N_2O_4$: 66.64%C 7.83%H 7.77%N Found: 66.62%C 7.77%H 7.75%N

EXAMPLE 14 erythro-N-{1,3-Dihydroxy-1-[6-(1-octynyl)-2-pyridinyl]-2-propanyl}acetamide

To ethyl erythro-2-acetamido-3-hydroxy-3-[6-(1-octynyl)-2-pyridinyl]propionate (9.02 g) in dry tetrahydrofuran (80 ml) was added slowly 2.0M lithium borohydride:tetrahydrofuran (12.5 ml) at 0°, under nitrogen. The mixture was stirred at room temperature overnight, chilled, and 1:1-methanol:water was added slowly followed by glacial acetic acid (1.5 ml) in 1:1-methanol:water (15 ml) until pH 6.8 was obtained. The solution was stirred at room temperature for 1.5 hrs, evaporated, and the residue was azeotroped with methanol (4×40 ml). The residue was slurried with 7.5% sodium bicarbonate solution (25 ml) (pH 8.5), saturated sodium chloride solution (25 ml), extracted with 3:1-trichloromethane:2-propanol, and concentrated. The residue was flash chromatographed on silica gel, eluting with ethyl acetate:0.5% methanol. The appropriate fractions were collected and evaporated. The residue was recrystallized (3 times) from ethyl acetate to give 1.24 g (15.6%) of product, mp 81°–83° C.

Analysis: Calculated for $C_{18}H_{26}N_2O_3$: 67.90%C 8.23%H 8.80%N Found: 68.03%C 7.97%H 8.70%N

EXAMPLE 15

Ethyl erythro-2-acetamido-3-[6-(1-hexadecynyl)-2-pyridinyl]-3-hydroxypropionate

A solution of 6-(1-hexadecynyl)-2-pyridinecarboxaldehyde (17.4 g), acetamidomalonic acid monoethyl ester (10.6 g), and triethylamine (5.4 ml) in dry tetrahydrofuran (85 ml) was stirred at room temperature for 3 days, under nitrogen. The reaction mixture was evaporated and the residue was dissolved in ethyl acetate. The solution was washed with half-saturated sodium chloride solution, dried over anhydrous magnesium sulfate, filtered, and the filtrate was evaporated. The residue was purified on a silica gel column, eluting with 2:1- to 1:1-hexane:ethyl acetate. The appropriate fractions were collected and evaporated. The residue was recrystallized from ethanol and then 85% ethanol to give 12.8 g (50.9%) of product, mp 82.5°–84° C.

Analysis: Calculated for $C_{28}H_{44}N_2O_4$: 71.15%C 9.38%H 5.93%N Found: 70.86%C 9.18%H 5.82%N

EXAMPLE 16 erythro-N-{1-[6-(1-Dodecynyl)-2-pyridinyl]-1,3-dihydroxy-2-propanyl}acetamide

To a solution of ethyl erythro-2-acetamido-3-[6-(1-dodecynyl)-2-pyridinyl]-3-hydroxypropionate (20.3 g) in dry tetrahydrofuran (250 ml) 2.0M lithium borohydride:tetrahydrofuran (30 ml) was added at 0°, under nitrogen. The reaction mixture was stirred at room temperature overnight. The mixture was chilled and 1:1-methanol:water (100 ml) was added slowly followed by glacial acetic acid (3.5 ml) in 1:1-methanol:water (50 ml) until a pH of 6.5 was obtained. The solution was stirred at room temperature for 2 hrs, the solvents were evaporated, and the residue was azeotroped with methanol (5×100 ml). The residue was slurried with 7.5% sodium bicarbonate solution (65 ml) (pH 8.5), extracted into 3:1-chloroform:2-propanol, and concentrated. The residue was flash chromatographed on silica gel, eluting with 0.5% -methanol:ethyl acetate. The appropriate fractions were collected and evaporated. Recrystallization of the residue from hexane:ethyl acetate/1:1 gave 15.5 g (85.0%) of product, mp 86°–88° C.

Analysis: Calculated for $C_{22}H_{34}N_2O_3$: 70.55%C 9.15%H 7.48%N Found: 70.78%C 9.35%H 7.49%N

EXAMPLE 17

Ethyl erythro-2-acetamido-3-(6-decyl-2-pyridinyl)-3-hydroxypropionate

Ethyl erythro-2-acetamido-3-[6-(1-decynyl)-2-pyridinyl]-3-hydroxypropionate (2.7 g) in ethanol (65 ml) was reduced using 5% palladium-on-charcoal (0.7 g) in a Parr hydrogenator at 40 psi of hydrogen. After 2.5 hrs, the catalyst was collected, the filtrate was evaporated, and the residue was recrystallized from ethyl acetate to give 2.11 g (77.6%) of product, mp 67°–685° C.

Analysis: Calculated for $C_{22}H_{36}N_2O_4$: 67.32%C 9.24%H 7.14%N Found: 66.96%C 9.13%H 7.08%N

EXAMPLE 18 erythro-N-[1-(6-Decyl-2-pyridinyl)-1,3-dihydroxy-2-propanyl]acetamide erythro-N- {1-[6-(1-Decynyl)-2-pyridinyl]-1,3-dihydroxy-2-propanyl}-acetamide (4.0 g) in ethanol (100 ml) was reduced using 5% palladium-on-charcoal (0.1 g) in a Parr hydrogenator at 40 psi of hydrogen. After two hrs, the catalyst was collected, the solvent was evaporated, and the residue was recrystallized from ethyl acetate to give 3.69 g (91%) of product, mp 94°–96° C.

Analysis: Calculated for $C_{20}H_{34}N_2O_3$: 68.54%C 9.78%H 7.99%N Found: 68.36%C 9.72%H 7.94%N

EXAMPLE 19 threo-2-Amino-1-(6-decyl-2-pyridinyl)-1,3-dihydroxypropane threo-N-{1-[6-(1-Decynyl)-2-pyridinyl]-1,3-diacetyloxy-2-propanyl}acetamide (1.0 g) in ethanol (55 ml) was reduced using 5% palladium-on-charcoal (0.06 g) in a Parr hydrogenator at 40 psi of hydrogen. After two hrs, the catalyst was collected, and the solvent was evaporated to give 0.95 g (94%) of threo-N-[3-(6-decyl-2-pyridinyl)-1,3-diacetyloxy-2-propanyl]acetamide.

The acetamide (0.95 g), hydrazine hydrate (40 ml), and ethanol (20 ml) was heated under reflux for 25 hrs., under nitrogen. The reaction mixture was cooled, water (30 ml) was added, and the mixture was extracted with ethyl acetate. The ethyl acetate layer was washed with saturated sodium chloride solution, dried over anhydrous magnesium sulfate, filtered, and the filtrate was evaporated. The residue was chromatographed on silica gel eluting with 980:20:2- to 970:30:2-trichloromethane:methanol:2N ammonium hydroxide. The appropriate fractions were collected and evaporated. The residue was dissolved in ethyl acetate, washed with half-saturated sodium chloride solution, dried, filtered, and the filtrate was evaporated to give 0.50 g (72%) of product, mp 76°–78° C.

Analysis: Calculated for $C_{18}H_{32}N_2O_2$: 70.09%C 10.46%H 9.08%N Found: 70.02%C 10.63%H 8.85%N

EXAMPLE 20 erythro-2-Amino-1-(6-decyl-2-pyridinyl)-1,3-dihydroxypropane erythro-N-[1-(6-Decyl-2-pyridinyl)-1,3-dihydroxy-2-propanyl]acetamide (6.0 g), hydrazine hydrate (60 ml), and ethanol (15 ml) were refluxed for 20 hrs., under nitrogen. The reaction mixture was cooled, water (75 ml) was added, and the mixture was extracted with ethyl acetate. The ethyl acetate layers were washed with saturated sodium chloride solution, dried over anhydrous magnesium sulfate, filtered, and the filtrate was evaporated. The residue was combined with 1.44 g from two other experiments, and was chromatographed on silica gel eluting with 950:50:3- to 900:100:5-trichloromethane:methanol:2N ammonium hydroxide. The appropriate fractions were collected and evaporated. The residue was dissolved in ethyl acetate (150 ml) and the solution was washed with half-saturated sodium chloride solution, dried over anhydrous magnesium sulfate, filtered, and the filtrate was evaporated to give 5.60 g (79%) of product, mp 52°–55° C.

Analysis: Calculated for $C_{18}H_{32}N_2O_2$: 70.09%C 10.46%H 9.08%N Found: 69.63%C 10.29%H 8.87%N

EXAMPLE 21

Ethyl erythro-2-acetamido-3-(6-dodecyl-2-pyridinyl)-3-hydroxypropionate

Ethyl erythro-2-acetamido-3-[6-(1-dodecynyl)-2-pyridinyl]-3-hydroxypropionate (2.0 g) in ethanol (80 ml) containing of 5% palladium-on-carbon (0.06 g) was reduced in a Parr hydrogenator at 40 psi of hydrogen. After two hrs, the catalyst was filtered, the filtrate was evaporated, and the residue was recrystallized from ethyl acetate to give 1.42 g (70.3%) of product, mp 71°–73° C.

Analysis: Calculated for $C_{24}H_{40}N_2O_4$: 68.54%C 9.59%H 6.66%N Found: 68.74%C 9.46%H 6.69%N

EXAMPLE 22 erythro-N-[1-(6-Dodecyl-2-pyridinyl)-1,3-dihydroxy-2-propanyl]acetamide erythro-N-{1-[6-(1-Dodecynyl)-2-pyridinyl]-1,3-dihydroxy-2-propanyl}acetamide (6.05 g) in ethanol (120 ml) containing 5% palladium-on-carbon (0.15 g) was reduced in a Parr hydrogenator at 30 psi of hydrogen. After two hrs, the catalyst was filtered, the filtrate was evaporated, and the residue was recrystallized from ethyl acetate to give 5.90 g (96.4%) of product, mp 99°–100.5° C.

Analysis: Calculated for $C_{22}H_{38}N_2O_3$: 69.80%C 10.12%H 7.40%N Found: 69.71%C 10.37%H 7.34%N

EXAMPLE 23 erythro-2-Amino-1-(6-dodecyl-2-pyridinyl)-1,3-propanediol erythro-N-[1-(6-Dodecyl-2-pyridinyl)-1,3-dihydroxy-2-propanyl]acetamide (3.8 g), hydrazine hydrate (35 ml), and ethanol (20 ml) were refluxed under nitrogen for 24 hrs. The reaction mixture was cooled, water (50 ml) was added, and the mixture was extracted with chloroform (3×65 ml). The extracts were washed with saturated sodium chloride solution, dried over anhydrous magnesium sulfate, filtered, and the filtrate was evaporated. The residue was chromatographed on silica gel, eluting with 950:50:3-chloroform:methanol:2N ammonium hydroxide. The residue was dissolved in ethyl acetate and the solution was washed with half-saturated sodium chloride solution, dried over anhydrous magnesium sulfate, filtered, and the filtrate was evaporated to give 2.10 g (62%) of product, mp 61°–64° C.

Analysis: Calculated for $C_{20}H_{36}N_2O_2$: 71.38%C 10.78%H 8.32%N Found: 71.04%C 10.95%H 8.07%N

EXAMPLE 24 erythro-N-[1-(6-Hexyl-2-pyridinyl)-1,3-dihydroxy-2-propanyl]acetamide erythro-N-{1-[6-(1-Hexynyl)-2-pyridinyl]-1,3-dihydroxy-2-propanyl}acetamide (5.80 g) in ethanol (125 ml) was hydrogenated using 0.15 g of 5% palladium-on-carbon in a Parr system at 40 psi. After 2.5 hours, the catalyst was collected, the filtrate was evaporated, and the residue was recrystallized from ethyl acetate to give 5.2 g (88.6%) of product, mp 75°–76.5° C.

Analysis: Calculated for $C_{16}H_{26}N_2O_3$: 65.28%C 8.90%H 9.52%N Found: 65.18%C 8.78%H 9.50%N

EXAMPLE 25

N,O,O-Tribenzyloxycarbonyl-erythro-2-amino-1-(6-decyl-2-pyridin yl)-1,3-propanediol erythro-2-Amino-1-(6-decyl-2-pyridinyl)-1,3-propanediol (1.50 g), N-benzyloxycarbonyloxysuccinimide (4.00 g) and triethylamine (2.23 ml) in dry tetrahydrofuran (60 ml) was stirred for 9 days, under nitrogen. Additonal N-benzyloxycarbonyloxysuccinimide (4.00 g) was added and stirring was continued for 3 days. The reaction mixture was evaporated. The residue was dissolved in ethyl acetate and the solution was washed with saturated sodium chloride solution, dried over anhydrous magnesium sulfate, filtered, and the filtrate was evaporated. The residue was purified by flash chromatography (silica gel, 9:1 hexane:ethyl acetate). The appropriate fractions were collected and evaporated to give 1.87 g (54%) of product.

Analysis: Calculated for $C_{42}H_{50}N_2O_8$: 70.96%C 7.09%H 3.94%N Found: 71.00%C 6.92%H 3.77%N

EXAMPLE 26

Ethyl erythro-2-acetamido-3-hydroxy-3-[3-(1-undecynyl)phenyl]propionate

To a solution of 3-bromobenzaldehyde (30.3 g) and 1-undecyne (29.5 g) in triethylamine (120 ml) was added bis(triphenylphosphine)palladium(II) chloride (1.9 g) followed by copper(I) iodide (0.25 g). The mixture was stirred in the dark at 55° C. for 6 hrs, under nitrogen. After cooling to room temperature, the reaction mixture was diluted with ethyl acetate and filtered. The filtrate was washed with water and saturated sodium chloride solution, dried over anhydrous magnesium sulfate, filtered, and the filtrate was concentrated to yield 45.8 g of 3-(1-undecynyl)benzaldehyde, as an oil.

A solution of 3-(1-undecynyl)benzaldehyde (23.0 g), acetamidomalonic acid monoethyl ester (15.1 g), and triethylamine (11.2 ml) in dry tetrahydrofuran (150 ml) was stirred at room temperature for 48 hrs, under nitrogen. Additional acetamidomalonic acid monoethyl ester (7.6 g) and triethylamine (5.6 ml) were added and stirring was continued for 72 hrs. The reaction mixture was evaporated and the residue was purified on a silica gel column, eluting with 2:1-hexane:ethyl acetate to give 13.0 g (41%) of product. The product was dissolved in warm 3:2-ethanol:water and cooled. The precipitate was collected. The filtrate was concentrated and the residue was recrystallized from cyclohexane to give the analytical sample, mp 69°–71° C.

Analysis: Calculated for $C_{24}H_{35}NO_4$: 71.79%C 8.79%H 3.49%N Found: 71.81%C 8.72%H 3.51%N

EXAMPLE 27

Ethyl erythro-2-acetamido-3-[3-(1-dodecynyl)phenyl]-3-hydroxypropionate

To a solution of 3-bromobenzaldehyde (26.5 g) and (25.0 g) 1-dodecyne in triethylamine (105 ml) was added bis-(triphenylphosphine)palladium(II) chloride (1.73 g) followed by copper(I) iodide (0.24 g). The resultant mixture was stirred in the dark at 55° C. for 7 hrs, under nitrogen. After cooling to room temperature, the reaction mixture was diluted with ethyl acetate and filtered. The filtrate was washed with water and saturated sodium chloride solution, dried over anhydrous magnesium sulfate, filtered, and concentrated to yield 37.7 g 3-(1-dodecynyl)benzaldehyde. The filtrate was an oil.

A solution of 3-(1-dodecynyl)benzaldehyde (7.6 g), acetamidomalonic acid monoethyl ester (5.1 g), and triethylamine (3.8 ml) in dry tetrahydrofuran (35 ml) was stirred at room temperature for 48 hrs, under nitrogen. Additional acetamidomalonic acid monoethyl ester (2.6 g) and triethylamine (1.9 ml) were added and stirring for 72 hr. The mixture was evaporated, and the residue was purified on a silica gel column, eluting with 2:1-hexane:ethyl acetate to give 4.8 g (43%) of product. The product was dissolved in warm 3:2-ethanol:water and cooled. The precipitate was collected.

The filtrate was concentrated and the residue was recrystallized from 1:2-ethyl acetate:hexane to provide the analytical sample, mp 80°–82° C.

Analysis: Calculated for $C_{25}H_{37}NO_4$: 72.26%C 8.97%H 3.37%N Found: 72.34%C 8.74%H 3.38%N

EXAMPLE 28 cis-erythro-N-{1-[6-(1-Dodecenyl)-2-pyridinyl]-1,3-dihydroxy-2-propanyl}acetamide erythro-N-{1-[6-(1-Dodecynyl)-2-pyridinyl]-1,3-dihydroxy-2-propanyl}acetamide (2.05 g) in ethanol (55 ml), 5% palladium-on-barium sulfate (0.02 g), and 0.04 g of quinoline was hydrogenated at atmospheric pressure until one equivalent of hydrogen (ca. 123 ml) was taken up. The catalyst was filtered, the filtrate was evaporated, and the residue (2.1 g) was combined with residue (3.5 g) from similar reactions. The combined residues were chromatographed on silica gel eluting with 1:2- to 1:4-hexane:ethyl acetate to give 1.58 g (28%) of product, mp 96°–98° C.

Analysis: Calculated for $C_{22}H_{36}N_2O_3$: 70.18%C 9.64%H 7.44%N Found: 70.17%C 9.67%H 7.43%N

EXAMPLE 29

5-(1-Dodecynyl)-2-thiophenecarboxaldehyde

A solution of 1-dodecyne (28.7 g), 5-bromo-2-thiophenecarboxaldehyde (30.0 g) and triethylamine (47.7 g) in dry tetrahydrofuran (75 ml) was degassed and stirred at room temperature under a nitrogen atmosphere. bis(Triphenylphosphine)palladium(II)chloride (two mole percent) followed by copper(I)iodide (one mole percent) was added to the mixture. The mixture was degassed again and stirred at room temperature for three hrs, under nitrogen. The precipitate was collected and washed with ethyl acetate, and the filtrate was evaporated. The residue was distilled in a kugelrohr (oven temp=175° C./0.1 mm Hg) to give 27.1 g (62%) of product, as a oil. A portion of the oil was purified by flash chromatography (silica; 7:3-hexane-dichloromethane) and dried at 50° C. under vacuum for three hrs to give the analytical sample Analysis: Calculated for $C_{17}H_{24}OS$: 73.86%C 8.75%H Found: 73.86%C 8.72%H

EXAMPLE 30

Ethyl erythro-2-acetamido-3-[5-(1-dodecynyl)-2-thienyl]-3-hydroxypropionate

A slurry of 5-dodecynyl-2-thiophenecarboxaldehyde (31.8 g), acetamidomalonic acid monoethyl ester (21.7 g), and dry tetrahydrofuran (150 ml) was degassed and cooled to 0° C. Triethylamine (5% excess) was added, the solution was degassed, and the reaction mixture was stirred at room temperature for 2 days, under nitrogen. Additional acetamidomalonic acid monoethyl ester (21.7 g) and triethylamine (5% excess) were added, and the reaction mixture was stirred at room temperature for 5 days, under nitrogen. The mixture was evaporated, and the residue was purified by flash chromatography (silica, 1:1-ethyl acetate:hexanes). The appropriate fractions were collected and evaporated. The residue was recrystallized from ether and from ethyl acetate-hexane to give 29.5 g(61%) of product, mp 81°–83° C.

Analysis: Calculated for $C_{23}H_{35}NO_4S$: 65.53%C 8.37%H 3.32%N Found: 65.36%C 8.25%H 3.30%N

EXAMPLE 31 erythro-N-[1-[5-(1-dodecynyl)-2-thienyl]-1,3-dihydroxy-2-propanyl]acetamide

A solution of ethyl erythro-2-acetamido-3-[5-(1-dodecynyl)-2-thienyl]-3-hydroxypropionate (15.0 g) in dry tetrahydrofuran (150 ml) was stirred at 0° C., under nitrogen, as 2M lithium borohydride in tetrahydrofuran (22.3 ml) was added dropwise. The reaction mixture was stirred at room temperature for 3 days, under nitrogen. The pH of the mixture was adjusted to 6 with glacial acetic acid, and the mixture was evaporated. The residue was diluted with water (100 ml) and extracted with ethyl acetate. The combined organic extracts were dried over anhydrous magnesium sulfate, filtered, and the filtrate was evaporated. The residue was purified by flash chromatography (silica, 1–5% methanol-ethyl acetate). The appropriate fractions were collected and evaporated. The residue was recrystallized from ethyl acetate-hexane to give 9.6 g (71%) of product, mp 83°–85° C.

Analysis: Calculated for $C_{21}H_{33}NO_3S$: 66.45%C 8.76%H 3.69%N Found: 66.47%C 8.53%H 3.75%N

EXAMPLE 32 erythro-2-Amino-1-[5-(1-dodecynyl)-2-thienyl]-1,3-propanediol

A solution of erythro-N-[1-[5-(1-dodecynyl)-2-thienyl]-1,3-dihydroxy-2-propanyl]acetamide (3.00 g), 2N sodium hydroxide solution (100 ml) and 95% ethanol (50 ml) was stirred at 65° C. overnight. After cooling to room temperature, the mixture was evaporated, and the residue was diluted with sodium bicarbonate solution (250 ml). The mixture was extracted with 3:1-chloroform:isopropanol and the combined organic layers were dried anhydrous sodium sulfate, filtered, and the filtrate was evaporated. The residue was purified by flash chromatography (silica gel, 90:9:1-dichloromethane: methanol:ammonium hydroxide). The appropriate fractions were collected and evaporated. The residue was crystallized from ethyl acetate:hexane to give 1.4 g (53%) of product, mp 77°–78° C.

Analysis: Calculated for $C_{19}H_{31}NO_2S$: 67.61%C 9.26%H 4.15%N Found: 67.61%C 8.63%H 4.16%N cl EXAMPLE 33 erythro-N-[1-[5-(1- Dodecyl)-2-thienyl]-1,3-dihydroxy-2-propanyl]acetamide

A mixture of erythro-N-[1-[5-(1-dodecynyl)-2-thienyl]-1,3-dihydroxy-2-propyl]acetamide (8.00 g), 5% palladium-on-carbon (400 mg), and absolute ethanol (500 ml) was shaken on a Parr hydrogenator under 50 psi of hydrogen for three hrs. The catalyst was collected. Fresh catalyst (400 mg) was added to the filtrate and the mixture was shaken under 50 psi of hydrogen overnight. The mixture was filtered through a bed of celite, and the filter cake washed with ethanol. The filtrate was evaporated, and the residue was recrystallized from ethyl acetate to give 7.3 g (90%) of product, m.p. 104°–106° C.

Analysis: Calculated for $C_{21}H_{37}NO_3S$: 65.75%C 9.72%H 3.65%N Found: 65.45%C 9.58%H 3.67%N

EXAMPLE 34 erythro-2-Amino-1-[5-(1-dodecyl)-2-thienyl]-1,3-propanediol

A solution of erythro-N-[3-[5-(1-dodecyl)-2-thienyl]-1,3-dihydroxy-2-propyl]acetamide (3.00 g), hydrazine monohydrate (35 ml) and absolute ethanol (25 ml) was stirred at 70° C. for 48 hrs, under nitrogen. The reaction mixture was cooled to room temperature, poured into 300 ml of dilute sodium bicarbonate solution (300 ml), and extracted with chloroform. The combined organic layers were dried over anhydrous sodium sulfate, filtered, and the filtrate was evaporated. The residue was purified by flash chromatography (silica; 90:9:1-dichloromethane:methanol:ammonium hydroxide). The appropriate fractions were collected and evaporated. The residue was recrystallized from ethyl acetate:hexane to give 1.4 g (52%) of product, m.p.89°–90° C.

Analysis: Calculated for $C_{19}H_{35}NO_2S$: 66.81%C 10.33%H 4.10%N Found: 66.48%C 10.37%H 4.11%N

EXAMPLE 35

Ethyl erythro-2-acetamido-3-(3-dodecyl-5-isoxazolyl)-3-hydroxypropionate

A mixture of 3-dodecyl-5-isoxazolecarboxaldehyde (5.72 g) and acetaminomalonic acid monoethylester (4.06 g) in dry tetrahydrofuran (75 ml) was cooled to 0°, with stirring, and triethylamine (2.29 g) was added. The reaction mixture was allowed to warm to room temperature and was stirred for 16 hrs. The solution was evaporated and the residue was purified by flash chromatography (silica gel, 2:1-ethyl acetate:hexanes). The appropriate fractions were collected and evaporated. Recrystallization of the residue from ethyl acetate:hexane gave 4.65 g (52.6%) of product, mp 87°–89° C.

Analysis: Calculated for $C_{22}H_{38}N_2O_5$: 64.36%C 9.33%H 6.82%N Found: 64.55%C 9.08%H 6.76%N

EXAMPLE 36 erythro-N-[1-[3-(1-Dodecyl)-5-isoxazolyl]-1,3-dihydroxy-2-propyl]acetamide.

To a solution of freshly prepared calcium borohydride (0.61 g) (from calcium hydride and borane-dimethyl sulfide) in dry tetrahydrofuran (70 ml) was added a solution of ethyl erythro-2-acetamido-3-(3-dodecyl-5-isoxazolyl)-3-hydroxypropionate (2.4 g) in dry tetrahydrofuran (20 ml). The reaction mixture was stirred at room temperature for 3 hrs. The reaction was quenched with 90:10:5-mixture of water, methanol, acetic acid, and extracted with chloroform. The solution was evaporated and the residue was recrystallized twice from ethyl acetate-hexane to give 1.23 g (57.1%) of product, mp 88°–90° C.

Analysis: Calculated for $C_{20}H_{36}N_2O_4$: 65.19%C 9.85%H 7.60%N Found: 65.17%C 9.60%H 7.60%N

EXAMPLE 37

Ethyl erythro-2-acetamido-3-(6-bromo-2-pyridinyl)-3-hydroxypropionate

A solution of 6-bromo-2-pyridinecarboxaldehyde (5.6 g), acetamidomalonic acid monoethyl ester (5.67 g), and triethylamine (4.2 ml) in dry tetrahydrofuran (40 ml) was stirred at room temperature overnight, under nitrogen. The reaction mixture was evaporated and the mixture was purified on a silica gel column, eluting with 1:1-hexane:ethyl acetate to give 7.9 g (80%)of product as a mixture of two diastereomers. Recrystallization from toluene, followed by ethyl acetate gave 2.15 g (21.6%) of the erythro product, mp 98°–100° C.

Analysis: Calculated for $C_{12}H_{15}BrN_2O_4$: 43.52%C 4.57%H 8.46%N Found: 43.56%C 4.53%H 8.42%N

EXAMPLE 38 erythro-N-[1-(6-Bromo-2-pyridinyl)-1,3-dihydroxy-2-propanyl]acetamide

To a 2:1-erythro:threo mixture of ethyl 2-acetamido-3-(6-bromo-2-pyridinyl)-3-hydroxypropionate (11.4 g) in dry tetrahydrofuran (60 ml) was added slowly 2.0M lithium borohydride tetrahydrofuran (20.6 ml) at 0°, under nitrogen, and the mixture was stirred at room temperature overnight. The reaction mixture was chilled, and 1:1-methanol:water (100 ml) was added slowly followed by glacial acetic acid (2 ml) until pH 6.5 was obtained. The mixture was evaporated and the residue azeotroped with methanol (6×50 ml). The residue was slurried with 7.5% sodium bicarbonate solution (40 ml) (pH 8.5), extracted with 3:1-trichloromethane:isopropanol, filtered, and the filtrate was concentrated. The residue was flash chromatographed on silica gel eluting with 19:1-ethyl acetate:methanol to give 8.9 (93.7%) of product. Recrystallization from ethanol gave the analytical sample of the erythro-diastereomer, mp 134.5°–136.5° C.

Analysis: Calculated for $C_{10}H_{13}BrN_2O_3$: 41.54%C 4.53%H 9.69%N Found: 41.64%C 4.54%H 9.64%N

EXAMPLE 39

6-(1-Hexadecynyl)-2-pyridinecarboxaldehyde

A solution of 6-bromo-2-pyridinecarboxaldehyde (12.3 g), 1-hexadecyne (16.1 g), triethylamine (20.0 g), bis(triphenylphosphine)palladium(II)chloride (0.92 g), and copper(I)iodide (0.13 g) in dry tetrahydrofuran (55 ml) was heated at 50° C. for 29 hrs, under nitrogen. The reaction mixture was cooled to room temperature, filtered, and the filter cake was washed with ethyl acetate. The filtrate was evaporated and the residue was taken up in ethyl acetate (100 ml). The mixture was washed with 1:1 -water:saturated sodium chloride solution, dried over anhydrous magnesium sulfate, filtered, and the filtrate was evaporated. The residue was flash chromatographed on silica gel, eluting with 1% ethyl acetate:hexanes. The appropriate fractions were collected and evaporated. The residue was dissolved in ethyl acetate and the solution was washed with half-saturated sodium chloride solution, dried over anhydrous magnesium sulfate, filtered, and the filtrate was evaporated to give 11.5 g (53.5%) of product, mp 38.5°–40° C.

Analysis: Calculated for $C_{22}H_{33}NO$: 80.68%C 10.16%H 4.28%N Found: 80.44%C 10.00%H 4.30%N

EXAMPLE 40

3-(1-Dodecyl)-5-isoxazolemethanol

To a solution of 1-nitrotridecane (10.5 g) and O-trimethylsilyl-propynol (5.88 g) in dry benzene (100 ml) was added dropwise a solution of freshly distilled phenylisocyanate (10.9 g) and triethylamine (5.56 g) in dry benzene (40 ml) at 40° C., with mechanical stirring. The mixture was heated to 60° C. for 3.5 hr, cooled, and filtered. The filtrate was evaporated, taken up in tetrahydrofuran (300 ml) and 1.0M tetrabutylammonium fluoride (8 ml) was added. After 30 mins, the mixture was evaporated and the residue was purified by flash chromatography (silica gel, 2% methanol:dichloromethane). The appropriate fractions were collected and evaporated to give 10.5 g (86%) of product, mp 61°–63° C.

Analysis: Calculated for $C_{16}H_{29}NO_2$: 71.87%C 10.93%H 5.24%N Found: 71.92%C 11.10%H 5.19%N

EXAMPLE 41

3-(1-Dodecyl)-5-isoxazolecarboxaldehyde

A solution of oxalyl chloride (28.8 ml) in dry dichloromethane (100 ml) was cooled to −60° C. and a solution of dimethylsulfoxide (8.9 ml) in dichloromethane (30 ml) was added, followed by a slurry of 3-(1-dodecyl)-5-isoxazolemethanol (14.0 g) in dry dichloromethane (200 ml). The mixture was stirred at −60° C. for 1 hr, quenched with triethylamine (87 ml) and allowed to warm to room temperature. The solution was poured into water (300 ml) and extracted with dichloromethane. The organic phases were washed with dilute citric acid solution, dried, filtered, and the filtrate was evaporated. The residue was passed through a short pad of silica gel using dichloromethane as the eluent. The solution was evaporated and the residue was recrystallized from ether-hexane to give 11.5 g (78%) of product, mp 53°–54° C.

Analysis: Calculated for $C_{16}H_{27}NO_2$: 72.41%C 10.25%H 5.28%N Found: 72.22%C 10.59%H 5.24%N

EXAMPLE 42 erythro-N-{1-[6-(1-Hexadecynyl)-2-pyridinyl]-1,3-dihydroxy-2-propanyl}acetamide

To ethyl erythro-2-acetamido-3-{6-(1-hexadecynyl)2-pyridinyl]-3-hydroxypropionate (11.1 g), in tetrahydrofuran (100 ml) dry was added slowly 2.0M lithium borohydride tetrahydrofuran (11.8 ml) at 0° under nitrogen. The reaction mixture was stirred at ambient temperature for 2.5 hrs, chilled, and 1:1-methanol:water (60 ml) and glacial acetaic acid (1.4 ml) was added slowly until a pH of 6.5 was obtained. The mixture was then stirred at ambient temperature for 0.5 hr and evaporated. The residue was azeotroped with methanol (4×40 ml), slurried with 7.5% sodium bicarbonate solution (25 ml) (pH 8.5), and the mixture was extracted with 3: 1-chloroform:2-propanol. The solution was concentrated and the residue was flash chromatographed on silica gel, eluting with 99:1-ethyl acetate:methanol. The appropriate fractions were collected and evaporated. Recrystallization gave 8.57 g (84.4%) of product, mp 88°–90° C.

Analysis: Calculated for $C_{26}H_{42}N_2O_3$: 72.52%C 9.83%H 6.51%N Found: 72.55%C 9.46%H 6.54%N

EXAMPLE 43 erythro-N-[1,3-Diacetyloxy-1-(6-hexadecyl-2-pyridinyl)-2-propanyl]acetamide

A mixture of N-{1-[6-(1-hexadecynyl)-2-pyridinyl]-1,3-dihydroxy-2-propanyl}acetamide. (7.26 g, 5:2-erythro:threo mixture), acetic anhydride (10.5 g), triethylamine (15.5 g), and 4-dimethylaminopyridine (0.21 g), in tetrahydrofuran (100 ml) was stirred at ambient temperature overnight. The reaction mixture was evaporated, methanol was added, and the mixture was warmed at 50° C. for 20 min, and then was concentrated. A solution of 7.5% sodium bicarbonate solution was added to the residue until a pH of 8.5 was obtained. The mixture was extracted with chloroform. The organic extract was dried over anhydrous magnesium sulfate, filtered and the filtrate was concentrated. The residue was flash chromatographed, eluting with 2:1 to 1:1-hexane:ethyl acetate. The appropriate fractions were collected and evaporated to yield 5.54 g (64%) of erythro-N-[1,3-diacetyloxy-1-(6-hexadecynyl-2-pyridinyl)-2-propanyl]acetamide.

A mixture of erythro-N-[1,3-diacetyloxy-1-(6-hexadecynyl-2-pyridinyl-2-propanyl]acetamide (5.4 g) in ethanol (150 ml) and 5% palladium-on-carbon (0.20 g) was shaken on a Parr hydrogenator under 35 psi of hydrogen for 2.5 hrs. The catalyst was collected and the filtrate was evaporated. The residue was chromatographed to give 4.1 g (75%; 48% overall) of product, mp 79°–80.5° C.

Analysis Calculated for $C_{30}H_{50}N_2O_5$: 69.46%C 9.72%H 5.40%N Found: 69.81%C 9.60%H 5.41%N

EXAMPLE 44 erythro-N-[1-(6-Hexadecyl-2-pyridinyl)-1,3-dihydroxy-2-propanyl]acetamide

A mixture of erythro-N-{1-[6-(1-hexadecynyl)-2-pyridinyl]-1,3-dihydroxy-2-propanyl}acetamide (3.9 g), ethanol (125 ml) and 5% palladium-on-carbon (0.20 g) was shaken on a Parr hydrogenator under 35 psi of hydrogen for 2 hrs. The catalyst was collected and the filtrate was evaporated. The residue was recrystallized from ethyl acetate to give 3.6 g (91%) of product, mp 98°–101° C.

Analysis: Calculated for $C_{26}H_{46}N_2O_3$: 71.85%C 10.67%H 6.44%N Found: 71.92%C 10.75%H 6.52%N

EXAMPLE 45 erythro-2-Amino-(6-hexadecyl-2-pyridinyl)-1,3-propanediol erythro-N-[1-(6-hexadecyl-2-pyridinyl)-1,3-dihydroxy-2-propanyl]acetamide (3.0 g), hydrazine hydrate (35 ml), and ethanol (25 ml) were heated under reflux, under nitrogen, for 28 hrs. The reaction mixture was cooled, water (40 ml) was added, and the mixture was extracted with chloroform. The combined extracts were washed with saturated sodium chloride solution, dried over anhydrous magnesium sulfate, filtered, and the filtrate was evaporated. The residue was chromatographed on silica gel, eluting with 950:50:3-chloroform:methanol:2N ammonium hydroxide. The appropriate fractions were collected and concentrated. The residue was dissolved in ethyl acetate and the solution was washed with half-saturated sodium chloride solution, dried, over anhydrous magnesium sulfate, filtered, and the filtrate was evaporated. The residue was azeotroped with toluene to give 1.37 g (50%) of product, mp 67°–69° C.

Analysis: Calculated for $C_{24}H_{44}N_2O_2$: 73.42%C 11.30%H 7.13%N Found: 73.25%C 11.14%H 7.04%N

EXAMPLE 46

Ethyl threo-2-acetamido-3-(6-bromo-2-pyridinyl)-3-hydroxypropionate

A solution of 6-bromo-2-pyridinecarboxaldehyde (30.3 g), acetamidomalonic acid monoethyl ester (34.1 g), and triethylamine (16.6 g) in dry tetrahydrofuran (170 ml) was stirred under nitrogen at ambient temperature overnight. The reaction mixture was concentrated and the residue was azeotroped three times with ethyl acetate, and then recrystallized from ethyl acetate to remove 36.4 g of ethyl erythro-2-acetamido-3-(6-bromo-2-pyridinyl)-3-hydroxyproprionate. The filtrate was chromatographed on a silica gel column, eluting with 3:2 to 1:1-hexane:ethyl acetate. The appropriate fractions were collected and concentrated. The residue was recrystallized from ethyl acetate to give 1.0 g (2.0%) of product, mp 144°–146° C.

Analysis: Calculated for $C_{12}H_{15}BrN_2O_4$: 43.52%C 4.57%H 8.46%N Found: 44.02%C 4.52%H 8.39%N

EXAMPLE 47

6-(1-Undecynyl)pyridine-2-carboxaldehyde

A solution of 6-bromopyridine-2-caboxaldehyde (15.0 g), 1-undecyne (12.9 g), triethylamine (24.5 g), bis(triphenylphosphine)palladium(II)chloride (1.1 g, 2%), and copper(I)iodide (0.15 g, 1%) in dry tetrahydrofuran (60 ml) was heated under nitrogen at 55° C. for 10 hrs. The reaction mixture was filtered, the filter cake was washed with ethyl acetate, and the filtrate was evaporated. The residue was dissolved in ethyl acetate, and the solution was washed with half-saturated sodium chloride solution, dried over anhydrous magnesium sulfate, filtered, and the filtrate was concentrated. The residue was flash chromatographed on silica gel, eluting with 0%–2%-ethyl acetate:hexane. The appropriate fractions were collected and evaporated to yield 17.5 g (84.0%) of product.

Analysis: Calculated for $C_{17}H_{23}NO$: 79.33%C 9.01%H 5.44%N Found: 79.03%C 9.36%H 5.14%N

EXAMPLE 48

Ethyl erythro-2-acetamido-3-hydroxy-3-[6-(1-undecynyl)-2-pyridinyl]propionate

A mixture of ethyl erythro-2-acetamido-3-(6-bromo-2-pyridinyl)-3-hydroxypropionate (20.8 g), 1-undecyne (11.5 g), triethylamine (12.7 g), bis(triphenylphosphine)palladium chloride (0.88 g), and cuprous iodide (0.12 g) in dry tetrahydrofuran (100 ml) was heated at 55° C. for 4 hrs under nitrogen. Additional 1-undecyne (2.9 g), triethylamine (3.2 g), bis(triphenylphosphine)palladium chloride (0.44 g), and cuprous iodide (0.06 g) were added at ambient temperature, and the reaction mixture was heated an additional 5 hrs. The reaction mixture was evaporated and the residue was dissolved in ethyl acetate. The solution was washed with half-saturated sodium chloride solution and the organic phase was flash chromatographed on silica gel, eluting with 3:2 to 1:1-hexane:ethyl acetate. The appropriate fractions were collected and evaporated. Recrystallization of the residue from ethyl acetate save 16.0 g (63.4%) of product, mp 92°–93° C.

Analysis: Calculated for $C_{23}H_{34}N_2O_4$: 68.63%C 8.51%H 6.96%N Found: 68.58%C 8.94%H 6.94%N

EXAMPLE 49 erythro-N-{1,3-Dihydroxy-1-[6-(1-undecynyl)-2-pyridinyl]-2-propanyl}acetamide

To ethyl erythro-2-acetamido-3-hydroxy-3-[6-(-1-undecynyl)-2-pyridinyl]propionate (17.9 g), in dry tetrahydrofuran (150 ml) was added 2.0M lithium borohydride/tetrahydrofuran (22 ml) at 0° C. under nitrogen. The reaction mixture was chilled, stirred at ambient temperature overnight, and 1:1-methanol:water (30 ml) was added followed by of glacial acetic acid (2.8 ml) in 1:1-methanol:water (30 ml) until a pH of 6.4 was obtained. The solution was stirred at ambient temperature for 1 hr, evaporated, and the residue was azeotroped with methanol. The residue was slurried with 75% sodium bicarbonate solution (pH 8.5), extracted with 3:1-chloroform:2-propanol, and concentrated. The residue was flash chromatographed on silica gel, eluting with 0.5%–1% methanol:ethyl acetate. The appropriate fractions were collected and concentrated. The residue was recrystallized from 1:1-hexane:ethyl acetate to give 12.1 g (75.4%) of product, mp 95°–96.5° C.

Analysis: Calculated for $C_{21}H_{32}N_2O_3$: 69.97%C 8.95%H 7.77%N Found: 69.84%C 8.87%H 7.71%N

EXAMPLE 50

(Z)-erythro-N-{1,3-Dihydroxy-1-{6-(1-octenyl)-2-pyridinyl]-2-propanyl}acetamide

A solution of ethyl erythro-2-acetamido-3-[6-(1-octynyl)-2-pyridinyl]-3-hydroxypropionate (9.0 g), in dry tetrahydrofuran (80 ml) and 2.0M lithium borohydride tetrahydrofuran (12.5 ml), was stirred under nitrogen at 0° C. The reaction mixture was stirred at ambient temperature overnight, chilled, and 1:1-methanol:water (40 ml) and acetic acid (1.5 ml) was added until a pH of 6.8 was obtained. The reaction mixture was stirred 1 hr, evaporated, and the residue was azeotroped with methanol. 7.5% Sodium bicarbonate solution was added until a pH of 8.5 was obtained. The mixture was extracted with 3:1-chloroform:-2-propanol and concentrated. The residue was flash chromatographed on silica gel, eluting with 1% methanol ethyl acetate to give 7.6 g of material.

Part of the above material (5.0 g) and 8.35 g from a similar experiment, acetic anhydride (25.7 g), triethylamine (38.2 g), and 4-dimethylaminopyridine (0.51 g) in tetrahydrofuran (180 ml) was stirred at ambient temperature for 3 hrs. The reaction mixture was evaporated, methanol was added, and the mixture was warmed at 50° C. for 20 min, and evaporated. A 7.5% sodium bicarbonate solution was added until a pH of 8.5 was obtained and the mixture was extracted with chloroform. The extract was dried over anhydrous magnesium sulfate, filtered, and the filtrate was concentrated. The residue was flash chromatographed, eluting with 2:1-hexane:ethyl acetate. The appropriate fractions were collected and concentrated to yield 1.1 g of (Z)-erythro-N-{1,3-diacetyloxy-1[6-(1-octenyl)-2-pyridinyl]-2-propanyl}acetamide.

A solution of (Z)-erythro-N-{1,3-diacetyloxy-1-[6-(1-octenyl)-2-pyridinyl]-2-propanyl}acetamide (1.1 g), potassium carbonate (0.44 g) in methanol (18 ml) was stirred for 1 hr. The reaction mixture was filtered and the filtrate was concentrated. The residue was chromatographed on silica gel, eluting with 0.5% methanol/ethyl acetate. The appropriate fractions were collected and concentrated to give 0.5 g (3.7% overall) of product.

Analysis: Calculated for $C_{18}H_{28}N_2O_3$: 67.47%C 8.81%H 8.74%N Found: 67.60%C 8.96%H 8.72%N

EXAMPLE 51 erythro-N-[1,3-Diacetyloxy-1-(6-octyl-2-pyridinyl)2-propanyl]acetamide

A solution of erythro-N-{1,3-dihydroxy-1-{[6-(1-octynyl)-2-pyridinyl]-2-propanyl}acetamide (13.4 g), acetic anhydride (25.7 g), triethylamine (38.2 g), and 4-dimethylaminopyridine (0.51 g) in tetrahydrofuran (180 ml) was stirred at ambient temperature for 3 hrs. The reaction mixture was evaporated, methanol was added to the residue, and the solution was warmed at 50° C. for 20 min and evaporated. A solution of 7.5% sodium bicarbonate solution was added until a pH of 8.5 was obtained, and the mixture was extracted with chloroform. The extract was dried over anhydrous magnesium sulfate, filtered, and the filtrate was concentrated. The residue was flash chromatographed, eluting with 2:1 to 1:1-hexane:ethyl acetate. The appropriate fractions were collected and evaporated to yield 9.17 g of erythro-N-[1,3-diacetyloxy-1-(6-octynyl-2-pyridinyl)-2-propanyl]acetamide.

A portion of erythro-N-[1,3-diacetyloxy-1-(6-octynyl-2-pyridinyl)-2-propanyl]acetamide (7.5 g) in ethanol (200 ml) and 5% palladium-on-carbon (0.25 g) was shaken on a Parr hydrogenator at 40 psi of hydrogen. After 1.5 hrs, the catalyst was collected and the filtrate was evaporated. The residue was chromatographed to give 6.0 g (78.5%, 43% overall) of product, mp 53°–56° C.

Analysis: Calculated for $C_{22}H_{34}N_2O_5$: 65.00%C 8.43%H 6.89%N Found: 65.07%C 8.32%H 6.88%N

EXAMPLE 52 erythro-N-[1,3-Dihydroxy-1-(6-octyl-2-pyridinyl)-2-propanyl]acetamide.

A solution of erythro-N-[1,3-diacetyloxy-1-(6-octyl-2-pyridinyl-2-propanyl]acetamide (5.2 g), and potassium carbonate (0.88 g) in methanol (75 ml) was stirred for 1 hr. The precipitate was collected, and the filtrate was evaporated. 7.5% Sodium bicarbonate solution and 1N hydrochloric acid was added until a pH of 8.5 was obtained. The mixture was extracted with 3:1-chloroform:2-propanol. The extract was dried over anhydrous magnesium sulfate, filtered, and the filtrate was evaporated. Recrystallization of the residue from ethyl acetate gave 3.1 g (75.6%) of product, mp 85°–86.5° C.

Analysis: Calculated for $C_{18}H_{30}N_2O_3$: 67.05% 9.38%H 8.69%N Found: 66.98%C 9.74%H 8.65%N

EXAMPLE 53 erythro-2-Amino-1-(6-octyl-2-pyridinyl)1,3-propanediol

A solution of erythro-N-[1,3-dihydroxy-1-(6-octyl-2-pyridinyl)-2-propanyl]acetamide. (3.8 g), hydrazine hydrate (35 ml), and ethanol (25 ml) was heated under reflux, under nitrogen, for 26 hrs. The reaction mixture was cooled, water (50 ml) was added, and the mixture was extracted with chloroform. The extract was washed with saturated sodium chloride solution, dried over anhydrous magnesium sulfate, filtered, and the filtrate was evaporated. The residue was chromatographed on silica gel, eluting with 950:50:3-chloroform:methanol:2N ammonium hydroxide. The appropriate fractions were collected and evaporated. The residue was dissolved in ethyl acetate and the solution was washed with half-saturated sodium chloride solution dried over anhydrous magnesium sulfate, filtered, and the filtrate was evaporated. The residue was azeotroped with toluene to give 2.47 g (75%) of product mp 38°–40° C.

Analysis:
Calculated for $C_{16}H_{28}N_2O_2.0.1H_2O$: 68.10%C 10.07%H 9.93%N Found: 67.88%C 10.18%H 9.74%N

EXAMPLE 54 threo-2-Amino-1-(6-octyl-2-pyridinyl)-1,3-propanediol

A mixture of erythro-and threo-N-{1,3-dihydroxy-1-[6-(1-octynyl)-2-pyridiniyl]-2-propanyl}acetamide (13.4 g), acetic anhydride (25.7 g), triethylamine (38.2 g), and 4-dimethylaminopyridine (0.5 g) in tetrahydrofuran (180 ml) was stirred at ambient temperature for 3 hrs. The reaction mixture was evaporated, the residue was warmed with methanol (80 ml) for 20 min, and the mixture was evaporated. 7.5% Sodium bicarbonate solution was added to a pH of 8.5, and the solution extracted with chloroform. The extracts were dried, filtered, and the filtrate was evaporated. The residue was flash chromatographed. The appropriate fractions collected and evaporated to yield 2.4 g (14%) of threo-N-{1,3-diacetyloxy-1-[6-(1-octynyl)-2-pyridinyl]-2-propanyl}acetamide.

threo-N-{1,3-Diacetyloxy-1-[6-(1-octynyl)-2-pyridinyl]-2-propanyl}acetamide (2.4 g) in ethanol (75 ml) containing 0.12 g of 5% palladium-on-carbon was shaken on a Parr hydrogenator at 40 psi of hydrogen. After 3 hrs, the reaction mixture was filtered, and the filtrate was evaporated. The residue was flash chromatographed. The appropriate fractions were collected and evaporated to give 2.2 g (92%)of threo-N-[1,3-diacetyloxy-1-(6-octyl-2-pyridinyl)-2-propanyl]acetamide.

A solution of threo-N-{1,3-diacetyloxy-1-[6-(1-octyl)-2-pyridinyl]-2-propanyl}acetamide (2.17 g) was stirred with potassium carbonate (70 mg), and methanol (25 ml) was stirred for 1 hr at ambient temperature, filtered, and the filtrate was evaporated. Water was added, the pH was adjusted to 8.5, and the mixture was extracted with 3:1-chloroform:i-2-propanol. The extract was concentrated to give 1.6 g (94%) of threo-N-[1,3-diacetyloxy-1-(6-octyl-2-pyridinyl)-2-propanyl]acetamide, mp 71.5°–74° C.

A solution of threo-N-[1,3-diacetyloxy-1-(6-octyl-2-pyridinyl)-2-propanyl]acetamide (1.6 g), hydrazine hydrate (15 ml), and ethanol (15 ml) was heated winder reflux, under nitrogen for 23 hrs. The reaction mixture was cooled, water was added, and the mixture was extracted with chloroform. The extracts were washed with saturated sodium chloride solution, dried over anhydrous magnesium sulfate, filtered, and the filtrate was evaporated. The residue was chromatographed on silica gel, eluting with 960:40:3-chloroform:methanol:2N ammonium hydroxide. The appropriate fractions were collected and evaporated to give 0.78 g (56.5%, 7.0% overall) of product, mp 74°–77° C.

Analysis: Calculated for $C_{16}H_{28}N_2O_2$: 68.53%C 10.06%H 9.99%N Found: 68.48%C 10.15%H 9.96%N

EXAMPLE 55 erythro-2-Amino-1-(6-hexyl-2-pyridinyl)-1,3-propanediol

A solution of erythro-2-[1-(6-hexyl-2-pyridinyl)-1,3-dihydroxy-2-propanyl]acetamide (3.6 g), hydrazine hydrate (35 ml) and ethanol (25 ml) was heated under reflux, under nitrogen for 29 hrs. The reaction mixture was cooled, water (50 ml) was added, and the mixture was extracted with ethyl acetate. The extract was washed with saturated sodium chloride solution, dried over anhydrous magnesium sulfate, filtered and the filtrate was evaporated. The residue was chromatographed on silica gel, eluting with 950:50:3-chloroform:methanol:2N ammonium hydroxide. The appropriate fractions were collected and evaporated. The residue was dissolved in ethyl acetate (80 ml), and the solution was washed with half-saturated sodium chloride solution, dried, filtered, and the filtrate was evaporated to give 2.02 g, (66%) of product.

Analysis: Calculated for $C_{14}H_{24}N_2O_2$: 66.63%C 9.59%H 11.10%N Found: 65.91%C 9.42%H 10.82%N

EXAMPLE 56

6-(7-Phenyl-1-heptynyl)pyridine-2-carboxaldehyde

A solution of 6-bromopyridine-2-caboxaldehyde (30.0 g), 7-phenyl-1-heptyne (26.8 g), triethylamine (48.9 g), bis-(triphenylphosphine)palladium(II)chloride (2.3 g, 2%), and copper(I)iodide (0.31 g, 1%) in dry tetrahydrofuran (100 ml) was heated under nitrogen at 55° C. for 70 hrs. The reaction mixture was cooled to ambient temperature, filtered, and the filtrate was washed with ethyl acetate. The filtrate was evaporated. The residue was dissolved in ethyl acetate, the solution washed with half-saturated sodium chloride solution, dried over anhydrous magnesium sulfate, and the filtrate was concentrated. The residue was flash chromatographed on silica gel, eluting with 0.5% to 2%-ethyl acetate-:hexane. The appropriate fractions were collected and concentrated to yield 29.5 g of the product.

Analysis: Calculated for $C_{19}H_{19}NO$: 82.28%C 6.90%H 5.05%N Found: 82.00%C 6.94%H 5.02%N

EXAMPLE 57

Ethyl erythro-2-acetamido-3-hydroxy-3-[6-(7-phenyl-1-heptynyl)-2-pyridinyl]propionate A solution of 6-(7-phenyl-1-heptynyl)pyridine-2-carboxaldehyde (26.5 g), acetamidomalonic acid monoethyl ester (19.2 g), triethylamine (14.6 ml) in dry tetrahydrofuran (125 ml) was stirred at ambient temperature for 3 days, under nitrogen. The reaction mixture was evaporated, the residue was dissolved in ethyl acetate and the solution was washed with half-saturated sodium chloride solution, dried over anhydrous magnesium sulfate, filtered, and evaporated. The residue was chromatographed on a silica gel column, eluting with 1:1-hexane:ethyl acetate to give 32.9 g (82.0%) of a mixture of erythro- and threo-isomers. The mixture was recrystallized from 1:1-hexane:ethyl acetate to give 4.7 g (11.5%) of product, mp 79.0°–81° C.

Analysis: Calculated for $C_{25}H_{30}N_2O_4$: 71.07%C 7.16%H 6.63%N Found: 71.27%C 6.89%H 6.63%N

EXAMPLE 58 erythro-N-{1,3-Dihydroxy-1-[6-(7-phenyl-1-heptynyl)-2-pyridinyl]-2-propanyl}acetamide To a solution of ethyl erythro-2-acetamido-3-hydroxy-3-[6-(7-phenyl-1-heptynyl)-2-pyridinyl]propionate (23.4 g) in dry tetrahydrofuran (200 ml) was added 2.0M lithium borohydride tetrahydrofuran (22 ml) at 0° C. under nitrogen. The reaction mixture was stirred at ambient temperature overnight, chilled, and 1:1-methanol:water (50 ml) was added followed by glacial acetic acid (2.5 ml) in 1:1-methanol:water (30 ml) until a pH of 6.4 was obtained. The solution was stirred at ambient temperature for 1 hr, evaporated, and the residue was azeotroped with methanol. The residue was slurried with sodium bicarbonate (40 ml) (pH 8.5), saturated sodium chloride solution (40 ml) was added, and the mixture was extracted with 3:1-chloroform:2-propanol. The extracts were concentrated. The residue was flash chromatographed on silica gel, eluting with 0.5% to 5% methanol:ethyl acetate. The appropriate fractions were collected and evaporated. Recrystallization of the residue from 1:1-hexane:ethyl acetate gave 2.64 g (34%) of product, mp 83°–85° C.

Analysis: Calculated for $C_{23}H_{28}N_2O_3$: 72.61%C 7.42%H 7.36%N Found: 72.76%C 7.66%H 7.31%N

EXAMPLE 59

Ethyl erythro-2-acetamido-3-hydroxy-3-[6-(5-phenyl-1-pentynyl)-2-pyridinyl]propionate A mixture of ethyl erythro-2-acetamido-3-(6-bromo-2-pyridinyl)-3-hydroxypropionate (23.2 g), 5-phenyl-1-pentyne (12.1 g), triethylamine (10.6 g), bis(triphenylphosphine)palladium chloride (0.98 g), and cuprous iodide (0.13 g) in dry tetrahydrofuran (100 ml) was heated at 55° C. for 1.5 hrs under nitrogen. Additional 5-phenyl-1-pentyne (6.1 g), triethylamine (7.1 g), bis(triphenylphosphine)palladium chloride (0.49 g), and cuprous iodide (0.07 g) were added, and the reaction mixture was heated overnight. The reaction mixture was filtered and the filtrate was evaporated. The residue was redissolved in ethyl acetate, washed with half-saturated sodium chloride solution, and flash chromatographed on silica gel, eluting with 1:1-hexane:ethyl acetate. The appropriate fractions were collected. The residue was rechromatographed, eluting with 1%-methanol:chloroform to give 14.2 g (51.6%) of product.

Analysis: Calculated for $C_{23}H_{26}N_2O_4$: 70.03%C 6.64%H 7.10%N Found: 69.30%C 6.75%H 6.94%N

EXAMPLE 60 erythro-N-{1,3-Dihydroxy-1-[6-(5-phenyl-1-pentynyl)-2-pyridinyl]-2-propanyl}acetamide To a solution of ethyl erythro-2-acetamido-3-hydroxy-3-[6-(5-phenyl-1-pentynyl)-2-pyridinyl]propionate (12.3 g) in dry tetrahydrofuran (100 ml) was added 2.0M lithium borohydride/tetrahydrofuran (15.5 ml) at 0° C., under nitrogen. The reaction mixture was stirred at ambient temperature overnight, chilled, and 1:1-methanol:water (45 ml) and glacial acetic acid (1.8 ml) were added until a pH of 6.5 was obtained. The mixture was stirred at ambient temperature for 80 min. The reaction mixture was evaporated, the residue was azeotroped with methanol and slurried with 7.5% sodium bicarbonate solution (25 ml) (pH 8.5). The mixture was extracted with 3:1-chloroform:2-propanol, filtered, and the filtrate was concentrated. The residue was flash chromatographed on silica gel, eluting with 0.5% to 1%-methanol:ethyl acetate. The appropriate fractions were collected and concentrated to give 6.0 g (54.6%) of product, mp 91°–95° C.

Analysis: Calculated for $C_{12}H_{24}N_2O_3$: 71.57%C 6.86%H 7.95%N Found: 71.48%C 6.75%H 7.92%N

EXAMPLE 61 erythro-N-{1,3-Dihydroxy-1-[6-(5-phenylpentyl)-2-pyridinyl]-2-propanyl}acetamide hydrate erythro-N-{1,3-Dihydroxy-1-[6-(5-phenyl-1-pentynyl-2-pyridinyl]-2-propanyl}acetamide (5.45 g) in ethanol (150 ml) containing 5% palladium-on-carbon (0.20 g) was shaken on a Parr hydrogenator at 40 psi of hydrogen. After 1.5 hrs, the catalyst was collected. The filtrate was evaporated, and the residue was chromatographed on silica gel, eluting with 0.5%–1% methanol acetate to give 2.8 g (50%) of product.

Analysis: Calculated for $C_{21}H_{28}N_2O_3 \cdot H_2O$: 67.36%C 8.07%H 7.48%N Found: 67.95%C 8.02%H 7.53%N

EXAMPLE 62 erythro-2-Amino-1-[6-(5-phenylpentyl)-2-pyridinyl]-1,3-propanediol hemihydrate

A solution of erythro-N-{1,3-dihydroxy-1-[6-(5-phenylpentyl)-2-pyridinyl]-2-propanyl}acetamide (3.5 g), hydrazine hydrate (32 ml), and ethanol (25 ml) was heated under reflux, under nitrogen, for 26 hrs. The reaction mixture was cooled, water (40 ml) was added, and the mixture was extracted with chloroform. The extracts were washed with saturated sodium chloride solution, dried over anhydrous magnesium sulfate, filtered, and the filtrate was evaporated. A mixture of the residue and 0.25 g from a similar experiment was chromatographed on silica gel, eluting with 970:30:2 to 950:50:3-chloroform:methanol:2N ammonium hydroxide. The appropriate fractions were collected and evaporated. The residue was dissolved in chloroform (100 ml), and the solution was washed with saturated sodium chloride solution, dried over anhydrous magnesium sulfate, filtered, and the filtrate was evaporated. The residue was dried at 70° C. under high vacuum to give 2.23 g (64%) of product.

Analysis: Calculated for $C_{19}H_{26}N_2O_2 \cdot 0.5H_2O$: 70.56%C 8.41%H 8.66%N Found: 70.77%C 8.23%H 8.62%N

EXAMPLE 63 erythro-N-{1,3-Dihydroxy-1-[3-(1-undecynyl)phenyl]-2-propanyl}acetamide

To ethyl erythro-2-acetamido-3-hydroxy-3-[3-(1-undecynyl)phenyl]propionate (7.3 g) in dry tetrahydrofuran (75 ml) was added 2.0M lithium borohydride tetrahydrofuran (11.4 ml) at 0° C., under nitrogen. The reaction mixture was chilled, stirred at ambient temperature overnight, and a mixture of glacial acetic acid (1.3 ml), methanol (25 ml) and water (25 ml) was added dropwise to a final pH of 6. The solution was concentrated and the residue was extracted with ethyl acetate. The extracts were dried over anhydrous magnesium sulfate, filtered, and the filtrate was concentrated. Trituration of the residue with 2:3-ether:hexane and recrystallization of the residue from ethyl acetate gave 1.9 g (29%) of product, mp 99°–101° C.

Analysis: Calculated for $C_{22}H_{33}NO_3$: 73.50%C 9.25%H 3.90%N Found: 73.56%C 9.05%H 3.93%N

EXAMPLE 64 erythro-N-{1-[3-(1-Dodecynyl)phenyl]-1,3 dihydroxy-2-propanyl}acetamide

To ethyl erythro-2-acetamido-3-[3-(1-dodecynyl)phenyl]-3-hydroxypropionate (24.0 g) in tetrahydrofuran (220 ml) was added 2N lithium borohydride tetrahydrofuran (29 ml) at 2° C., under nitrogen. The reaction mixture was chilled, stirred at ambient temperature for 2.5 hrs. and 1:1-methanol:water (100 ml) and glacial acetic acid (3.3 ml) was added slowly until a pH of 6.5 was obtained. The solution was stirred at ambient temperature for 0.5 hr, evaporated, and the residue was azeotroped with methanol. The residue was slurried with 7.5% sodium bicarbonate solution (50 ml) (pH 8.5),and the mixture was extracted with 3:1-chloroform:propanol. The extract was concentrated. The residue was flash chromatographed on silica gel, eluting with ethyl acetate. The appropriate fractions were collected and evaporated. Recrystallization of the residue from ethyl acetate gave 9.13 g (42.4%) of product, mp 93°–95° C.

Analysis: Calculated for $C_{23}H_{35}NO_3$: 73.96%C 9.44%H 3.75%N Found: 73.66%C 9.14%H 3.69%N

EXAMPLE 65 erythro-N-[1-(3-Dodecylphenyl)-1,3-dihydroxy-2-propanyl]acetamide erythro-N-{1-(3-Dodecynyl)phenyl]-1,3-dihydroxy-2-propanyl}acetamide (4.4 g) in ethanol (100 ml) containing 5% palladium-on-carbon (0.02 g) was shaken on a Parr hydrogenator at 35 psi of hydrogen for 2.5 hrs. The catalyst was collected, the solvent evaporated, and the residue was recrystallized from ethyl acetate to give 4.1 g (90.6%) of product, mp 101°–104° C.

Analysis: Calculated for $C_{23}H_{39}NO_3$: 73.17%C 10.41%H 3.71%N Found: 72.82%C 10.36%H 3.54%N

EXAMPLE 66 erythro-2-Amino-1-(3-dodecylphenyl)-1,3-propanediol erythro-N-[1-(3-Dodecylphenyl)-1,3-dihydroxy-2-propanyl]acetamide (2.9 g), hydrazine hydrate (25 ml), and ethanol (25 ml) were heated under reflux, under nitrogen for 22 hrs. The reaction mixture was washed with saturated sodium chloride solution, dried over anhydrous magnesium sulfate, filtered, and the filtrate was evaporated. The residue was chromatographed on silica gel, eluting with 950:50:3-chloroform:methanol:2N ammonium hydroxide. The appropriate fractions were collected and evaporated. The residue was dissolved in ethyl acetate (75 ml), and the solution was washed with half-saturated sodium chloride solution, dried over anhydrous magnesium sulfate, evaporated, and the residue was azeotroped with toluene to give 1.35 g (52%) of product, mp 36°–40° C.

Analysis: Calculated for $C_{21}H_{37}NO_2$: 75.17%C 11.12%H 4.17%N Found: 75.14%C 11.18%H 4.12%N

EXAMPLE 67 erythro N-[1-[5-(1-Dodecyl)-2-thienyl]-1,3-diacetoxy-2-propyl]acetamide

A solution of erythro N-[1-[5-(1-dodecyl)-2-thienyl]-1,3-dihydroxy-2-propyl]acetamide (12.0 g), acetic anhydride (19.2 g), triethylamine (28.4 g),and dimethylaminopyridine (0.4 g) in dry tetrahydrofuran (150 ml) was stirred at ambient temperature for 3 hrs. The reaction mixture was evaporated and the residue was dissolved in chloroform. The solution was washed with water, dried, filtered, and the filtrate was evaporated. The residue was dried to give 13.6 g (93.5%) of product, mp 105°–107° C.

Analysis: Calculated for $C_{25}H_{41}NO_5S$: 64.21%C 8.84%H 2.99%N Found: 64.33%C 8.92%H 3.02%N

EXAMPLE 68

Ethyl erythro-2-acetamide-3-[5-(1-nonynyl)-2-thienyl]-3-hydroxypropionate

A slurry of 5-nonynyl-2-thiophenecarboxaldehyde (40.0 g), acetamidomalonic acid monoethyl ester (32.3 g) and dry tetrahydrofuran (150 ml) was degassed and cooled to 0° C. Triethylamine (18.2 g) was added, the solution degassed, and the reaction mixture was stirred at room temperature under nitrogen for four days, Acetamidomalonic acid monoethyl ester (32.3 g) and triethylamine (18.2 g) were added, and the reaction mixture was stirred at room temperature under nitrogen for an additional four days. The reaction mixture was evaporated and the residue dried under vacuum. The residue was flash chromatographed (silica; 1:1-ethyl acetate:hexane). The appropriate fractions were collected and evaporated. The residue was crystallized from ether, then recrystallized twice from ethyl acetate to give 40.2 (62%) of product, mp 104°–106° C.

Analysis: Calculated for $C_{20}H_{29}NO_4S$: 63.30%C 7.70%H 3.69%N Found: 63.30%C 7.64%H 3.71%N

EXAMPLE 69 erythro-N-[1-[5-(1-Nonynyl)-2-thienyl]-1,3-dihydroxy-2-propyl]acetamide

A solution of ethyl erythro-2-acetamido-3-[5-(1-nonynyl)-2-thienyl]-3-hydroxypropionate (40.0 g) in dry tetrahydrofuran (150 ml) was stirred at 0° C. under nitrogen as lithium borohydride (2.0M in tetrahydrofuran, 68.5 ml) was added dropwise. The reaction mixture was stirred under a nitrogen atmosphere overnight, warming to room temperature. A solution of 50:50:8-methanol:water:acetic acid (108 ml) was added, with cooling in an ice-bath. The solution was neutralized with glacial acetic acid and evaporated. The residue was diluted with water and extracted with ethyl acetate. The combined organic extracts were dried over anhydrous sodium sulfate, filtered, and the filtrate was evaporated. The residue was flash chromatographed (silica; 2–4%-methanol-ethyl acetate). The appropriate fractions were collected and evaporated. The residue was recrystallized twice from ethyl acetate to give 29.9 g (84%) of product, mp 81°–83° C.

Analysis: Calculated for $C_{18}H_{27}NO_3S$: 64.06%C 8.06%H 4.15%N Found: 64.04%C 8.17%H 4.16%N

EXAMPLE 70 erythro-2-Amino-1-[5-(1-nonynyl)-2-thienyl]-1,3-propanediol

A solution of erythro-N-[1-[5-(nonynyl)-2-thienyl]-1,3-dihydroxy-2-propyl]acetamide (16.4 g), 2N sodium hydroxide solution (150 ml), and 95% ethanol (75 ml) was stirred at 70° C. overnight. The reaction mixture was cooled to room temperature and acidified with glacial acetic acid. The solution was diluted with water (200 ml), basified with sodium bicarbonate solution and chilled. The precipitate was collected, and the filtrate was extracted with 4:1-chloroform:2-propanol. The combined organic extracts were dried over anhydrous sodium sulfate, filtered, and the filtrate was evaporated. The residue was combined with the precipitate and flash chromatographed (silica, 90:9:1-dichloromethane:methanol:ammonium hydroxide) to give 11.8 g (82%) of product. A portion of product was crystallized from ether to give the analytical sample, mp 64°–67° C.

Analysis: Calculated for $C_{16}H_{25}NO_{2}S$: 65.05%C 8.53%H 4.74%N Found: 65.22%C 8.56%H 4.76%N

EXAMPLE 71 erythro-N-[1-[5-(1-Nonyl)-2-thienyl]-1,3-dihydroxy-2-propyl]acetamide

A mixture of erythro-N-[1-[5-(1-nonynyl)-2-thienyl]-1,3-dihydroxy-2-propyl]acetamide (8.00 g), 5% palladium-on-carbon (800 mg), and absolute ethanol (500 ml) was shaken under 50 psi of hydrogen overnight. The catalyst was filtered through a bed of celite, and the filtrate was washed with ethanol. The filtrate was evaporated, and the residue was recrystallized twice from ethyl acetate to give 7.0 g (86%) of product, mp 98°–100° C.

Analysis: Calculated for $C_{18}H_{13}NO_{3}S$: 63.31%C 9.15%H 4.10%N Found: 63.03%C 9.14%H 4.01%N

EXAMPLE 72

5-(6-Phenyl-1-hexynyl)-2-thiophenecarboxaldehyde

A solution of 6-phenyl-1-hexyne (30.6 g), 5-bromo-2-thiophenecarboxaldehyde (37.0), and triethylamine (58.7 g) in dry tetrahydrofuran (75 ml) was degassed and stirred at room temperature under a nitrogen atmosphere. Two mole percent of bis(triphenylphosphine)palladium(II)chloride (2.7 g) followed by one mole percent of copper(I)iodide (0.4 g) was added. The mixture was degassed and stirred at room temperature under nitrogen overnight. The precipitate was filtered and washed with ethyl acetate. The filtrate was evaporated, and the residue was distilled to give 47.0 g (91%) of product. A two gram-portion of product was flash chromatographed (silica, 1:1-toluene:hexane). The appropriate fractions were collected and evaporated. The residue was distilled in a kugelruhr oven (170° C./0.07 mm mercury) to give the analytical sample, as an oil.

Analysis: Calculated for $C_{17}H_{16}OS$: 76.08%C 6.01%H Found: 75.54%C 6.04%H

EXAMPLE 73 erythro-N-[1-[5-(6-Phenyl-1-hexynyl)-2-thienyl]-1,3-dihydroxy-2-propyl]acetamide A solution of ethyl erythro-2-acetamido-3-[5-(6-phenyl-1-hexynyl)-2-thienyl]-3-hydroxypropionate (41.6 g) in dry tetrahydrofuran (150 ml) was stirred at 0° C., under nitrogen, as a solution of lithium borohydride (2.0M in tetrahydrofuran, 66 ml) was added dropwise. The reaction mixture was warmed to room temperature and stirred under a nitrogen atmosphere for four hrs. A solution of 50:50:8 methanol:water:acetic acid (108 ml) was added with cooling in an ice-bath. Glacial acetic acid was added, and the solution was evaporated. Water was added to the residue, and the solution was extracted with ethyl acetate. The combined organic extracts were dried over anhydrous sodium sulfate, filtered, and the filtrate was evaporated. The residue was flash chromatographed (silica; 90:9:1 dichloromethane:methanol:2N ammonium hydroxide). The appropriate fractions were collected and evaporated. Recrystallization of the residue from ethyl acetate gave 31.5 g (84%) of product, mp 131°–133° C.

Analysis: Calculated for $C_{21}H_{25}NO_{3}S$: 67.90%C 6.78%H 3,77%N Found: 67.54%C 6.88%H 3.71%N

EXAMPLE 74 erythro-2-Amino-1-[5-(6-phenyl-1-hexynyl)-2-thienyl]-1,3-propanediol

A solution of erythro-N-[1-[5-(6-phenyl-1-hexynyl)-2-thienyl]-1,3-dihydroxy-2-propyl]acetamide (10.0 g), 1N sodium hydroxide solution (125 ml) and 95% ethanol (75 ml) was stirred at 65° C. overnight. The reaction mixture was evaporated, and the residue was neutralized with glacial acetic acid. The solution was diluted with water (200 ml) and extracted with 4:1-chloroform:2-propanol. The combined organic extracts were dried over anhydrous sodium sulfate, filtered, and the filtrate was evaporated. The residue was flash chromatographed (silica; 90:9:1-dichloromethane:methanol:2N ammonium hydroxide). The appropriate fractions were collected and evaporated to give 7.8 g (88%) of product. A portion was crystallized from ethyl acetate-hexane to give the analytical sample, mp 130°–140° C. (dec).

Analysis: Calculated for $C_{19}H_{23}NO_{2}S$: 69.27%C 7.04%H 4.25%N Found: 69.29%C 7.14%H 4.26%N

EXAMPLE 75

4-(1-Dodecynyl)-2-thiophenecarboxaldehyde

A solution of 1-dodecyne (23.9 g), 5-bromo-2-thiophenecarboxaldehyde (25.0 g) and triethylamine (39.7 g) in dry tetrahydrofuran (75 ml) was degassed and stirred at room temperature under a nitrogen atmosphere. Two mole percent of bis(triphenylphosphine)palladium(II)chloride (1.8 g) followed by one mole percent of copper(I)iodide (0.25 g) was added. The mixture was degassed and stirred at room temperature under nitrogen for three days. The precipitate was filtered, and the filter cake was washed with ethyl acetate. The filtrate was evaporated, and the residue was flash chromatographed (silica, 7:3-Hexane:dichloromethane). The appropriate fractions were collected and evaporated. The residue was dried at 50° C. under vacuum for three hrs to give 35.5 g (98%) of product.

Analysis: Calculate for $C_{17}H_{24}OS$: 73.86%C 8.75%H Found: 73.79%C 9.08%H

EXAMPLE 76

Ethyl erythro-2-acetamide-3-[4-(1-dodecynyl)-2-thienyl]-3-hydroxypropionate

A slurry of 4-(1-dodecynyl)-2-thiophenecarboxaldehyde (21.4 g), acetamidomalonic acid monoethyl ester (14.6 g), and dry tetrahydrofuran (100 ml) was degassed and cooled to 0° C. Triethylmnine (8.23 g) was added, the solution degassed, and the reaction stirred at room temperature under nitrogen for five days. Additional acetamidomalonic acid monoethyl ester (14.6 g) and triethylamine (8.23 g) were added, and the reaction was stirred at room temperature under nitrogen for five days. The reaction mixture was evaporated, the residue dried under vacuum, and flash chromatographed (silica, 3:2-hexane:ethyl acetate). The appropriate fractions were collected and evaporated. The residue was recrystallized from ethyl acetate-hexane to 23.3 g (71%) of product, mp 79°–81° C.

Analysis: Calculated for $C_{23}H_{35}NO_{4}S$: 65.53%C 8.37%H 3.32%N Found: 65.63%C 7.96%H 3.34%N

EXAMPLE 77 erythro-2-Amino-1-[4-(1-dodecyl)-2-thienyl]-1,3-propanediol

A solution of erythro-N-[1-[4-(dodecyl)-2-thienyl]-1,3-dihydroxy-2-propyl]acetamide (6.35 g), 2N sodium hydroxide solution (100 ml) and 95% ethanol (50 ml) was stirred at 65° C. overnight. The reaction mixture was cooled to room temperature and neutralized with glacial acetic acid. The solution was diluted with water (200 ml) and chilled. The precipitate was collected, and the filtrate was extracted with chloroform. The combined organic extracts were dried over anhydrous sodium sulfate, filtered, and the filtrate was evaporated. The residue was combined with the precipitate and flash chromatographed (silica, 90:9:1-dichloromethane:methanol:2N ammonium hydroxide). The appropriate fractions were collected and evaporated. The residue was recrystallized from ethyl acetate to give 4.1 g (73%) of product, mp 99°–100° C.

Analysis: Calculated for $C_{19}H_{35}NO_2S$: 66.81%C 10.33%H 4.10%N Found: 66.70%C 10.40%H 4.11%N

EXAMPLE 78

Ethyl erythro-2-acetamido-3-[5-(6-phenyl-1-hexynyl)-2-thienyl]-3-hydroxypropionate A slurry of 6-phenyl-1-hexynyl-2-thiophenecarboxaldehyde (45.0 g), acetamidomalonic acid monoethyl ester (31.7 g), and dry tetrahydrofuran (150 ml) was degassed and cooled to 0° C. Triethylamine (17.9 g) was added, the solution degassed, and the reaction mixture stirred at room temperature under nitrogen for two days. Additional acetamidomalonic acid monoethyl ester (31.7 g) and triethylamine (17.9 g) were added, and the reaction mixture was stirred at room temperature under nitrogen for an additional two days. The mixture was evaporated, the residue dried under vacuum, and flash chromatographed (silica, 1:1-ethyl acetate:hexane). The appropriate fractions were collected and evaporated. The residue was recrystallized from ethyl acetate-hexane to give 48.1 g (69%) of product, mp 90°–92° C.

Analysis: Calculated for $C_{23}H_{27}NO_4S$: 66.80%C 6.58%H 3.39%N Found: 66.48%C 6.59%H 3.33%N

EXAMPLE 79 erythro-2-Amino-1-[4-(1-dodecynyl)-2-thienyl]-1,3-propanediol]acetate

A solution of erythro-N-[1-[4-(dodecynyl)-2-thienyl]-1,3-dihydroxy-2-propyl]acetamide (4.30 g), 2N sodium hydroxide solution (100 ml), and 95% ethanol (50 ml) was stirred at 65° C. overnight. The reaction mixture was cooled to room temperature and acidified with glacial acetic acid. The solution was diluted with water (200 ml) and chilled in the refrigerator. The precipitate was collected and the filtrate extracted with chloroform. The combined organic extracts were dried over anhydrous sodium sulfate, filtered, and the filtrate was evaporated. The residue was combined with the precipitate and previously prepared material, and recrystallized twice from ethyl acetate to give 4.0 g (55%) of product, mp 120°–122° C.

Analysis: Calculated for $C_{21}H_{35}NO_2S$: 63.44%C 8.87%H 3.52%N Found: 63.32%C 8.71%H 3.50%N

EXAMPLE 80 erythro-N-[1-[4-(1-Dodecyl)-2-thienyl]1,3-dihydroxy-2-propyl]acetamide

A mixture of erythro-N-[1-[4-(1-dodecynyl)-2-thienyl]-1,3-dihydroxy-2-propyl]acetamide (8.00 g), 5% palladium-on-carbon (800 mg), and absolute ethanol (500 ml) was shaken under 50 psi of hydrogen overnight. The reaction mixture was filtered through a bed of celite, and the filter cake was washed with ethanol. The solvent was evaporated and the residue recrystallized twice from ethyl acetate to give 7.0 g (87%) of product, mp 92°–94° C.

Analysis: Calculated for $C_{21}H_{37}NO_3S$: 65.75%C 9.72%H 3.65%N Found:
65.72%C 9.82%H 3.63%N

EXAMPLE 81 erythro-2-Amino-1-[3-(1-dodecyl)-5-isoxazolyl]-1,3-propanediol

A solution of erythro-N-[1-[3-(1-dodecyl)-5-isoxazolyl]-1,3-dihydroxy-2-propyl]acetamide (4.0 g), degassed 2N sodium hydroxide solution (100 ml), and 95% ethanol (50 ml) was stirred at 60° C. for 3 hrs. The reaction mixture was concentrated, the residue diluted with sodium bicarbonate solution, and extracted with 4:1-chloroform-2-propanol. The combined organic extracts were dried over anhydrous magnesium sulfate, filtered, and the filtrate was evaporated. The residue was recrystallized from ethylacetate-hexane. The precipitate was flash chromatographed (silica, 90:1-dichloromethane:methanol). The appropriate fractions were collected and evaporated. The residue was recrystallized from ethyl acetate-hexane to give 2.3 g (65%) of product, mp 88°–90° C.

Analysis: Calculated for $C_{18}H_{34}N_2O_3$: 66.22%C 10.50%H 8.58%N Found: 65.55%C 10.44%H 8.51%N

EXAMPLE 82

3-(1-Decyl)-5-isoxazolemethanol

To a solution of 1-nitroundecane (38.0 g) and O-trimethylsilylpropynol (24.1 g) in dry benzene (300 ml) was added dropwise a solution of freshly distilled phenylisocyanate (44.9 g) and triethylamine (22.4 g) in dry benzene (50 ml) at 40° C., with stirring. The reaction mixture was heated at 60° C. for 3 hrs, cooled, and filtered. To the filtrate was added 1.0M tetrabutylammonium fluoride (40 ml). After 30 mins, the solution was evaporated, and the residue was flash chromatographed (silica gel, 1% methanol-dichloromethane) to give 15.5 g (34%) of product, mp 55°–56° C.

Analysis: Calculated for $C_{14}H_{25}NO_2$: 70.25%C 10.53%H 5.85%N Found: 70.44%C 10.42%H 5.92%N

EXAMPLE 83

3-(1-Decyl)-5-isoxazolecarboxaldehyde

To a solution of oxalyl chloride (31.7 ml) in dry dichloromethane (100 ml) cooled to −60° C., was added a solution of dimethylsulfoxide (9.8 ml) in dichloromethane (30 ml) followed by a slurry of 3-(1-decyl)-5-isoxazolemethanol (13.8 g) in dry dichloromethane (100 ml). The reaction mixture was stirred at −60° C. for 0.5 hr, quenched with triethylamine (40 ml), and allowed to warm to ambient temperature. The solution was poured into water (300 ml) and extracted with dichloromethane. The organic phases were washed with dilute citric acid, dried, and evaporated. The residue was flash chromatographed (silica, 50:1-dichloromethane:methanol). The appropriate fraction were collected and evaporated. The residue was recrystallized from ether-hexane to give 11.2 g (82%) of product, mp 46°–48° C.

Analysis: Calculated for $C_{14}H_{23}NO_2$: 70.85%C 9.77%H 5.90%N Found: 71.16%C 9.93%H 5.94%N

EXAMPLE 84

Ethyl erythro-2-acetamido-3-(3-(1-decyl)-5-isoxazolyl)-3-hydroxypropionate

To a mixture of 3-(decyl)-5-isoxazolecarboxaldehyde (10 g), and acetamidomalonic acid monoethylester (7.9 g) in dry tetrahydrofuran (100 ml), cooled to 0° C., was added triethylamine (4.5 g), under nitrogen. The solution was allowed to warm to room temperature and stirred for 16 hrs. The solution was evaporated, and the residue was recrystallized twice from ethyl acetate-hexane to give 10.3 g (64%) of product, mp 83°–85° C.

Analysis: Calculated for $C_{20}H_{34}N_2O_5$: 62.80%C 8.96%H 7.32%N Found: 62.87%C 9.30%H 7.32%N

EXAMPLE 85 erythro-2-Amino-1-[3-(1-decyl)-5-isoxazolyl]-1,3-propanediol

A solution of erythro-N-[1-[5-(decyl)-3-isoxazolyl]-1,3-dihydroxy-2-propyl]acetamide (9.30 g), degassed 2N sodium hydroxide solution (200 ml), and 95% ethanol (100 ml) was stirred at 80° C. for 6 hrs. The reaction mixture was concentrated, the residue diluted with sodium bicarbonate solution, and extracted with 4:1-chloroform:2-propanol. The combined organic extracts were dried over anhydrous magnesium sulfate, filtered, and the filtrate was evaporated. The residue was flash chromatographed (silica; 9:1 dichloromethane:methanol). The appropriate fractions were collected and evaporated. The residue was recrystallized from ethyl acetate-hexane to give 6.1 g (75%) of product, mp 88°–90° C.

Analysis: Calculated for $C_{16}H_{30}N_2O_3$: 64.40%C 10.13%H 9.39%N Found: 64.37%C 10.25%H 9.42%N

EXAMPLE 86

5-(1-Undecynyl)-2-thiophenecarboxaldehyde

A solution of 1-undecyne (62.7 g), 5-bromo-2-thiophenecarboxaldehyde (75.0 g), and triethylamine (119.2 g) in dry tetrahydrofuran (300 ml) was degassed and stirred at 0°–5° C., under a nitrogen atmosphere. Two mole percent of bis(triphenylphosphine)palladium(II)chloride (5.51 g) followed by one mole percent of copper(I)iodide (0.75 g) was added and the mixture was degassed and stirred at room temperature overnight, under nitrogen. The precipitate was filtered and the filter cake was washed with ethyl acetate. The filtrate was evaporated and the residue purified by flash chromatography (silica; 5% ethyl acetate-hexane). The appropriate fractions were collected and evaporated to give 88.1 g (85%) of product as an oil. The oil was dried at 50° C. under high vacuum (approx. 0.01 mm mercury) for four hrs to provide the analytical sample.

Analysis: Calculated for $C_{16}H_{22}OS$: 73.23%C 8.45%H Found: 73.15%C 8.50%H

EXAMPLE 87

Ethyl erythro-2-acetamido-3-[5-(1-undecynyl)-2-thienyl]-3-hydroxypropionate

A slurry of 5-undecynyl-2-thiophenecarboxaldehyde (86.1 g), acetamidomalonic acid monoethyl ester (62.0 g), and dry tetrahydrofuran (300 ml) was degassed and cooled to 0° C. Triethylamine (34.8 g) was added, the solution were degassed, and the reaction mixture was stirred at room temperature for four days, under nitrogen. Acetamidomalonic acid monoethyl ester (62.0 g) and triethylamine (34.8 g) were added, and the reaction mixture was stirred at room temperature for an additional two days, under nitrogen. The reaction mixture was evaporated, and the residue was dried under vacuum. The residue was purified by flash chromatography (silica; 1:1-ethyl acetate-hexane). The appropriate fractions were collected and evaporated, and the residue was recrystallized from ethyl acetate to give 86.5 g (65%) of product, mp 80°–82° C.

Analysis: Calculated for $C_{22}H_{33}NO_4S$: 64.83%C 8.16%H 3.44%N Found: 64.65%C 8.07%H 3.45%N

EXAMPLE 88 erythro-N-[1-[5-(1Undecynyl)-2-thienyl]-1,3-dihydroxy-2-propyl]acetamide

A solution of ethyl erythro-2-acetamido-3-[5-(1-undecynyl)-2-thienyl]-3-hydroxypropionate (86.2 g) in dry tetrahydrofuran (200 ml) was stirred at 0° C., under nitrogen. Lithium borohydride (137.5 ml, 2.0M in tetrahydrofuran) was added dropwise. The reaction mixture was allowed to warm to room temperature, and was stirred for four hrs, under nitrogen. The reaction mixture was cooled in an ice-bath. Methanol:water:acetic acid solution (50 ml:50 ml:10 ml) was added. The solution was neutralized with glacial acetic acid. The mixture was evaporated, and the residue was diluted with water (400 ml) and extracted with ethyl acetate. The combined organic extracts were dried over anhydrous sodium sulfate, filtered, and the filtrate was evaporated. The residue was purified by flash chromatography (silica; 7% methanol:dichloromethane). The appropriate fractions were collected and evaporated. Recrystallization of the residue from ethyl acetate gave 61.2 g (79%) of product, mp 88°–90° C.

Analysis: Calculated for $C_{20}H_{31}NO_3S$: 65.72%C 8.55%H 3.83%N Found: 66.00%C 8.71%H 3.82%N

EXAMPLE 89

(4-trans)-N-[2,2-Dimethyl-4-[5-(1-undecynyl)-2-thienyl]-1,3-dioxan-5-yl]acetamide To a solution of erythro-N-[1-[5-(1-undecynyl)-2-thienyl]-1,3-dihydroxy-2-propyl]acetamide (25 g) in dry acetone (400 ml) was added 2,2-dimethoxypropane (45.3 g) and a catalytic amount of para-toluenesulfonic acid. The solution was stirred at room temperature for 7 hrs and then evaporated. The residue was purified by column chromatography (silica gel, 4:1 chloroform:ether). The appropriate fractions were collected and concentrated. Recrystallization from ether-hexane gave 20.9 g (73.8%) of product, mp 88°–89° C.

Analysis: Calculated for $C_{23}H_{35}NO_3S$: 68.11%C 8.70%H 3.45%N Found: 68.26%C 8.83%H 3.39%N

EXAMPLE 90 erythro-N-[1-[5-(1-Nonynyl)-2-thienyl]-1,3-dihydroxy-2-propyl]-1,1-dimethylethylcarbamate To a slurry of erythro-2-amino-1-[5-(1-nonynyl)-2-thienyl]-1,3-propanediol (2.8 g) in saturated sodium bicarbonate solution (50 ml) was added a solution of di-tert-butyl dicarbonate (2.24 g) in chloroform (50 ml), over two mins. The mixture was stirred at 60° C. for 45 mins, the layers were separated, and the organic layer was dried and evaporated. The residue was purified by passage through a short pad of silica gel, and the filtrate was evaporated. The residue was crystallized from ether-hexane to give 2.9 g (77.6%) of product, mp 73°–75° C.

Analysis: Calculated for $C_{21}H_{33}NO_4S$: 63.77%C 8.41%H 3.54%N Found: 63.65%C 8.31%H 3.50%N

EXAMPLE 91 erythro-2-Amino-1-[5-(1-nonyl)-2-thienyl]-1,3-propanediol acetate

A solution of erythro-N-[1-[5-(1-nonyl)-2-thienyl]-1,3-dihydroxy-2-propyl]acetamide (7.30 g), 2N sodium hydroxide solution (100 ml) and 95% ethanol (75 ml) was stirred at 65° C. overnight. The reaction mixture was concentrated, and the aqueous residue was neutralized with glacial acetic acid. The solution was diluted with water (200 ml) and extracted with 4:1-chloroform:isopropanol. The combined organic extracts were dried over anhydrous sodium sulfate, filtered, and the filtrate was evaporated. The residue was purified by flash chromatography (silica; 90:9:1-dichloromethane:methanol:ammonium hydroxide). The appropriate fractions were collected and concentrated. The residue was dissolved in ethanol, and excess glacial acetic acid was added. Ether and hexane were added. The precipitate was recrystallized from ethyl acetate to give 4.1 g (53%) of product, mp 109°–111° C.

Analysis: Calculated for $C_{18}H_{33}NO_4S$: 60.13%C 9.25%H 3.90%N Found: 60.02%C 8.99%H 3.90%N

EXAMPLE 92 erythro-2-Dimethylamino-1-[5-(6-phenyl-1-hexynyl)-2-thienyl]-1,3-propanediol

To a mixture of erythro-2-amino-1-[5-(6-phenyl-1-hexynyl)-2-thienyl]-1,3-propanediol (4.0 g), 37% aqueous formaldehyde (9.1 ml), and acetonitrile (50 ml) was added sodium cyanoborohydride (2.29 g) in three portions, with stirring at room temperature. After stirring for 30 mins, glacial acetic acid (1 ml) was added dropwise, and stirring was continued for 30 mins. The mixture was neutralized with acetic acid and evaporated. 1N Sodium hydroxide (200 ml) was added to the residue, and the mixture was extracted with chloroform. The extracts were dried over anhydrous sodium sulfate, filtered, and the filtrate was evaporated. The residue was flash chromatographed on silica gel, using 10% methanol:dichloromethane as eluent. The appropriate fractions were collected and evaporated to give 1.3 g (30%) of product, as an oil.

EXAMPLE 93

4-(1-Dodecenyl)-2-thiophenecarboxaldehyde

A solution of 1-dodecyne (50.0 g), tributyltinhydride (109.4 g), and azobisisobutyronitrile (100 mg) was stirred at 95° C. for 3 hrs. The reaction mixture was cooled to 50° C. and evaporated. The residue was filtered through a column of silica, using hexane as the eluent. The appropriate fractions were collected and evaporated. The residue was dried under vacuum to give 131.7 g (96.0%) of tri-n-butyl-1-dodecenylstannane.

To a solution of 4-bromo-2-thiophenecarboxaldehyde (35.0), tetrakis(triphenylphosphine)palladium(0) (4.23 g), 2,6-di-t-butyl-4-methylphenol (a few milligrams) and dry toluene (150 ml) was added tri-n-butyl-1-dodecenylstannane (92.0 g), dropwise at room temperature, under nitrogen. The solution was heated under reflux for four hrs, with stirring. After cooling to room temperature, the solution was filtered through a bed of celite, and the filter cake was washed with ether. The filtrate was evaporated and the residue purified by flash chromatography (silica; 5% ethyl acetate-hexane). The appropriate fractions were collected and concentrated. The residue was distilled in a kugelrohr oven (170° C./0.3 mm mercury) to give 46.7 g (92%) of product, as an oil ca. 4:1-trans:cis).

Analysis: Calculated for $C_{17}H_{26}OS$: 73.33%C 9.41%H Found: 73.64%C 9.62%H

EXAMPLE 94

Ethyl erythro-2-acetamido-3-[5-(1-dodecenyl)-2-thienyl]-3-hydroxypropionate

A slurry of 5-dodecenyl-2-thiophenecarboxaldehyde (46.0 g, ca. 4:1-trans:cis), acetamidomalonic acid monoethyl ester (31.3 g), and dry tetrahydrofuran (300 ml) was degassed and cooled to 0° C. Triethylamine (17.6 g) was added, the solution was degassed, and the reaction mixture was stirred at room temperature for three days, under nitrogen. Acetamidomalonic acid monoethyl ester (46.0 g) and triethylamine (17.6 g) were added, and the reaction mixture was stirred at room temperature for an additional three days, under nitrogen. The reaction mixture was concentrated, and the residue was dried under vacuum. The residue was purified by flash chromatography (silica; 2:3 ethyl acetate-hexane). The appropriate fractions were collected and concentrated. The residue was recrystallized from diethyl ether to give 36.7 g (53%) of product (ca. 4:1-trans:cis), mp 66°–68° C.

Analysis: Calculated for $C_{23}H_{37}NO_4S$: 65.21%C 8.80%H 3.31%N Found: 65.36%C 8.71%H 3.32%N

EXAMPLE 95 erythro-N-{1.3-Diacetyloxy-1-[6-(5-phenyl-1-pentynyl)-2-pyridinyl]-2-propanyl}acetamide A diastereomeric mixture of N-{1,3-dihydroxy-1-[6-(5-phenyl-1-pentynyl)-2-pyridinyl]-2-propanyl}acetamide (18.4 g, 6:1-erythro:threo), acetic anhydride (31.9 g), triethylamine (47.5 g), and 4-dimethylaminopyridine (0.64 g) in tetrahydrofuran (200 ml) was stirred at room temperature overnight. The reaction mixture was concentrated, methanol was added, and the mixture was warmed at 50° C. for 20 mins. The mixture was evaporated, and the residue azeotroped with toluene. A 7.5% sodium bicarbonate solution was added until pH 8.5, and the mixture was extracted into chloroform. The extract was dried over anhydrous magnesium sulfate, filtered, and the filtrate was concentrated. The residue and one (8.0 g) from a similar reaction (18.8 mmol) were combined and purified by flash chromatography, eluting with 1:1-yield hexane:ethyl acetate. The appropriate fractions were collected and concentrated to yield 5.06 g (16.3% yield) of product, mp 104°–106° C.

Analysis: Calculated for $C_{25}H_{28}N_2O_5$: 68.79%C 6.47%H 6.42%N Found: 68.69%C 6.47%H 6.36%N

EXAMPLE 96 erythro-2-Amino-1-[6-(5-phenyl-1-pentynyl)-2-pyridinyl]-1,3-propanediol hemihydrate erythro-N-†1,3-Dihydroxy-1-[6-(5-phenyl-1-pentynyl)-2-pyridinyl]-2-propanyl}acetamide (4.4 g), 2N sodium hydroxide solution (100 ml) and ethanol (50 ml) were heated at 60° C. for 13 hrs, under nitrogen. The reaction mixture was cooled, extracted with chloroform, and the extract was washed with half-saturated sodium chloride solution, dried over anhydrous magnesium sulfate, filtered, and the filtrate was evaporated. The residue was chromatographed twice on silica gel eluting with 950:50:3 to 920:80:5 chloroform:methanol:2N ammonium hydroxide. The appropriate fractions were collected and concentrated. The residue was dissolved in ethyl acetate, and the solution was washed with saturated sodium chloride solution, dried over anhydrous magnesium sulfate, filtered, and the filtrate was concentrated to give 1.13 g (36.5%) of product, as an oil (dried 60° C. under vacuum).

Analysis: Calculated for $C_{19}H_{22}N_2O_2 \cdot 0.5H_2O$: 71.44%C 7.26%H 8.77%N Found: 71.87%C 7.11%H 8.67%N

EXAMPLE 97 erythro-N-[1,3-Dihydroxy-1-(6-undecyl-2-pyridinyl)-2-propanyl]acetamide

A mixture of erythro-N-{1,3-Dihydroxy-1-[6-(1-undecynyl)-2-pyridinyl]-2-propanyl}acetamide (5.4 g) in ethanol (125 ml), and 5% palladium-on-carbon (0.20 g) was hydrogenated on a Parr hydrogenator at 40 psi of hydrogen. After 2.5 hrs, the catalyst was filtered, and the filtrate was concentrated. Recrystallization of the residue from ethyl acetate gave 4.9 g (88.7%) of product, mp 97°–98.5° C.

Analysis: Calculated for $C_{21}H_{36}N_2O_3$: 69.19%C 9.95%H 7.68%N Found: 69.19%C 9.91%H 7.64%N

EXAMPLE 98 erythro-2-Amino-1-(6-undecyl-2-pyridinyl)-1,3-propanediol erythro-N-[1,3-Dihydroxy-1-(6-undecyl-2-pyridinyl)-2-propanyl]acetamide (3.72 g), hydrazine hydrate (32 ml), and ethanol (25 ml) were refluxed for 24 hrs, under nitrogen. The reaction mixture was cooled, water was added, and the mixture was extracted with chloroform. The extract was washed with saturated sodium chloride solution, dried over anhydrous magnesium sulfate, filtered, and the filtrate was evaporated. The residue was chromatographed on silica gel, eluting with 950:50:3 chloroform:methanol:2N ammonium hydroxide. The appropriate fractions were collected and evaporated. The residue was dissolved in chloroform, the solution was washed with saturated sodium chloride solution, dried over anhydrous magnesium sulfate, filtered, and the filtrate was concentrated to give 1.45 g (44%) of product, mp 56°–59° C. (dried at 55° C. under vacuum).

Analysis: Calculated for $C_{19}H_{34}N_2O_2$: 70.76%C 10.63%H 8.69%N Found: 70.20%C 10.71%H 8.48%N

EXAMPLE 99 erythro-2-Amino-1-[6-(1-undecynyl)-2-pyridinyl]-1,3-propanediol hemihydrate erythro-N-{1,3-Dihydroxy-1-[6-(1-undecynyl)-2-pyridinyl]-2-propanyl}acetamide (5.4 g), 2N sodium hydroxide (53 ml), and ethanol (35 ml) were heated at 60° C. for 19 hrs, under nitrogen. The reaction mixture was cooled, extracted with chloroform, and the extract was washed with half-saturated sodium chloride solution, dried over anhydrous magnesium sulfate, filtered, and the filtrate was concentrated. The residue was chromatographed twice on silica gel, eluting with 950:50:3 to 930:70:5 chloroform:methanol:2N ammonium hydroxide. The appropriate fractions were collected and concentrated to give 3.04 g (63.6% yield) of product, as an oil dried at 60° C. under vacuum.

Analysis: Calculated for $C_{19}H_{30}N_2O_2 \cdot 0.5H_2O$: 69.69%C 9.54%H 8.55%N Found: 69.93%C 9.37%H 8.46%N

EXAMPLE 100 erythro-N-{1,3-Diacetyloxy-1-[6-(1-undecynyl)-2-pyridinyl]-2-propanyl}acetamide

A diastereomeric mixture of N-{1,3-dihydroxy-1-[6-(1-undecynyl)-2-pyridinyl]-2-propanyl}acetamide (12.0 g, 4:1 erythro:threo), acetic anhydride (20.4 g), triethylamine (30.4 g), and 4-dimethylaminopyridine (0.41 g) in tetrahydrofuran (125 ml) was stirred at room temperature overnight. The reaction mixture was evaporated, methanol was added, and the solution was warmed at 50° C. for 20 min and evaporated. A 7.5% sodium bicarbonate solution was added until pH 8.5, and the mixture was extracted into chloroform. The extract was dried over anhydrous magnesium sulfate, filtered, and the filtrate was concentrated. The residue was purified by flash chromatography, eluting with 1:1-hexane:ethyl acetate. The appropriate fractions were combined and concentrated to yield 3.5 g (24%) of product, mp 69°–71° C.

Analysis: Calculated for $C_{25}H_{36}N_2O_5$: 67.54%C 8.16%H 6.30%N Found: 67.65%C 8.23%H 6.18%N

EXAMPLE 101

3-(1-Undecynyl)benzaldehyde

A mixture of 3-bromobenzaldehyde (51.8 g), 1-undecyne (48.6 g), bis(triphenylphosphine)palladium(II)chloride (3.37 g), copper iodide (457 mg), and triethylamine (196 ml) in dry tetrahydrofuran (300 ml) was stirred for 4 hrs at 55° C. The reaction mixture was filtered, the filtrate was diluted with ethyl acetate, and the solution was washed with water and brine. The organic phase was dried over anhydrous magnesium sulfate, filtered, and the filtrate was concentrated in vacuo. The residue was chromatographed on 300 g of silica gel (1:4-ethyl acetate:hexane). The appropriate fractions were collected and evaporated. Distillation of a 40-g sample of the residue (81.3 g) gave 9.5 g (13%) of the product, bp 172°–174° C. (0.5 mm mercury).

Analysis: Calculated for $C_{18}H_{24}O$: 84.32%C 9.44%H Found: 84.76%C 9.57%H

EXAMPLE 102 erythro-2-Amino-1-(3-undecynylphenyl)-1,3-propanediol acetate

A solution of erythro-N-{1,3-diacetyloxy-1-[3-(undecynylphenyl-2-propanyl} acetamide (2.76 g) and aqueous 2N sodium hydroxide solution (62 ml) in ethanol (20 ml) was warmed to 60° C. for 16 hr. The reaction mixture was allowed to cool to room temperature and extracted with chloroform. The extract was dried over anhydrous magnesium sulfate, filtered, and the filtrate was concentrated in vacuo. The residue was chromatographed on silica gel (eluted with 900:100:5 chloroform:methanol:ammonium hydroxide). The residue was rechromatographed (eluted with 9:1-chloroform:methanol) to afford 1.35 g (71%) of the free base.

To a solution of free base (1.05 g) in dichloromethane (10 ml) was added glacial acetic acid (2 ml) followed by hexane (50 ml). The mixture was concentrated in vacuo and the solid was recrystallized from ethyl acetate to afford 860 mg (69%) of product, mp 110°–112° C.

Analysis: Calculated for $C_{22}H_{35}NO_4$: 69.99%C 9.34%H 3.71%N Found: 70.36%C 9.32%H 3.69%N

EXAMPLE 103 erythro-2-Amino-1-[3-(1-dodecynyl)phenyl]-1,3-propanediol acetate erythro-N-{1,3-Dihydroxy-1-[3-(1-dodecynyl)-phenyl]-2-propanyl}acetamide (2.7 g), 2N sodium hydroxide solution (36 ml) and ethanol (20 ml) were heated at 60° C. for 19 hrs, under nitrogen. The reaction mixture was cooled, and extracted with chloroform. The extract was washed with half-saturated sodium chloride solution, dried over anhydrous magnesium sulfate, filtered, and the filtrate was concentrated. The residue was chromatographed on silica gel, eluting with 950:50:3 chloroform:methanol:2N ammonium hydroxide. The appropriate fractions were collected and evaporated. The residue was dissolved in dichloromethane and treated with glacial acetic (0.27 ml). The mixture was concentrated in vacuo and the solid was recrystallized from ethyl acetate to give 1.72 g (61%) of product, mp 104°–105.5° C.

Analysis: Calculated for $C_{23}H_{37}NO_4$: 70.55%C 9.52%H 3.58%N Found: 70.62%C 9.46%H 3.54%N

EXAMPLE 104 erythro-N-{1,3-Diacetyloxy-1-[3-(1-undecynyl)-1-phenyl]-2-propanyl}acetamide

To a solution of erythro-N-{1-[3-(1-undecynyl)phenyl]-1,3-dihydroxy-2-propanyl}acetamide (10:1/erythro:threo) in tetrahydrofuran (80 ml) was added acetic anhydride (9.6 ml), triethylamine (21.3 ml), and 4-dimethylaminopyridine (0.21 g). The mixture was stirred for three days at room temperature, then methanol (100 ml) was added, and the solution was warmed to 50° C. for 20 mins. The mixture was concentrated in vacuo and partitioned between dichloromethane and sodium bicarbonate solution. The organic phase was separated, dried over anhydrous magnesium sulfate, and concentrated in vacuo. The residue was flash chromatographed over silica gel (eluted with chloroform:methanol/12:1). The appropriate fractions were collected and concentrated. The reside was flash chromatographed a second time over silica gel (eluted with ethyl acetate:hexane/1:2) The appropriate fractions were collected and concentrated to afford 4.9 g (64%) of product.

ANALYSIS: Calculated for $C_{26}H_{37}NO_5$: 70.40%C 8.41%H 3.16%N Found: 70.60%C 8.52%H 3.15%N

EXAMPLE 105 erythro-N-{4-[3-(1-undecynyl)phenyl]-2,2-dimethyl-1,3-dioxan-5-yl}acetamide.

To a solution of erythro-N-{1,3-dihydroxy-1-[3-(1-undecynyl)phenyl]-2-propanyl}acetamide (10:1/erythro:threo) (5.6 g) in dichloromethane (100 ml) was added p-toluenesulfonic acid (3.3 g). The reaction mixture was stirred at room temperature overnight, diluted with dichloromethane and washed with saturated sodium bicarbonate solution. The organic phase was dried over anhydrous magnesium sulfate, and concentrated in vacuo. The residue was chromatographed over silica gel (eluted with dichloromethane/methanol/14:1). The appropriate fractions were collected and evaporated. The residue was crystallized from ethanol/water/1:1 to afford 2.13 g (34%) of product, mp 90°–92° C.

ANALYSIS: Calculated for $C_{25}H_{37}NO_3$: 75.15%C 9.33%H 3.51%N Found: 74.59%C 9.43%H 3.51%N

EXAMPLE 106

Ethyl erythro-2-acetamido-3-hydroxy-3-[2-fluoro-3-(1-undecynyl)phenyl]propionate To a solution of 2-fluoro-3-(1-undecynyl)benzaldehyde (4.0 g) in tetrahydrofuran (20 ml) was added acetamidomalonate monoethyl ester (2.84 g) and triethylamine (2.1 ml). The reaction mixture was stirred for 3 days at room temperature. Additional acetamidomalonate monoethyl ester (1.4 g) and triethylamine (1.0 ml) were added, with stirring. The mixture was stirred for 3 additional days and concentrated in vacuo. The residue was flash chromatographed over silica gel (eluted with ethyl acetate/hexane/1:1). The appropriate fractions were collected and evaporated. The residue was crystallized from dichloromethane/hexane/1:10: to afford 3.30 g (54%) of product, mp 81°–82° C.

ANALYSIS: Calculated for $C_{24}H_{34}FNO_4$: 68.71%C 8.17%H 3.34%N Found: 68.90%C 8.37%H 3.38%N

EXAMPLE 107 erythro-N-{1,3-Diacetyloxy-1-[3-(1-dodecynyl)-2-fluorophenyl]-2-propanyl}acetamide To a solution of ethyl erythro-2-acetamido-3-hydroxy-3-[2-fluoro-3-(1-dodecynyl)phenyl]propionate (18:1/erythro:threo) (25.7 g) in tetrahydrofuran (250 ml) at 0° C. was added dropwise 2M lithium borohydride in tetrahydrofuran (37 ml). The reaction mixture was stirred at room temperature overnight, quenched with a solution water (50 ml), methanol (50 ml) and glacial acetic acid (2 ml), and concentrated in vacuo. The residue was extracted with ethyl acetate. The organic phases were combined, dried over anhydrous magnesium sulfate, filtered, and the filtrate was concentrated in vacuo to afford 22.9 g of erythro-N-{1-[3-(1-dodecynyl)-2-fluorophenyl-1,3-dihydroxy]-2-propanyl}acetamide.

To a solution of the acetamidodiol (22.1 g) in tetrahydrofuran (150 ml) was added acetic anhydride (32.8 ml) followed by triethylamine (73 ml) and 4-dimethylaminopyridine (730 mg). The reaction mixture was stirred at room temperature for 24 hrs, and methanol (50 ml) was added. The mixture was concentrated, diluted with ethyl acetate, and the solution was washed with saturated sodium bicarbonate solution. The aqueous phase was separated and extracted with ethyl acetate. The organic phases were combined, dried over anhydrous magnesium sulfate, filtered, and the filtration was concentrated in vacuo. The residue was flash chromatographed over silica gel (eluted with 2:1/heptane:ethyl aceate followed by 1:1/heptane:ethyl acetate) to afford 19.9 g (71%) of product.

ANALYSIS: Calculated for $C_{27}H_{38}FNO_5$: 68.19%C 8.05%H 2.95%N Found: 67.66%C 7.87%H 3.35%N

EXAMPLE 108 erythro-2-Amino-1-[2-fluoro-3-(1-dodecynyl)phenyl]-1,3-propanediol acetate

To a solution of erythro-N-{1,3-diacetyloxy-1-[3-(1-dodecynyl)-2-fluorophenyl]-2-propanyl}acetamide (6.0 g) in ethanol (50 ml) was added 25% aqueous sodium hydroxide solution (20 ml). The mixture was heated under reflux for 3 hrs, allowed to cool to room temperature, and stirred overnight. The mixture was diluted with ethyl acetate and washed with water. The aqueous phase was extracted with ethyl acetate, and the organic phases were combined, dried over anhydrous magnesium sulfate, filtered, and the filtrate was concentrated in vacuo. To a solution of the residue in ethyl acetate:heptane/2:5 was added glacial acetic acid (1 ml). The solution was cooled to 0° C. The precipitate was recrystallized from ethyl acetate to afford 3.23 g (62%) of product, mp 115°–116° C.

ANALYSIS: Calculated for $C_{23}H_{36}FNO_4$: 67.45%C 8.86%H 3.42%N Found: 67.47%C 8.58%H 3.43%N

EXAMPLE 109

Ethyl erythro-2-acetamido-3-hydroxy-3-[2-fluoro-3-(1-dodecynyl)phenyl]propionate To a solution of 2-fluoro-3-(1-dodecynyl)benzaldehyde (30.7 g) in tetrahydrofuran (150 ml) was added acetamidomalonic acid monoethyl ester (20.1 g) followed by triethylamine (14.8 ml). The mixture was stirred for 48 hrs at room temperature, and additional acetamidomalonic acid monoethyl ester (10 g) and triethylamine (7.4 ml) were added. The reaction mixture was stirred for 24 hr, concentrated in vacuo, and the residue was flash chromatographed over silica gel (eluted with ethyl acetate:heptane/1:1). The appropriate fractions were collected and evaporated. The residue was crystallized from ethyl acetate/heptane/1:5 to give 31.1 g (68%) of product, mp 84°–86° C.

ANALYSIS: Calculated for $C_{25}H_{36}FNO_4$: 69.26%C 8.37%H 3.23%N Found: 69.54%C 8.40%H 3.26%N

EXAMPLE 110 erythro-2-Amino-1-[5-(1-undecynyl)-2-thienyl]-1,3-propanediol acetate

A solution of erythro-N-[1-[5-(1-undecynyl)-2-thienyl]-1,3-dihydroxy-2-propyl]acetamide (15.0 g), 2N sodium hydroxide solution (150 ml) and 95% ethanol (100 ml) was stirred at 65° C overnight. The reaction mixture was evaporated, and the aqueous residue was neutralized with glacial acetic acid. The solution was diluted with water (200 ml) and extracted with 4:1 chloroform-isopropanol. The combined organic extracts were dried over anhydrous sodium sulfate, filtered, and the filtrate was evaporated. The residue was flash chromatographed (silica; 90:9:1 dichloromethane/methanol/ammonium hydroxide). The appropriate fractions were collected and evaporated. The residue was dissolved in ethanol and treated with an excess of glacial acetic acid. The solvent was evaporated, and the salt was crystallized from ethyl acetate to give 11.4 g (72%) of product, mp 109°–111° C.

ANALYSIS: Calculated for $C_{20}H_{33}NO_4S$: 62.63%C 8.67%H 3.65%N Found: 62.46%C 8.41%H 3.63%N

EXAMPLE 111 erythro-1-[5-(1-Undecynyl)-2-thienyl]-1-(2-phenyl-4-oxazolinyl)methanol

A solution of erythro-2-amino-1-[5-(1-undecynyl)-2-thienyl]-1,3-propanediol (5.00 g), milled potassium carbonate (0.33 g), glycerol (5 ml), and ethylene glycol (10 ml) was heated to 110° C., with stirring. Benzonitrile (2.66 g) was added, and the solution was stirred at 110° C., under nitrogen, overnight. The reaction mixture was poured into water (300 ml) and extracted with ethyl acetate. The combined organic extracts were dried over anhydrous sodium sulfate, filtered, and the filtrate was evaporated. The residue was flash chromatographed (silica; 3:1 hexane ethyl acetate). The appropriate fractions were collected and evaporated. The residue was recrystallized from ether-hexane to give 4.6 g (73%) of product, mp 99°–100° C.

ANALYSIS: Calculated for $C_{25}H_{31}NO_2S$: 73.31%C 7.63%H 3.42%N Found: 73.17%C 7.60%H 3.37%N

EXAMPLE 112 erythro-N-[1-[4-(1-Dodecenyl)-2-thienyl]-1,3-dihydroxy-2-propyl]acetamide

A solution of ethyl erythro-2-acetamido-3-[4-(1-dodecenyl)-2-thienyl]-3-hydroxypropionate (10.0 g) in dry tetrahydrofuran (50 ml) was stirred at 0° C. under nitrogen as 2.0M lithium borohydride (18 ml) in tetrahydrofuran was added dropwise. The reaction mixture was stirred under a nitrogen atmosphere for three hrs, warming to 15° C. A solution of methanol (24 ml), water (20 ml), and acetic acid (3 ml) was added, with cooling in an ice bath. The solution was neutralized with glacial acetic acid and evaporated. The residue was diluted with water (200 ml) and extracted with ethyl acetate. The combined organic extracts were dried over anhydrous sodium sulfate, filtered, and the filtrate was evaporated. The residue was flash chromatographed (silica: 5% methanol/dichloromethane). The appropriate fractions were collected and evaporated. The residue was crystallized from ether-hexane and then triturated with hexane to give 6.9 g (77%) of product, mp 87°–90° C.

ANALYSIS: Calculated for $C_{21}H_{35}NO_3S$: 66.10%C 9.25%H 3.67%N Found: 66.25%C 9.24%H 3.68%N

EXAMPLE 113

Ethyl erythro-2-acetamido-3-hydroxy-3-[5-(1-tridecynyl)-2-thienyl]-propionate

A solution of 5-(1-tridecynyl)-2-thiophenecarboxaldehyde (49.6 g), acetamidomalonic acid monoethyl ester (35.5 g) and triethylamine (26 ml) in dry tetrahydrofuran (175 ml) was stirred, under nitrogen, at ambient temperature for 3.5 days. Additional amounts of acetamidomalonate monoethyl ester (32.3 g) and triethylamine (24 ml) were added, and the mixture was stirred for 6 days. The reaction mixture was evaporated, and the residue was dissolved in ethyl acetate, washed with brine, dried over anhydrous magnesium sulfate, filtered, and the filtrate was concentrated. The residue was recrystallized twice from hexane:ethyl acetate/1:1, then from ethyl acetate to give 25.7 g (34.5%) of product, mp 83°–84.5° C.

ANALYSIS: Calculated for $C_{24}H_{37}NO_4S$: 66.17%C 8.56%H 3.22%N Found: 66.06%C 8.98%H 3.12%N

EXAMPLE 114 erythro-N-{1,3-Dihydroxy-1-[5-(1-tridecynyl)-2-thienyl]-2-propanyl}acetamide

To a solution of ethyl erythro-2-acetamido-3-hydroxy-3-[5-(1-tridecynyl)-2-thienyl]propionate (34.8 g) in dry tetrahydrofuran (250 ml) was added slowly 2.0M lithium borohydride tetrahydrofuran (40 ml) at 0° C., under nitrogen, with stirring at ambient temperature overnight. The reaction mixture was chilled, and methanol/water/1:1 (50 ml) was added slowly followed by glacial acetic acid (5.1 ml) in methanol/water/1:1 (50 ml). The solution was stirred at ambient temperature for 1 hr, evaporated, and the residue was azeotroped with methanol. Saturated sodium bicarbonate solution was added until pH 8 was obtained, and the mixture was extracted with ethyl acetate. The extracts were dried over anhydrous magnesium sulfate, filtered, and the filtrate was concentrated. The residue was flash chromatographed on silica gel eluting with ethyl acetate methanol (0.5% to 2%). The appropriate fractions were collected and evaporated. The residue was recrystallized from ethyl acetate to give 23.4 g (74.4%) of product, mp 94°–95° C.

ANALYSIS: Calculated for $C_{22}H_{35}NO_3S$: 67.14%C 8.96%H 3.56%N Found: 67.37%C 9.49%H 3.57%N

EXAMPLE 115 erythro-2-Amino-1-[5-(1-tridecynyl)-2-thienyl]-1,3-propanediol acetate

A mixture of erythro-N-{1,3-dihydroxy-1-[5-(1-tridecynyl)-2-thienyl]-2-propanyl}acetamide (11.8 g), 2N sodium hydroxide solution (105 ml), and ethanol (70 ml) was heated at 60° C, under nitrogen, for 22 hrs. The reaction mixture was cooled and extracted with chloroform. The extracts were washed with saturated sodium chloride solution, dried over anhydrous magnesium sulfate, filtered, and the filtrate was evaporated. The residue was chromatographed on silica gel eluting with chloroform/methanol/2N ammonium hydroxide/950:50:3 to 925:75:4. The appropriate fractions were collected and evaporated. The residue was dissolved in ethyl acetate (100 ml), acetic acid (1.5 ml) was added, and the mixture was chilled to yield 10.0 g (81.1%) of product, mp 106°–108° C.

ANALYSIS: Calculated for $C_{20}H_{33}NO_2S \cdot C_2H_4O_2$: 64.20%C 9.06%H 3.40%N Found: 63.87%C 8.96%H 3.35%N

EXAMPLE 116

Ethyl erythro-2-acetamido-3-[2-(1-dodecynyl)-4-thienyl]-3-hydroxypropionate

A solution of 2-(1-dodecynyl)-4-thiophenecarboxaldehyde (27.6 g), acetamidomalonic acid monoethyl ester (18.9 g), and triethylamine (11.1 ) in dry tetrahydrofuran (100 ml) was stirred, under nitr... for 1 week. Acetamidomalonic acid monoethyl ester ... g) and triethylamine (11.1 g) were added in two porti... ver the next three days, and the reaction mixture was ... d an additional week. The reaction mixture was eva... d, ethyl acetate was added, and the mixture was was... with saturated sodium bicarbonate solution and sodi... hloride solution, dried over magnesium sulfate, filter... nd the filtrate was concentrated. The residue was r... stallized from heptane/ethyl acetate/2:1 to give 15.3 ... 36.3%) of the product, mp 71°–72.5° C.

ANALYSIS: Calculated for $C_{23}H_{35}NO_4S$: 65.53%C 8.37%H 3.32%N Found: 65.75%C 8.38%H 3.28%N

EXAMPLE 117 erythro-N-{1-[2-(1-Dodecynyl)-4-thienyl]-1,3-dihydroxy-2-propanyl}acetamide

To a solution of ethyl erythro-2-acetamido-3-[2-(1-dodecynyl)-4-thienyl]-3-hydroxypropionate (17.7 g) in dry tetrahydrofuran (125 ml) was added slowly 2M lithium borohydride tetrahydrofuran (18 ml) at 4° C., under nitrogen, with stirring. The reaction mixture was stirred at room temperature over the weekend, chilled, and methanol/water/1:1 (30 ml) was added slowly, followed by glacial acetic acid (2.3 ml) in methanol/water/1:1 (30 ml). The solution was stirred at ambient temperature for 1 hr, evaporated, and azeotroped with methanol. Ethyl acetate was added, then saturated sodium bicarbonate solution until a pH 8 was obtained, and the mixture was extracted with ethyl acetate. The organic extracts were dried, filtered, and the filtrate was concentrated. The residue was recrystallized from ethyl acetate to give 9.80 g (61.5%) of product, mp 97.5°–98.5° C.

ANALYSIS: Calculated for $C_{21}H_{33}NO_3S$: 66.45%C 8.76%H 3.69%N Found: 66.56%C 8.86%H 3.64%N

EXAMPLE 118 erythro-2-Amino-1-[2-(1-dodecynyl)-4-thienyl]-1,3-propanediol

A mixture of erythro-N-{1-[2-(1-dodecynyl)-4-thienyl]-1,3-dihydroxy-2-propanyl}acetamide (10.4 g), 2N sodium hydroxide solution (69 ml) and ethanol solution (35 ml) was heated at 60° C., under nitrogen, for 22 hrs. The reaction mixture was cooled, water was added, and the mixture was extracted with chloroform. The extracts were washed with brine, dried over magnesium sulfate, filtered, and the filtrate was evaporated. The residue was chromatographed on silica gel, eluting with chloroform/methanol/2N ammonium hydroxide/950:50:3 to 925:75:4. The appropriate fractions were collected and evaporated to give 7.47 g (81%) of product. A 1.8 g-portion of the product was recrystallized from ethyl acetate to yield the analytical sample, mp 69°–70° C.

ANALYSIS: Calculated for $C_{19}H_{31}NO_2S$: 67.61%C 9.26%H 4.15%N Found: 67.94%C 9.42%H 4.11%N

EXAMPLE 119 erythro-2-Amino-1-[2-(1-dodecynyl)-4-thienyl]-1,3-propanediol acetate

A mixture of erythro-N-{1-[2-(1-dodecynyl)-4-thienyl]-1,3-dihydroxy-2-propanyl}acetamide (10.4 g), 2N sodium hydroxide solution (69 ml), and ethanol (35 ml) was heated at 60° C., under nitrogen, for 22 hrs. The reaction mixture was cooled, water was added, and the mixture was extracted with chloroform. The extracts were washed with brine, dried over anhydrous magnesium sulfate, filtered, and the filtrate was evaporated. The residue was chromatographed on silica gel, eluting with chloroform methanol 2N ammonium hydroxide solution/950:50:3 to 925:75:4. The appropriate fractions were collected and evaporated to give 7.47 g (81%) of product as the free base. A 1.9 g-portion was dissolved in ethyl acetate, acetic acid (0.32 ml) was added, and the solution was chilled to yield 1.9 g (69.2%) of product, mp 124°–125° C.

ANALYSIS: Calculated for $C_{21}H_{35}NO_4S$: 63.44%C 8.87%H 3.52%N Found: 63.35%C 8.81%H 3.35%N

EXAMPLE 120 erythro-2-Amino-1-[2-(1-dodecynyl)-4-thienyl]-1,3-propanediol maleate

A solution of erythro-N-{1-[2-(1-dodecynyl)-4-thienyl]-1,3-dihydroxy-2-propanyl}acetamide (10.4 g), 2N sodium hydroxide solution (69 ml), and ethanol (35 ml) were heated at 60° C., under nitrogen, for 22 hrs. The reaction mixture was cooled, water was added, and the mixture was extracted with chloroform. The extracts were washed with brine, dried over anhydrous magnesium sulfate, filtered, and the filtrate was evaporated. The residue was chromatographed on silica gel, eluting with chloroform/methanol/2N ammonium hydroxide solution/950:50:3 to 925:75:4. The appropriate fractions were collected and evaporated to give 7.47 g (81%) of product as the free base. A 1.7 g-portion was dissolved in ethyl acetate and maleic acid (0.58 g) was added. The solution was chilled, and the precipitate was collected to yield 1.9 g (68%) of product, mp 101°–103° C.

ANALYSIS: Calculated for $C_{23}H_{35}NO_6S$: 60.90%C 7.78%H 3.09%MN Found: 60.98%C 7.78%H 3.11%N

EXAMPLE 121 erythro-N-{1-[5-(5-Dodecynyl)-2-thienyl]-1,3-dihydroxy-2-propanyl}-N-ethylacetamide To erythro-N-{1-[5-(1-dodecynyl)-2-thienyl]-1,3-dihydroxy-2-propanyl}acetamide (2.1 g) in ether/tetrahydrofuran/4:1 (100 ml) was added lithium aluminum hydride (0.21 g) at 5° C., under nitrogen, and the mixture was stirred at ambient temperature overnight. Additional amounts of lithium aluminum hydride (0.21, 0.33, and 0.21 g) were added. The mixture was chilled, and saturated ammonium chloride solution was added. The pH was adjusted to 8.5 with 7.5% sodium bicarbonate solution, and the solution was extracted with ethyl acetate. The extracts were washed with brine, dried over magnesium sulfate, filtered, and the filtrate was concentrated. The reside was flash chromatographed on silica gel, eluting with chloroform/methanol/2N ammonium hydroxide solution/960:40:2.5. The appropriate fractions were evaporated to give 1.3 g of a mixture of erythro-1-[5-(1-dodecynyl)-2-thienyl]-2-N-ethylamino-1,3-propanediol and starting material (about 6:1).

To the mixture (1.3 g) was added acetic anhydride (2.3 g), triethylamine (3.4 g), and 4-dimethylaminopyridine (0.05 g) in tetrahydrofuran (30 ml), and the mixture was stirred overnight. The mixture was evaporated, azeotroped with toluene, warmed with methanol for 20 mins, and reevaporated. Water and 7.5% sodium bicarbonate solution were added to pH 8.5, and the mixture was extracted with chloroform. The extracts were washed with brine, dried over magnesium sulfate, filtered, and the filtrate was concentrated. The residue was flash chromatographed on silica gel, eluting with heptane/ethyl acetate/4:1 to 2:1. The appropriate fractions were collected and evaporated to give 1.5 g (73% yield, 44.4% for 2 steps) of erythro-N-{1,3-diacetyloxy-1-[5-(1-dodecynyl)-2-thienyl]-2-propanyl}-N-ethylacetamide.

A mixture of erythro-N-{1,3-diacetyloxy-1-[5-(1-dodecynyl)-2-thienyl]-2-propanyl}-N-ethylacetamide (1.4 g), anhydrous potassium carbonate (0.04 g) in methanol (25 ml) was allowed to stand for 3 hrs. Water was added and the mixture was extracted with dichloromethane. The extracts were washed with brine, dried over magnesium sulfate, filtered, and the filtrate was concentrated. The residue was chromatographed on a silica gel column eluting with ethyl acetate to give 0.93 g (81.6% yield, 36.6% overall for 3 steps) of product.

ANALYSIS: Calculated for $C_{23}H_{37}NO_3S$: 67.77%C 9.15%H 3.44%N Found: 67.24%C 9.45%H 3.31%N

EXAMPLE 122 erythro-2-Amino-1-[5-(dodecynyl)-2-thienyl]1,3-propanediol acetate

A solution of erythro-N-{1,3-dihydroxy-1-[5-(1-dodecynyl)-2-thienyl]-2-propanyl}acetamide (45.6 g), 2N sodium hydroxide solution (300 ml), and ethanol (150 ml) was heated at 60° C., under nitrogen, for 20 hrs. The reaction mixture was cooled, extracted with chloroform, and the extract was washed with saturated sodium chloride solution, dried over anhydrous magnesium sulfate, filtered, and the filtrate was evaporated. The residue was chromatographed on silica gel, eluting with chloroform/methanol/2N ammonium hydroxide/900:100:5. The appropriate fractions were collected and evaporated to give 38.3 g (94.5%) of product as the free base. A 3.3 g-portion of product free base was dissolved in ethyl acetate, acetic acid (0.6 ml) was added, and the solution was chilled to yield 3.3 g (80.2% yield) of product, mp 113°–116°.

ANALYSIS: Calculated for $C_{19}H_{31}NO_2S.C_2H_4O_2$: 63.44%C 8.87%H 3.52%N Found: 63.37%C 8.95%H 3.51%N

EXAMPLE 123 erythro-2-Amino-1-[5-(1-dodecynyl)-2-thienyl]-1,3-propanediol

A solution of erythro-N-{1-[5-(1-dodecynyl)-2-thienyl]-1,3-dihydroxy-2-propanyl}acetamide (22.8 g), 2N sodium hydroxide solution (150 ml), and ethanol (75 ml) was heated at 60° C., under nitrogen, for 19 hrs. The reaction mixture was cooled, water was added, and the mixture was extracted with chloroform. The extracts were washed with brine, dried over anhydrous magnesium sulfate, filtered, and the filtrate was evaporated. The residue was chromatographed on silica gel, eluting with chloroform/methanol/2N ammonium hydroxide/925:75:4 to 900:100:5. The appropriate fractions were collected and evaporated to give 18.6 g (92%) of product free base. A 5 g-portion of product free base was dissolved in ethyl acetate, hydrochloric acid (1.4 ml) in ethanol was added, and the solution was evaporated. The residue was recrystallized from ethyl acetate to yield 4.4 g (73.4%) of product, mp 163°–167° C.

ANALYSIS: Calculated for $C_{19}H_{31}NO_2S.HCl$: 61.02%C 8.62%H 3.75%N Found: 60.74%C 8.89%H 3.73%N

EXAMPLE 124 erythro-2-Amino-1-[5-(1-dodecynyl)-2-thienyl]-1,3-propanediol maleate

A solution of erythro-N-{1-[5-(1-dodecynyl)-2-thienyl]-1,3-dihydroxy-2-propanyl}acetamide (22.8 g), 2N sodium hydroxide solution (150 ml), and ethanol (75 ml) was heated at 60° C., under nitrogen, for 19 hrs. The reaction mixture was cooled, water was added, and the solution was extracted with chloroform. The extracts were washed with brine, dried over magnesium sulfate, filtered, and the filtrate was evaporated. The residue was chromatographed on silica gel, eluting with chloroform/methanol/2N ammonium hydroxide 925:75:4 to 900:100:5. The appropriate fractions were collected and evaporated to give 18.6 g (92%) of product free base. A 9 g-portion of product free base was dissolved in ethyl acetate, maleic acid (3.1 g) was added, and the solution was chilled to yield 10.9 g (83.2% yield) of product, mp 120°–121° C.

ANALYSIS: Calculated for $C_{19}H_{31}NO_2S.C_4H_4O_4$: 60.90%C 7.78%H 3.09%N Found: 60.89%C 7.94%H 2.97%N

EXAMPLE 125 erythro-1-[5-(1-Dodecynyl)-2-thienyl]-2-ethylamino-1,3-propanediol

To a solution of erythro-N-{1,3-dihydroxy-1-[5-(1-dodecynyl)-2-thienyl]-2-propanyl}acetamide (11.9 g) in dry tetrahydrofuran (240 ml) chilled to 5° C., lithium aluminum hydride (1.2 g) was added slowly over 2 hrs, under nitrogen. The mixture was allowed to warm to room temperature and was stirred overnight. Lithium aluminum hydride (2.4 g) was added at room temperature during the next day, and the mixture was stirred for three days. The reaction mixture was chilled, quenched with saturated ammonium chloride solution to pH 8, and the mixture was extracted with ethyl acetate. The organic extracts were washed with brine, dried over anhydrous magnesium sulfate, filtered, and the filtrate was concentrated. The residue product was chromatographed twice on silica gel eluting with chloroform/methanol/2N ammonium hydroxide/970:30:2. The appropriate fractions were collected and concentrated to give 1.5 g (13.2%) of product, mp 48°–50° C.

ANALYSIS: Calculated for $C_{21}H_{35}NO_2S$: 69.00%C 9.65%H 3.83%N Found: 69.00%C 9.61%H 3.82%N

EXAMPLE 126 erythro-1,1-Dimethylethyl-N-{1-[5-(1-dodecynyl)-2-thienyl]-1,3-dihydroxy-2-propanyl}-N-methylcarbamate To a solution of erythro-1,1-dimethylethyl-N-{1,3-diacetyloxy-1-[5-(1-dodecynyl)-2-thienyl-2-propanyl}carbamate (8.24 g) in dry dimethylformamide (90 ml) sodium hydride (0.52 g, 80% immersion in oil) was added with stirring, under nitrogen. The mixture was stirred for 30 mins. Methyl iodide (2.47 g) was added, and the mixture was stirred at ambient temperature overnight. The reaction mixture was concentrated, water and 7.5% sodium bicarbonate were added to pH 8.5, and the mixture was extracted with chloroform. The extracts were filtered, washed with brine, dried over magnesium sulfate, filtered, and the filtrate was concentrated to provide erythro-1,1-dimethylethyl-N-{1-[5-(1-dodecynyl)-2-thienyl]-1,3-diacetyloxy-2-propanyl}-N-methyl carbamate.

A mixture of the erythro-1,1-dimethylethyl-N-{1-[5-(1-dodecynyl)-2-thienyl]- 1,3-diacetyloxy-2-propanyl}-N-methyl carbamate in methanol (150 ml) and potassium carbonate (0.44 g) was stirred for 3 hrs. The mixture was washed with brine, dried over magnesium sulfate, filtered, and the filtrate was evaporated. The residue was combined with the residue from similar reactions carded out on 18.6 mmol scales and flash chromatographed twice on silica gel eluting with heptane/ethyl acetate/2:1. The appropriate fractions were collected and evaporated to give 2.0 g (13.0%) of product.

ANALYSIS: Calculated for $C_{25}H_{41}NO_4S$: 66.48%C 9.15%H 3.10%N Found: 66.26%C 9.29%H 2.98%N

EXAMPLE 127 erythro-1,1-Dimethylethyl-N-{1,3-diacetyloxy-1-[5-(1-dodecynyl)-2-thienyl]-2-propanyl}carbamate A solution of erythro-1,1-dimethylethyl-N-{1-[5-(1-dodecynyl)-2-thienyl]-1,3-dihydroxy-2-propanyl}carbamate (7.7 g), acetic anhydride (7.2 g), triethylamine (10.7 g),and 4-dimethylaminopyridine (0.22 g) in tetrahydrofuran (100 ml) was allowed to stand at room temperature for 1 hr. The reaction mixture was evaporated. The residue was warmed with methanol for 20 min, and the solution was evaporated. Water was added to the residue, the pH adjusted with saturated sodium bicarbonate solution and ammonium hydroxide to pH 8.5, and the solution was extracted with chloroform. The extracts were washed with brine, dried over anhydrous magnesium sulfate, filtered, and the filtrate was concentrated. The residue was flash chromatographed on silica gel eluting with heptane/ethyl/acetatec/9:1. The appropriate fractions were collected and evaporated to give 5.2 g (55.9%) of product, mp 85°–86.5° C.

ANALYSIS: Calculated for $C_{28}H_{43}NO_6S$: 64.46%C 8.31%H 2.68%N Found: 64.69%C 8.48%H 2.68%N

EXAMPLE 128 erythro-4-{[5-(1-Dodecynyl)-2-thienyl]hydroxymethyl}-2-oxazolidinone

To erythro-1,1-dimethylethyl-N-{1,3-diacetyloxy-1-[5-(1-dodecynyl)-2-thienyl]-1-propanyl}carbamate (8.24 g) dissolved in dimethylformamide (90 ml), under nitrogen, was added sodium hydride (0.52 g, 80% immersion in oil), with stirring, over 30 mins, followed by methyl iodide (2.47 g). The reaction mixture was stirred at room temperature overnight and evaporated. Water and 7.5% sodium bicarbonate solution were added to pH 8.5, and the mixture was extracted with chloroform. The extracts were washed with brine, dried over magnesium sulfate, filtered, and the filtrate was concentrated. To the residue in methanol (150 ml) was added and potassium carbonate (0.44 g), with stirring over 3 hrs. The mixture was extracted with chloroform. The extracts were washed with brine, dried over magnesium sulfate, filtered, and the filtrate was evaporated. The residue was flash chromatographed twice on silica gel, eluting with heptane/ethyl acetate/2:1. The appropriate fractions were collected and evaporated. The residue was recrystallized for heptane/ethyl acetate/6:1 to give 0.37 g (4.0%) of product, mp 101°–103° C.

ANALYSIS: Calculated for $C_{21}H_{31}NO_3S$: 66.81%C 8.28%H 3.71%N Found: 67.10%C 8.21%H 3.64%N

EXAMPLE 129

Ethyl threo-2-acetamido-3-[4-(1-dodecynyl)-2-thienyl]-3-hydroxypropionate

A mixture of ethyl threo-5-[4-(1-dodecynyl)-2-thienyl]-2-methyl-4,5-dihydro-4-oxazolecarboxylate (3.90 g) and 50% of aqueous acetic acid (100 ml) was stirred at 50° C. overnight. The reaction mixture was cooled to room temperature, and the pH was adjusted to 6 with sodium bicarbonate solution. The suspension was extracted with ethyl acetate, dried over anhydrous sodium sulfate, filtered, and the filtrate was evaporated. The residue was recrystallized from ether and from ethyl acetate heptane to give 3.7 g (91%) of product, mp 102°–103° C.

ANALYSIS: Calculated for $C_{23}H_{35}NO_4S$: 65.53%C 8.37%H 3.32%N Found: 65.05%C 8.44%H 3.29%N

EXAMPLE 130 erythro-N-[1-[4-(1-Dodecynyl)-2-thienyl]-1,3-dihydroxy-2-propyl]acetamide

A solution of ethyl erythro-2-acetamido-3-[4-(1-dodecynyl)-2-thienyl]-3-hydroxypropionate (3.70 g) in dry tetrahydrofuran (100 ml) was stirred at 0° C., under nitrogen, as lithium borohydride (2.0M, tetrahydrofuran) (5.7 ml) was added dropwise. The reaction mixture was stirred under a nitrogen atmosphere for three hrs, cooled to 0° C., and methanol (20 ml), water (20 ml), acetic acid (3 ml) solution was added dropwise. The solution was neutralized with glacial acetic acid and evaporated. The residue was diluted with water (200 ml) and extracted with ethyl acetate. The combined organic extracts were dried over anhydrous sodium sulfate, filtered, and the filtrate was evaporated. The residue was flash chromatographed (silica; 4% methanol dichloromethane). The appropriate fractions were collected and evaporated. The residue was crystallized from ether to give 2.4 g (72%) of product, mp 69°–72° C.

ANALYSIS: Calculated for $C_{21}H_{33}NO_3S$: 66.45%C 8.76%H 3.69%N Found: 66.43%C 8.81%H 3.69%N

EXAMPLE 131 threo-2-Amino-1-[4-(1-dodecynyl)-2-thienyl]-1,3-propanediol maleate

A solution of threo-N-[1-[4-(dodecynyl)-2-thienyl]-1,3-dihydroxy-2-propyl]acetamide (1.53 g), 2N sodium hydroxide solution (100 ml), and 95% ethanol (75 ml) was stirred at 50° C. over the weekend. The reaction mixture was evaporated and the residue diluted with ammonium chloride solution (300 ml). The mixture was extracted with ethyl acetate, and the combined organic extracts were dried over anhydrous sodium sulfate, filtered, and the filtrate was evaporated. The residue was flash chromatographed (silica; 90:9:1 dichloromethane methanol ammonium hydroxide solution). The appropriate fractions were collected and evaporated. The residue was dissolved in ethyl acetate, and maleic acid was added. Heptane was added, and the precipitate was collected and recrystallized from ethyl acetate heptane to give 1.1 g (60%) of product, mp 133°–136° C.

ANALYSIS: Calculated for $C_{23}H_{35}NO_6S$: 60.90%C 7.78%H 3.09%N Found: 60.77%C 7.63%H 3.12%N

EXAMPLE 132 erythro-2-Dimethylamino-1-[4-(1-dodecynyl)-2-thienyl]-1,3-propanediol maleate

A solution of erythro-2-amino-1-[4-(1-dodecynyl)-2-thienyl]-1,3-propanediol (4.00 g), 37% aqueous formaldehyde (9 ml), and acetonitrile (100 ml) was stirred at room temperature for one hr, then sodium cyanoborohydride (2.23 g) and tetrahydrofuran (40 ml) were added, and the reaction mixture was stirred at room temperature for 2.5 hrs. 50%

Aqueous acetic acid was added until the mixture was slightly acidic, and the mixture was stirred 30 mins. The mixture was evaporated, the residue diluted to 400 ml with water, basified with ammonium hydroxide, and the mixture was extracted with chloroform. The extracts were washed with brine, the layers were separated, and the organic phase was dried over anhydrous sodium sulfate, filtered, and the filtrate was evaporated. The residue was flash chromatographed (silica; 8% methanol/dichloromethane). The appropriate fractions were combined and evaporated to give 3.0 g (69%) of product free base. A 1.25 g-sample of product free base was dissolved in ether and treated with maleic acid (1.05 equiv). Ethyl acetate (about 2 ml) was added, then heptane was added to the cloud point, and the suspension was cooled to give 1.2 g of product, mp 59°–61° C.

ANALYSIS: Calculated for $C_{25}H_{39}NO_6S$: 62.34%C 8.16%H 2.91%N Found: 61.95%C 8.12%H 2.90%N

EXAMPLE 133 erythro-N-[1-[4-(1-Dodecynyl)-2-thienyl]-3-hydroxy-1-methoxy-2-propyl]benzamide

A mixture of erythro-4-[[4-(1-dodecynyl)-2-thienyl]-2-methoxymethyl]-2-phenyloxazoline (4.20 g) and 50% aqueous acetic acid (60 ml) was stirred at 50° C. overnight. The reaction mixture was cooled to room temperature, diluted with water (300 ml), and the pH was adjusted to 6 with sodium bicarbonate solution. The suspension was extracted with ethyl acetate. The extracts were dried over anhydrous sodium sulfate, filtered, and the filtrate was evaporated. The residue was flash chromatographed (silica; 2:1 heptane/ethyl acetate). The appropriate fractions were collected and evaporated. The residue was crystallized from ethyl acetate/heptane to give 3.2 g (73%) of product, mp 62°–64° C.

ANALYSIS: Calculated for $C_{27}H_{37}NO_3S$: 71.17%C 8.18%H 3.07%N Found: 71.11%C 8.18%H 2.89%N

EXAMPLE 134 erythro-2-Amino-3-[4-(1-dodecynyl)-2-thienyl]-3-methoxypropanol maleate

A solution of erythro-N-[1-[4-(dodecynyl)-2-thienyl]-3-hydroxy-1-methoxy-2-propyl]benzamide (2.10 g), 2N sodium hydroxide solution (100 ml), and 95% ethanol (75 ml) was stirred at 70° C. for two days. The reaction mixture was evaporated, the residue diluted with ammonium chloride solution (300 ml), and extracted repeatedly with ethyl acetate. The combined organic extracts were dried over anhydrous sodium sulfate, filtered, and the filtrate was evaporated. The residue was flash chromatographed (silica, 8% methanol dichloromethane). The appropriate fractions were collected and evaporated. Maleic acid was added to the residue dissolved in ethyl acetate. Heptane was added. The precipitate was collected and recrystallized from ethyl acetate to give 1.4 g (65%) of product, mp 108°–109° C.

ANALYSIS: Calculated for $C_{24}H_{37}NO_6S$: 61.64%C 7.89%H 3.00%N Found: 61.61%C 7.67%H 2.67%N

EXAMPLE 135 erythro-1-[4-(1-Dodecynyl)-2-thienyl]-1-(2-phenyl-4-oxazolinyl)methanol

A solution of erythro-2-amino-1-[4-(1-dodecynyl)-2-thienyl]-1,3-propanediol (10.0 g), milled potassium carbonate (0.63 g), glycerol (15 ml) and ethylene glycol (15 ml) was heated to 100° C., with stirring. Benzonitrile (5.09) was added, and the solution was stirred at 110° C., under nitrogen, overnight. The reaction mixture was poured into water (500 ml) and extracted with ethyl acetate. The combined organic extracts were dried over anhydrous sodium sulfate, filtered, and the filtrate was evaporated. The residue was purified by flash chromatography (silica; 5:2 heptane/ethyl acetate). The appropriate fractions were collected and evaporated. The residue was recrystallized from ether to give 8.0 g (64%) of product, mp 105°–107° C.

ANALYSIS: Calculated for $C_{26}H_{33}NO_2S$: 73.72%C 7.85%H 3.31%N Found: 73.74%C 7.94%H 3.28%N

EXAMPLE 136 erythro-4-[[4-(1-Dodecynyl)-2-thienyl]methoxymethyl]-2-phenyloxazoline

A solution of erythro-1-(1-dodecynyl)-2-thienyl]-1-(2-phenyl-4-oxazolinyl)methanol (4.30 g) in dry dimethylformamide (75 ml) was stirred at room temperature, under nitrogen, as sodium hydride (256 mg) was added. The reaction mixture was stirred, under nitrogen, at room temperature for one hr, and dimethylsulfate (1.34 g) was added dropwise. The mixture was stirred at room temperature, under nitrogen, for one hr, poured into ammonium chloride solution (400 ml), and extracted with ethyl acetate. The extracts were dried over anhydrous sodium sulfate, filtered, and the filtrate was evaporated. The residue was flash chromatographed (silica; dichloromethane). The appropriate fractions were collected and evaporated. The residue was distilled in a kugelrohr (oven temperature=100° C./0.05 mm Hg) to give 2.7 g (61%) of product.

ANALYSIS: Calculated for $C_{27}H_{35}NO_2S$: 74.10%C 8.06%H 3.20%N Found: 73.92%C 8.05%H 3.26%N

EXAMPLE 137 erythro-2-Methylamino-1-[4-(1-dodecynyl)-2-thienyl]-1,3-propanediol maleate

A mixture of erythro-1-[4-(1-dodecynyl)-2-thienyl]-1-(2-phenyl-4-oxazolinyl)methanol (3.00 g), iodomethane (3.02 g), and dimethylsulfoxide (35 ml) was stirred at 30° C., under nitrogen, for seven days. The reaction mixture was evaporated, 2N sodium hydroxide solution (45 ml) was added, and reaction mixture was stirred at 60° C. overnight. The mixture was poured into ammonium chloride solution (400 ml) and extracted with ethyl acetate. The combined organic extracts were dried over anhydrous sodium sulfate, filtered, and the filtrate was evaporated. The residue was flash chromatographed (silica; 90:9:1 dichloromethane methanol ammonium hydroxide solution). The appropriate fractions were collected and evaporated. Maleic acid in ethyl acetate was added to the residue. Heptane was added, and the salt was collected and recrystallized from ethyl acetate heptane to give 1.9 g (57%) of product, mp 59°–61° C.

ANALYSIS: Calculated for $C_{24}H_{37}NO_6S$: 61.64%C 7.98%H 3.00%N Found: 61.08%C 7.98%H 2.83%N

EXAMPLE 138 erythro-2-Dimethylamino-3-[4-(1-dodecynyl)-2-thienyl]-3-methoxy-1-propanol maleate A solution of erythro-2-dimethylamino-1-[4-(1-dodecynyl)-2-thienyl]-1,3-propanediol (3.40 g) in dry dimethylformamide (75 ml) was stirred at room temperature, under nitrogen, as sodium hydride (234 mg) was added. The reaction mixture was stirred under nitrogen at room temperature for two hrs, and dimethylsulfate (1.23 g) was added dropwise. The mixture was stirred at room temperature, under nitrogen, for two hrs, poured into ammonium chloride solution (400 ml), and extracted with ethyl acetate. The extracts were dried over anhydrous sodium sulfate, filtered, and the filtrate was evaporated. The residue was flash chromatographed (silica; 4% methanol/dichloromethane). The appropriate fractions were collected and evaporated. Maleic acid in ethyl acetate and heptane were added to the residue. The precipitate was collected and recrystallized from ethyl acetate/heptane to give 2.2 g (48%) of product, mp 69°–71° C.

ANALYSIS: Calculated for $C_{26}H_{41}NO_6S$: 63.00%C 8.34%H 2.83%N Found: 62.88%C 8.38%H 2.83%N

EXAMPLE 139 erythro-2-Amino-1-[4-(1-dodecynyl)-2-thienyl]-1,3-propanediol maleate

To a solution of erythro-2-amino-1-[4-(1-dodecynyl)-2-thienyl]-1,3-propanediol (1.50 g) in warm ethyl acetate (75 ml) was added a solution of maleic acid (542 mg) in warm ethyl acetate. The solution was cooled and the crystals collected. The crystals were recrystallized from ethyl acetate to give 1.8 g (89%) of product, mp 120°–123° C. (softened).

ANALYSIS: Calculated for $C_{23}H_{35}NO_6S$: 60.90%C 7.78%H 3.09%N Found: 61.05%C 7.86%H 3.11%N

EXAMPLE 140 erythro-2-Amino-1-[4-(1-dodecynyl)-2-thienyl]-1,3-propanediol hydrochloride

A solution of erythro-N-[1-[4-(1-dodecynyl)-2-thienyl]-1,3-dihydroxy-2-propyl]acetamide (40.00 g), 2N sodium hydroxide solution (150 ml), and 95% ethanol (100 ml) was stirred at 50° C. overnight. The reaction mixture was cooled to room temperature and neutralized with glacial acetic acid. The mixture was diluted with ammonium chloride solution (200 ml) and extracted with ethyl acetate. The combined organic extracts were dried over anhydrous sodium sulfate, filtered, and the filtrate was evaporated. The residue was purified by flash chromatography (silica; 90:0:1 dichloromethane/methanol/ammonium hydroxide solution). The appropriate fractions were collected and evaporated. Recrystallization of the residue from ethyl acetate gave 25.2 g (71%) of product free base. A solution of product free base (1.5 g) dissolved in ethyl acetate was stirred at 0° C. as a slight excess of ethereal hydrogen chloride was added dropwise. Heptane was added and the solution was cooled. The solid was collected and recrystallized from ethanol/ethyl acetate to give 1.2 g of product, mp 115° C. (softened), 190° C. (dec).

ANALYSIS: Calculated for $C_{19}H_{32}ClNO_2S$: 61.02%C 8.62%H 3.75%N Found: 61.35%C 8.69%H 3.66%N

EXAMPLE 141 erythro-2-[1-[4-(1-Dodecynyl)-2-thienyl]-1,3-dihydroxy-2-propyl]-1H-isoindole-1,3(2H)-dione A mixture of erythro-2-amino-1-[4-(1-dodecynyl)-2-thienyl]-1,3-propanediol (6.00 g) and phthalic anhydride (3.29 g) was stirred at 150° C., under nitrogen, and then placed under high vacuum for 15 mins, with stirring. The reaction mixture was cooled, the vacuum was released, and the residue was flash chromatographed (silica: 2% methanol/dichloromethane). The appropriate fractions were collected, combined, and concentrated to give 6.2 g (75%) of product. A sample was purified on a chromatotron (silica; 5:2 heptane/ethyl acetate) to yield the analytical sample, as an oil after drying under vacuum.

ANALYSIS: Calculated for $C_{27}H_{33}NO_4S$: 69.35%C 7.11%H 3.00%N Found: 69.07%C 7.36%H 2.83%N

EXAMPLE 142

2-(1-Dodecynyl)-4-thiophenecarboxaldehyde

A solution of 2-bromo-4-thiophenecarboxaldehyde (45.3 g), 1-dodecyne (43.4 g), and triethylamine (99 ml), in dry tetrahydrofuran (250 ml) was chilled to 5° C. and degassed under nitrogen. bis(Triphenylphosphine)palladium(II)chloride (1.66 g) and copper(I)iodide (0.23 g) were added to the reaction mixture. The mixture was degassed and stirred overnight, under nitrogen, as it was allowed to warm to room temperature. The precipitate was filtered off, washed with ethyl acetate, and the filtrate was evaporated. Ethyl acetate was added to the residue. The solution was washed with brine, dried over magnesium sulfate, filtered, and the filtrate was concentrated. The residue was chromatographed through a silica gel pad eluting with heptane/1% ethyl acetate. The appropriate fractions were collected and evaporated. The residue and that from a similar reaction on a 0.05 mole scale were combined and distilled to give 30.7 g (79.5%), bp 181°–185° C. @0.35 mm Hg.

ANALYSIS: Calculated for $C_{17}H_{24}OS$: 73.86%C 8.75%H Found: 73.55%C 8.75%H

EXAMPLE 143

5-(1-Tridecynyl)-2-thiophenecarboxaldehyde

A solution of 5-bromo-2-thiophenecarboxaldehyde (34.4 g), 1-tridecyne (35.7 g), and triethylamine (75 ml) in of dry tetrahydrofuran (200 ml) was degassed under nitrogen. bis(Triphenylphosphine)palladium(II)chloride (1.3 g, 1%) and copper(I)iodide (0.17 g, 0.5%) was added. The reaction mixture was degassed and stirred in a water bath at 20° C. for 1 hr, and then for 2 days at ambient temperature, under nitrogen. The precipitate was collected, washed with ethyl acetate, filtered, and the filtrate was evaporated. The residue was taken up in ethyl acetate, washed with brine, dried over anhydrous magnesium sulfate, filtered, and the filtrate was concentrated. The residue was purified by flash chromatography on silica gel, eluting with hexane:1% ethyl acetate. The appropriate fractions were collected and evaporated to yield 51.6 g of an oil. A 2.0 g-portion was dried under high vacuum at ambient temperature for 4 hrs to give 1.77 g (87.3% yield) of product as an oil.

ANALYSIS: Calculated for $C_{18}H_{26}OS$: 74.43%C 9.02%H Found: 74.87%C 9.31%H

EXAMPLE 144

2-Fluoro-3-(1-dodecynyl)benzaldehyde

To a solution of 7.00 g (27.0 mmol) of 2-(1-dodecynyl)fluorobenzene in tetrahydrofuran (60 ml) at −78° C. was added slowly sec-butyllithium (1.3M, cyclohexane) (21 ml). The mixture was stirred at −78° C. for 30 min, and dimethylformamide (2.8 ml) was added dropwise. The mixture was stirred for 5 min at −78° C. and allowed to warm to room temperature. The mixture was diluted with ethyl acetate and washed with water. The organic phase was separated, dried over anhydrous magnesium sulfate, filtered, and the filtrate concentrated in vacuo. The residue was flash chromatographed on silica gel (eluted with ethyl acetate/heptane/ 1:10). The appropriate fractions were collected and evaporated. The residue was chromatographed a second time over silica gel (eluted with dichloromethane) to afford 7.10 g (91%) of product.

ANALYSIS: Calculated for $C_{19}H_{25}FO$: 79.13%C 8.74%H Found: 79.33%C 9.05%H

EXAMPLE 145

Ethyl erythro-2-acetamido-3-(5-bromo-2-thienyl)-3-hydroxypropionate

5-Bromo-2-thiophenecarboxaldehyde (3.8 g), acetamidomalonic acid monoethyl ester (3.8 g) and triethylamine (2.9 ml) in dry tetrahydrofuran (15 ml) was stirred, under nitrogen, at ambient temperature for 3 days. Additional amounts of the malonate ester (5.7 g) and triethylamine (5.8 ml) were added over the next 2 days, with stirring. The mixture was evaporated, and the residue was dissolved in ethyl acetate. The solution was washed with saturated sodium bicarbonate solution, dried over anhydrous magnesium sulfate, filtered, and the filtrate was concentrated. The residue was chromatographed on silica gel eluting with chloroform. The appropriate fractions were collected and concentrated to give 3.3 g (50%) of the product, mp 118.5°–120.5° C.

ANALYSIS: Calculated for $C_{11}H_{14}BrNO_4S$: 39.30%C 4.20%H 4.17%N Found: 39.56%C 4.06%H 3.81%N

EXAMPLE 146 erythro-N-Methyl-N'-[1-[5-(1-undecynyl)-2-thienyl]-1,3-dihydroxy-2-propyl]urea

To a solution of erythro-2-amino-1-[5-(1-undecynyl)-2-thienyl]-1,3-propanediol (2.5 g) and dry dichloromethane (100 ml) was added methyl isocyanate (0.85 g), and the mixture was stirred at room temperature for 15 mins. The mixture was evaporated. The residue was taken up in ethyl acetate, and the solution was washed with dilute sodium bicarbonate solution and brine, dried over anhydrous magnesium sulfate, filtered, and the filtrate was evaporated. The residue was recrystallized from ethyl acetate hexane to give 2.0 g (67.2%) of product, mp 97°14 99° C.

ANALYSIS: Calculated for $C_{20}H_{32}N_2O_3S$: 63.12%C 8.48%H 7.36%N Found: 63.10%C 8.46%H 7.36%N

EXAMPLE 147 erythro-N-[1-[4-(1-Dodecynyl)-2-thienyl]-3-hydroxy-1-methoxy-2-propyl]-N'-methyl-1,2-benzenedicarboxamide A solution of erythro-2-[1-[4-(1-dodecynyl)-2-thienyl]-3-hydroxy-1-methoxy-2-propyl]-1H-isoindole-1,3(2H)-dione (2.10 g) in dimethylformamide (20 ml) and 40% aqueous methylamine (10 ml) was stirred at room temperature for two hrs. The reaction mixture was poured into water (200 ml), ammonium chloride was added, and the product was extracted with ethyl acetate. The organic extracts were dried over anhydrous sodium sulfate, filtered, and the filtrate was evaporated. The residue was flash chromatographed (silica: 5% methanol dichloromethane). The appropriate fractions were collected and evaporated. The residue was recrystallized from ethyl acetate to give 0.6 g (27%) of product, mp 138°–140° C.

ANALYSIS: Calculated for $C_{29}H_{40}N_2O_4S$: 67.94%C 7.86%H 5.46%N Found: 67.52%C 7.85%H 5.26%N

EXAMPLE 148 erythro-N-[4-(1-Dodecynyl)-2-thienyl]-1-hydroxy-3-(1,1-dimethylethyldimethylsilyloxy)acetamide A solution of ethyl erythro-2-acetamido-3-[4-(1-dodecynyl)-2-thienyl]-3-(1,1-dimethylethyldimethylsilyloxy)propionate (18.4 g) and dry tetrahydrofuran (150 ml) was stirred at 0° C., under nitrogen, as lithium borohydride (22.4 ml, 2.0M in tetrahydrofuran) was added dropwise. The reaction mixture was stirred under a nitrogen atmosphere for three hrs, heated under reflux for two hrs, and cooled to 0° C. Methanol (30 ml), water (30 ml), and acetic acid (5 ml) were added dropwise. The solution was neutralized with glacial acetic acid and evaporated. The residue was diluted with water (200 ml) and extracted with ethyl acetate. The combined organic extracts were dried over anhydrous sodium sulfate, filtered, and the filtrate was evaporated. The residue was flash chromatographed (silica; 3% methanol dichloromethane). The appropriate fractions were collected and evaporated. The residue was crystallized from ethyl acetate to give 7.1 g (42%) of product, mp 135°–136° C.

ANALYSIS: Calculated for $C_{27}H_{47}NO_3SSi$: 65.67%C 9.59%H 2.84%N Found: 66.05%C 9.26%H 2.82%N

EXAMPLE 149

Ethyl erythro-2-acetamido-3-[4-(1-dodecynyl)-2-thienyl]-3-(1,1-dimethylethyldimethylsilyloxy)propionate A solution of ethyl erythro-2-acetamido-3-[4-(1-dodecynyl)-2-thienyl]-3-hydroxypropionate (15.00 g), imidazole (6.06 g), and dry dimethylformamide (75 ml) was stirred at room temperature, under nitrogen, as t-butyldimethylsilyl chloride (6.44 g) was added. The reaction mixture was stirred at 35° C. under a nitrogen atmosphere overnight. The solution was poured into water (500 ml) and extracted with ethyl acetate. The combined organic extracts were dried over anhydrous sodium sulfate, filtered, and the filtrate was evaporated. The residue was flash chromatographed (silica; 4:1 hexane/ethyl acetate). The appropriate fractions were collected and evaporated to give 18.8 g (99%) of product.

ANALYSIS: Calculated for $C_{29}H_{49}NO_4SSi$: 65.00%C 9.22%H 2.61%N Found: 64.95%C 9.26%H 2.57%N

EXAMPLE 150 erythro-N-[1-[4-(1-dodecynyl)-2-thienyl]-1,3-dihydroxy-2-propyl]-N'-octylurea

A solution of erythro-2-amino-1-[4-(1-dodecynyl)-2-thienyl]-1,3-propanediol (3.00 g), dry pyridine (1.05 g), and dry dimethylformamide (50 ml) was stirred at −10° C., under nitrogen, as a solution of octyl isocyanate (1.45 g) in dry dimethylformamide (30 ml) was added dropwise. The reaction mixture was allow to warm to room temperature, with stirring under nitrogen, overnight. The solution was poured into cold water (500 ml), and the solid was collected and dried under vacuum. Recrystallization from ethyl acetate gave 3.6 g (82%) of product, mp 99°–100° C.

ANALYSIS: Calculated for $C_{28}H_{48}N_2O_3S$: 68.25%C 9.82%H 5.68%N Found: 68.36%C 9.73%H 5.67%N

EXAMPLE 151

1-Octanol-erythro-N-[1-[4-(1-dodecynyl)-2-thienyl]-1,3-dihydroxy-2-propyl]carbamate (ester)

A solution of erythro-2-amino-1-[4-(1-dodecynyl)-2-thienyl]-1,3-propanediol (3.00 g), dry pyridine (1.05 g) and dry dimethylformamide (50 ml) was stirred at −10° C., under nitrogen, as a solution of octyl chloroformate (1.80 g) in dry dimethylformamide (30 ml) was added dropwise. The reaction mixture was allow to warm to room temperature overnight, with stirring under nitrogen. The solution was poured into water (500 ml), ammonium chloride solution was added, and the mixture was extracted with ethyl acetate. The combined organic extracts were dried over anhydrous sodium sulfate, filtered, and the filtrate was evaporated. The residue was flash chromatographed (silica; 3–4% methanol dichloromethane). The appropriate fractions were collected and evaporated. The residue was recrystallized from hexane to give 2.6 g (59%) of product, mp 75°14 77° C.

ANALYSIS: Calculated for $C_{28}H_{47}NO_4S$: 68.11%C 9.59%H 2.84%N Found: 68.04%C 9.56%H 2.85%N

EXAMPLE 152 erythro-N-[1-[4-(1-Dodecynyl)-2-thienyl]-1,3-dihydroxy-2-propyl]octanamide

A solution of erythro-2-amino-1-[4-(1-dodecynyl)-2-thienyl]-1,3-propanediol (2.50 g), dry pyridine (0.88 g), and dry dimethylformamide (45 ml) was stirred at −10° C., under nitrogen, as a solution of octanoyl chloride (1.27 g) in dry dimethylformamide (30 ml) was added dropwise. The reaction mixture was allow to warm to room temperature overnight, with stirring under nitrogen. The solution was poured into water (500 ml), ammonium chloride was added, and the mixture was extracted with ethyl acetate. The combined organic extracts were dried over anhydrous sodium sulfate, filtered, and the filtrate was evaporated. The residue was combined with 1.1 g of that previously prepared, and was flash chromatographed (silica; 3–4% methanol/dichloromethane), The appropriate fractions were collected and evaporated. The residue was recrystallized from ethyl acetate to give 3.2 g (61%) of product, mp 98°–100° C.

ANALYSIS: Calculated for $C_{27}H_{45}NO_3S$: 69.93%C 9.78%H 3.02%N Found: 69.71%C 9.84%H 3.00%N

EXAMPLE 153

Ethyl threo-5-[4-(1-dodecynyl)-2-thienyl]-2-methyl-4,5-dihydro-4-oxazolecarboxylate A solution of ethyl erythro-2-acetamido-3-[4-(1-dodecynyl)-2-thienyl]-3-hydroxypropionate (12.00 g), triphenylphosphine (8.21 g) and dry tetrahydrofuran (100 ml) was stirred at 0° C., under nitrogen, as a solution of diethyl azodicarboxylate (5.45 g) in dry tetrahydrofuran (50 ml) was added dropwise. The reaction mixture was stirred for three hrs under a nitrogen atmosphere as it was allowed to warm to 15° C. and was evaporated. The reaction was repeated on the same scale under identical conditions and the residues were combined and flash chromatographed (silica; 3:1 hexane-ethyl acetate). The appropriate fractions were combined and evaporated to give 10.7 g (47%) of product. A sample was purified on a chromatotron (silica; 3:1 heptane-ethyl acetate). The residue was dissolved in heptane, filtered, and the filtrate was evaporated and dried under vacuum to give the analytical sample, as an oil.

ANALYSIS: Calculated for $C_{23}H_{33}NO_3S$: 68.45%C 8.24%H 3.47%N Found: 68.36%C 8.42%H 3.19%N

EXAMPLE 154 erythro-1,1-dimethylethylethyl-N-[5-(1-dodecynyl)-2-thienyl]-1,3-dihydroxy-2-propanylcarbamate A solution of erythro-2-amino-1-[5-(1-dodecynyl)-2-thienyl]-1,3-propanediol (5.1 g) and di-tert-butyldicarbonate (3.4 g) in dichloromethane (150 ml) were stirred at ambient temperature under nitrogen overnight. Diethyl ether (150 ml) was added, and the reaction mixture was washed with saturated sodium bicarbonate solution, and sodium chloride solution, dried over magnesium sulfate, filtered, and the filtrate was evaporated. The residue was recrystallized from heptane:ethyl acetate/1:1 to give 4.6 g (70.4%) of product.

ANALYSIS: Calculated for $C_{24}H_{39}NO_4S$: 65.87%C 8.98%H 3.20%N Found: 66.02%C 9.02%H 2.96%N

EXAMPLE 155 erythro-5-Amino-4-[5-(1-dodecynyl)-2-thienyl]-2,2-dimethyl-1,3-dioxane

A solution of erythro-2-amino-1-[5-(1-dodecynyl)-2-thienyl]-1,3-propanediol (5.1 g), 2,2-dimethoxypropane (15.6 g), p-toluenesulfonic acid (3.1 g), and dichloromethane (100 ml) was stirred at ambient temperature ovenight. Additional 2,2-dimethoxypropane (7.8 g) and p-toluenesulfonic acid (1.5 g) were added, and the mixture was stirred for 3.5 hrs. Saturated sodium bicarbonate solution was added, the mixture was extracted with ethyl acetate, and the extracts were washed with brine, dried over anhydrous magnesium sulfate, filtered, and the filtrate was evaporated. The residue was chromatographed twice on silica gel eluting with chloroform:0.5% methanol to give 1.8 g (32.5%) of product, as an oil.

ANALYSIS: Calculated for $C_{22}H_{35}NO_2S$: 69.98%C 9.34%H 3.71%N Found: 69.97%C 9.45%H 3.64%N

EXAMPLE 156 erythro-2-Dimethylamino-1-[5-(1-dodecynyl)-2-thienyl]-1,3-propanediol

A solution of erythro-2-amino-1-[5-(1-dodecynyl)-2-thienyl]-1,3-propanediol (5.1 g) and 37% formaldehyde (11.3 ml), and acetonitrile (100 ml) was stirred at ambient temperature for 1 hr. Sodium cyanoborohydride (2.8 g) and tetrahydrofuran (40 ml) were added, and the mixture was stirred for 2.5 hrs. Water and glacial acetic acid were added gradually until pH 5 was obtained. The mixture was stirred 30 mins and evaporated. Water was added, the pH was adjusted to 10.5 with ammonium hydroxide solution, and the mixture was extracted with chloroform. The extract was washed with brine, dried over anhydrous magnesium sulfate, filtered, and the filtrate was evaporated. The residue was chromatographed twice on silica gel, eluting with chloroform/methanol/2N ammonium hydroxide solution/970:30:2 to 950:50:3. The appropriate fractions were collected and combined to give 2.3 g (36%) of product, as an oil.

ANALYSIS: Calculated for $C_{21}H_{35}NO_2S$: 69.00%C 9.65%H 3.83%N Found: 69.03%C 9.79%H 3.85%N

EXAMPLE 157 trans-erythro-2-Amino-1-[4-(1-dodecenyl)-2-thienyl]-1,3-propanediol

A solution of erythro-N-[1-[4-(dodecenyl)-2-thienyl]-1,3-dihydroxy-2-propyl]acetamide (5.25 g), 2N sodium hydroxide solution (100 ml), and 95% ethanol (75 ml) was stirred at 50° C. overnight. The reaction mixture was cooled to room temperature and diluted with sodium bicarbonate solution (300 ml). The mixture was extracted repeatedly with ethyl acetate and the combined organic extracts were dried over anhydrous sodium sulfate, filtered, and the filtrate was evaporated. The residue was flash chromatographed (silica; 90:9:1 dichloromethane/methanol/ammonium hydroxide). The appropriate fractions were collected and evaporated. The residue was crystallized from ethyl acetate to give 3.4 g (73%) of product. The analytical sample was obtained by flash chromatography (silica; 8–10% methanol dichloromethane). The appropriate fractions were collected and the residue was recrystallized from ethyl acetate to give 1.9 g (41%) of product, mp 112°–115° C.

ANALYSIS: Calculated for $C_{19}H_{33}NO_2S$: 67.21%C 9.80%H 4.13%N Found: 66.66%C 9.79%H 4.09%N

EXAMPLE 158 erythro-1-[5-(1-Dodecynyl)-2-thienyl]-2-methylamino-1,3-propanediol maleate

A solution of erythro-1,1-dimethylethyl-N-{1-[5-(1-dodecynyl)-2-thienyl]-1,3-dihydroxypropanyl}-N-methylcarbamate (2.0 g) was dissolved in methanol (40 ml) and chilled under nitrogen. Cold saturated hydrogen chloride in methanol (2 ml) was added, and the reaction vessel was stoppered and stirred for 2 days at ambient temperature. The reaction mixture was chilled, the pH was adjusted to 12 with 2N sodium hydroxide solution, and extracted with chloroform and 3:1 chloroform/isopropanol. The extracts were washed with brine, dried over anhydrous magnesium sulfate, filtered, and the filtrate was concentrated. The residue was combined with the residues from similar reactions carried out on a 3.3 mmol scale, and the combined material was flash chromatographed twice on silica gel eluting with chloroform/methanol/2N ammonium hydroxide solution/ 960:40:3. The appropriate fractions were collected and evaporated. The residue was treated with maleic acid in ethyl acetate, and the maleate was recrystallized from cyclohexane to give 1.6 g (44.7%) of product, mp 78°–80° C.

ANALYSIS: Calculated for $C_{20}H_{33}NO_2S \cdot C_4H_4O_4$: 61.64%C 7.98%H 3.00%N Found: 61.40%C 8.17%H 2.90%N

EXAMPLE 159

Ethyl trans-3-[3-(1-Dodecynyl)phenyl]-2-propenoate

To a solution of 3-(1-dodecynyl)benzaldehyde (23.0 g) in toluene (150 ml) was added carbethoxymethylenetriphenylphosphorane (35.5 g) in one portion. The mixture was warmed at 80° C. for 5 hr, allowed to cool to room temperature, and concentrated in vacuo. The residue was flash chromatographed over silica gel (eluted with ethyl acetate/hexane/1:15). The appropriate fractions were collected and evaporated to afford 21.1 g (73%) of product.

ANALYSIS: Calculated for $C_{23}H_{32}O_2$: 81.13%C 9.47%H Found: 81.25%C 9.45%H

EXAMPLE 160

(2S-Trans-3-[3-(1-Dodecynyl)phenyl]oxiranemethanol

To a slurry of 4A molecular sieves (1 g) in dry dichloromethane (50 ml) was added a solution of (+) diisopropyltartrate (524 mg) in dry dichloromethane (10 ml). The mixture was cooled to −20° C. and titanium(IV) isopropoxide (0.53 ml) was added, followed by tert-butyl-hydroperoxide (3.0M, isooctane) (20 ml). The mixture was stirred for 20 mins at −20° C. and a solution trans-3-[3-(1-dodecynyl)phenyl]propen-1-ol (8.88 g) in dry dichloromethane (20 ml) was added slowly by means of syringe. The mixture was stirred for 30 mins at −20° C. and 25% aqueous sodium hydroxide solution (6 ml) and water (40 ml) were added. The mixture was allowed to warm to room temperature and stirred for 30 mins. The organic phase was separated and the aqueous phase was extracted with dichloromethane. The organic phases were combined, dried over anhydrous magnesium sulfate, filtered, and the filtrate was concentrated in vacuo. The residue was flash chromatographed over silica gel (eluted with ethyl acetate/hexane/1:3). The appropriate fractions were collected and evaporated. Crystallization of the residue from hexane afforded 5.61 g (60%) of product, mp 41°–42° C., $[\alpha]_D^{25}$=−31.7 (c. 1.04, chloroform).

ANALYSIS: Calculated for $C_{21}H_{30}O_2$: 80.21%C 9.62%H Found: 80.25%C 9.49%H

EXAMPLE 161

(2S-trans)-3-[3-(1-Dodecynyl)phenyl]epoxypropyl Benzoyl Carbamate

To a solution of (2S-trans)-3-[3-(1-dodecynyl)phenyl]oxiranemethanol (63.1 g) in dry dichloromethane (60 ml) was added a solution of benzoyl isocyanate (3.23 g) in dichloromethane (20 ml). The mixture was stirred for 2 hr at room temperature, diluted with dichloromethane and washed with water. The organic phase was separated, dried over anhydrous magnesium sulfate, and concentrated in vacuo. The residue was chromatographed over silica gel (eluted with ethyl acetate/heptane/1:1). The appropriate fractions were collected and concentrated to afford 9.23 g (99%) of product, $[\alpha]_D^{25}$−31.8° (c. 0.78, chloroform).

ANALYSIS: Calculated for $C_{29}H_{35}NO_4$: 75.46%C 7.64%H 3.03%N Found: 75.10%C 7.62%H 3.14%N

EXAMPLE 162

(2'S,4R)-4-{[3-(1-Dodecynyl)phenyl]-2'-hydroxymethyl}-2-oxazolidinone

To a solution of (2S-trans)-3-[3-(1-dodecynyl)phenyl]epoxypropyl benzoylcarbamate (8.65 g) in tetrahydrofuran (60 ml) was added sodium hydride (215 mg). The mixture was heated under reflux for 30 mins, allowed to cool to room temperature and quenched with 25% aqueous sodium hydroxide solution (8 ml). The mixture was dissolved in ethyl acetate, and the organic phase was washed with water and brine. The organic phase was separated, dried over anhydrous magnesium sulfate, and concentrated in vacuo. The residue was flash chromatographed twice over silica gel (eluted with ethyl acetate/hexane/3:2). The appropriate fractions were collected and evaporated afford 5.10 g (76%) of product, mp 85°–86° C., $[\alpha]_D^{25}$=+7.4° (c. 0.86, chloroform).

ANALYSIS: Calculated for $C_{22}H_{31}NO_3$: 73.92%C 8.74%H 3.92%N Found: 74.08%C 9.03%H 3.80%N

EXAMPLE 163

(2R,3S)-2-Amino-1-[3-(1-dodecynyl)phenyl]-1,3-propanediol acetate

To a solution of (2'S,4R)-4-{[3-(1-dodecynyl)phenyl]-2'-hydroxymethyl}-2'-2-oxazolidone (5.20 g) in ethanol (20 ml) was added 25% aqueous sodium hydroxide (15 ml). The mixture was heated under reflux for 3 hr, allowed to cool to room temperature and stirred overnight. The mixture was diluted with ethyl acetate, and water was added. The aqueous phase was extracted with ethyl acetate. The organic phases were combined, dried over anhydrous magnesium sulfate, filtered, and the filtrate was concentrated in vacuo. The residue was flash chromatographed over silica gel (eluted with chloroform/methanol/9:1 followed by chloroform:methanol/5:1). The appropriate fractions were collected and evaporated to afford 3.9 g (87%) of (2R,3S)-2-amino-1-[3-(1-dodecynyl)phenyl]-1,3-propanediol.

To a solution of the amine in ethyl acetate (10 ml) was added glacial acetic acid (1 ml). The mixture was stirred for 15 mins at room temperature and concentrated in vacuo, then under high vacuum. The residue was crystallized twice from ethyl acetate to afford 1.75 g (29% overall) of product, mp 104°–105° C., $[\alpha]_D^{25}$=+16.8° (c. 0.5, ethanol), ANALYSIS: Calculated for $C_{23}H_{37}O$: 70.55%C 9.52%H 3.58%N Found: 70.33%C 9.50%H 3.54%N

EXAMPLE 164

(2R-trans)-3-[3-(1-Dodecynyl)phenyl]oxiranemethanol

To a solution (−) diisopropyltartrate (524 mg) in dry dichloromethane (60 ml) and 4A molecular sieves (1 g) at −20° C. was added titanium(IV) isopropoxide (0.53 ml) followed by t-butylhydroperoxide (3.0M, isooctane) (20 ml). The reaction mixture was stirred for 20 mins at −20° C. and then a solution of trans-3-[3-(1-dodecynyl)phenyl]propene-1-ol (8.88 g) in dichloromethane (20 ml) was added slowly. The mixture was stirred for 1.5 hr and quenched with 25% aqueous sodium hydroxide (6 ml) followed by water (40 ml). The mixture was allowed to warm to room temperature, and was stirred for 30 min. The organic phase was separated, and the aqueous phase was extracted with dichloromethane. The organic extracts were combined, dried over anhydrous magnesium sulfate, filtered, and the filtrate was concentrated in vacuo. The residue was chromatographed over silica gel (eluted with ethyl acetate/Heptane/1:2). The appropriate fractions were collected and evaporated. The residue was crystallized from heptane to afford 6.5 g (69%) of product, mp 41°–42° C. $[\alpha]_D^{25}$+33.1° (c. 0.725, chloroform).

ANALYSIS: Calculated for $C_{21}H_{30}O_2$: 80.21%C 9.62%H Found: 80.37%C 9.49%H

EXAMPLE 165

(2R-trans))-3-[3-(1-Dodecynyl)phenyl]epoxypropyl Benzoyl Carbamate

To a solution of (2R-trans)-3-[3-(1-dodecynyl)phenyl] oxiranemethanol (11.8 g) and dichloromethane (100 ml) at room temperature was added a solution of benzoyl isocyanate (5.7 g) in dichloromethane (30 ml). The reaction mixture was stirred at room temperature for 30 mins, diluted with dichloromethane (300 ml), and the solution was washed with water. The organic phase was separated, dried over anhydrous magnesium sulfate, filtered, and the filtrate was concentrated in vacuo. The residue was chromatographed over silica gel (eluted with ethyl acetate:Heptane/1:1) to afford 17.5 g (99%) of the product, as an oil, $[\alpha]_D^{25}$+34.4° (c. 0.85, chloroform).

ANALYSIS: Calculated for $C_{29}H_{35}NO_4$: 75.46%C 7.64%H 3.03%N Found: 75.29%C 7.50%H 2.82%N

EXAMPLE 166

(2'R,4S)-4-{[3-(1-Dodecynyl)phenyl]-2'-hydroxymethyl}-2-oxazolidinone

To a solution of (2R-trans)-3-[3-(1-dodecynyl)phenyl] epoxypropyl benzoyl carbamate (16.0 g) and tetrahydrofuran (150 ml) at room temperature was added sodium hydride (400 mg) in one portion. The mixture was heated under reflux for 1.5 hr, allowed to cool to room temperature, and 25% aqueous sodium hydroxide (20 ml) was added over 30 mins, with stirring. The slurry was diluted with ethyl acetate, and the mixture was washed with water and brine. The organic phase was separated, dried over anhydrous magnesium sulfate, filtered, and the filtrate was concentrated in vacuo. The residue was flash chromatographed over silica gel (eluted with ethyl acetate/Heptane/2:1). The appropriate fractions were collected and concentrated to afford 9.90 g (80%) of product, mp 84.5°–86° C., $[\alpha]_D^{25}$−6.8° (c. 0.845, chloroform).

ANALYSIS: Calculated for $C_{22}H_{31}NO_3$: 73.92%C 8.74%H 3.92%N Found: 73.59%C 8.77%H 3.82%N

EXAMPLE 167

(2S,3R)-2-Amino-1-[3-(1-dodecynyl)phenyl]-1,3-propanediol acetate

To a solution of (2R-trans)-4-{[3-(1-dodecynyl)phenyl]-2'-hydroxymethyl}-2-oxazolidinone (5.4 g) in ethanol (40 ml) was added 25% aqueous sodium hydroxide solution (15 ml). The reaction mixture was heated at 80° C. for 4 hr, and then allowed to cool to room temperature. The solution was partitioned between ethyl acetate and water. The organic phase was separated, and the aqueous phase was extracted with ethyl acetate. The organic phases were combined, dried over anhydrous magnesium sulfate, filtered, and the filtrate was concentrated in vacuo. The residue was flash chromatographed over silica gel (eluted with chloroform/methanol/ 9:1 followed by chloroform:methanol/5:1). The appropriate fractions were collected and concentrated to afford 3.24 g of (2S,3R)-2-amino-1-[3-(1-dodecynyl)phenyl]-1,3-propanediol.

To a solution of the amine in ethyl acetate (10 ml) was added glacial acetic acid (0.80 ml). The mixture was stirred for 10 min at room temperature and concentrated in vacuo. The residue was crystallized twice from ethyl acetate to afford 2.35 g (40% for two steps)of product, mp 104°–105° C. $[\alpha]_D^{25}$=−17.3° (c. 0.53, ethanol).

ANALYSIS: Calculated for $C_{23}H_{37}NO_4$: 70.55%C 9.52%H 3.58%N Found: 70.62%C 9.54%H 3.55%N

EXAMPLE 168

(2S,3S)-2-Amino-1-[5-(1-dodecynyl)-2-thienyl]-1,3-propanediol acetate

To a solution of (2S,3S)-1,1-dimethylethyl)-N-(1-[5-(1-dodecynyl)-2-thienyl]-1,3-dihydroxy-2-propanoyl)carbamate (1.77 g) and methanol (20 ml) was added ethanolic hydrogen chloride (5 ml). The reaction mixture was stirred at room temperature for 24 hrs, diluted with ethyl acetate, and washed with 25% aqueous sodium hydroxide solution. The aqueous phase was extracted with ethyl acetate, and the organic phases were combined, dried over magnesium sulfate, filtered, and the filtrate was concentrated in vacuo. The residue was flash chromatographed over silica gel (eluted with chloroform/methanol/7:1) to afford 630 mg (46%) of product as the free base. To a solution of the product free base in ethyl acetate (5 ml) was added glacial acetic acid (0.11 ml). The mixture was cooled to 0° C. The acetate salt crystallized to give 522 mg (70%) of product.

The reaction was repeated on a similar scale to afford 763 mg (40%) of the acetate. The products from the reactions were combined and crystallized from ethyl acetate to give 961 mg of product, mp 114°–118° C., $[\alpha]_D^{25}$=+7° (c. 0.63, ethanol).

ANALYSIS: Calculated for $C_{21}H_{35}NO_4S$: 63.44%C 8.87%H 3.52%N Found: 63.16%C 9.22%H 3.56%N

EXAMPLE 169

(2S,3S)-1,1-dimethylethyl-N-(1-[5-(1-dodecynyl)-2-thienyl]-1,3-dihydroxy-2-propanylcarbamate To a solution of (2S,4S)-1,1-dimethylethyl-4-{[5-(1-dodecynyl)-2-thienyl]-2-hydroxymethyl}-1,2-dimethyl-3-oxazolidinecarboxylate (7.50 g) in methanol (70 ml) was added p-toluenesulfonic acid (1.5 g). The mixture was stirred at room temperature for 1 hr, diluted with ethyl acetate, and washed with water. The aqueous phase was extracted with ethyl acetate, and the organic phases were combined, dried over anhydrous magnesium sulfate, filtered, and the filtrate was concentrated in vacuo. The residue was recrystallized twice from ethyl acetate:heptane/1:2 to afford 5.25 g of product, mp 74°–75° C.; $[\alpha]_D^{25}$=+12.7° (c. 0.74, chloroform).

ANALYSIS: Calculated for $C_{24}H_{39}NO_4S$: 65.87%C 8.98%H 3.20%N Found: 65.98%C 9.01%H 3.19%N

EXAMPLE 170

(2S,4S)-1,1-Dimethylethyl-4-{(5-(1-dodecynyl)-2-thienyl]-2-hydroxymethyl}-2,2-dimethyl-3-oxazolidinecarboxylate To a solution of 2-(1-dodecynyl)thiophene (23.4 g) in tetrahydrofuran (150 ml) at −78° C. was added n-butyllithium (1.52M in hexanes) dropwise by means of an addition funnel. The mixture was stirred for 1.5 hrs at −78° C., and a solution of 1,1-dimethylethyl-(S)-4-formyl-2,2-dimethyl-3-oxazolidinecarboxylate (14.4 g) in tetrahydrofuran (30 ml) was added slowly. The mixture was stirred for 1 hr, diluted with ethyl acetate, and washed with water. The aqueous phase was extracted with ethyl acetate. The organic phases were combined, dried over anhydrous magnesium sulfate, filtered, and the filtrate was concentrated in vacuo. The residue was flash chromatographed over silica gel (eluted with ethyl acetate:heptane/1:7) to afford 22.3 g (74%) of a mixture of diastereomers (4:1/erythro:threo) of product.

To a solution of 22.3 g of the mixture of diastereomers of product in tetrahydrofuran (100 ml) was added acetic anhydride (26.7 ml) followed by triethylamine (54 ml) and 4-dimethylaminopyridine (2.7 g). The mixture was stirred for 2 hr at room temperature, diluted with ethyl acetate, and washed with water. The aqueous phase was extracted with ethyl acetate, the organic phases were combined, dried over anhydrous magnesium sulfate, filtered, and the filtrate was concentrated in vacuo. The residue was flash chromatographed over silica gel (eluted with ethyl acetate:heptane/ 1:14). The appropriate fractions were collected and evaporated to afford 13.4 g (55%) of the pure erythro 1,1-dimethyl-4-{[5-(1-dodecynyl)-2-thienyl]acetoxymethyl}-2,2-dimethyl-3-oxazolidinecarboxylate and 6.2 g (26%) of a mixture of erythro- and threo- isomers.

To a solution of the erythro isomer (13.4 g) in methanol (70 ml) was added potassium carbonate (10.6 g) in one portion. The mixture was stirred for 20 min at room temperature, filtered, and the filter cake was washed with ethyl acetate. The filtrate was concentrated to ⅓ of its original volume, diluted with ethyl acetate, and washed with water. The aqueous phase was extracted with ethyl acetate, and the organic phases were combined, dried over magnesium sulfate, filtered, and the filtrate was concentrated in vacuo to afford 10.34 g (84%) of product, $[\alpha]_D^{25}=+1°$ (c. 1.15, chloroform).

ANALYSIS: Calculated for $C_{27}H_{43}NO_4S$: 67.89%C 9.07%H 2.93%N Found: 68.21%C 9.05%H 2.39%N

EXAMPLE 171

(4S)-3-{(2'S,3'R)-2'-Bromo-3'-hydroxy-3'-[4-(1-dodecynyl)- 2-thienyl]propanoyl}-4-(phenylmethyl)-2-oxazolidinone To a slurry of (4S)-3-(bromoacetyl)-4-(phenylmethyl)-2-oxazolidinone (11.3 g) in diethyl ether (90 ml) at −78° C. was added di-n-butylboron triflate (10.5 ml) followed by triethylamine (7.5 ml). The mixture was stirred for 5 min at −78° C., allowed to warm to room temperature, and stirred for 2 hrs. The bi-phasic solution was gradually cooled to −78° C., and 4-(1-dodecynyl)-2-thiophenecarboxaldehyde (11.5 g) was added by means of a syringe. The mixture was stirred for 20 mins at −78° C., allowed to warm to 0° C., and stirred for an additional 2 hrs. The mixture was diluted with diethyl ether and washed with 1N aqueous sodium bisulfate solution followed by water. The organic phase was separated and concentrated in vacuo. The residue was diluted with diethyl ether (90 ml) and cooled to 0° C. To the solution was added 1:1/30% aqueous hydrogen peroxide/methanol (90 ml). The mixture was stirred at 0° C. for 1 hr, and poured into saturated sodium bicarbonate solution (100 ml). The aqueous phase was extracted with diethyl ether, the organic phases were combined, dried over anhydrous magnesium sulfate, filtered, and the filtrate was concentrated in vacuo. The residue was flash chromatographed over silica gel (eluted with ethyl acetate/heptane/1:15 followed by increasing polarity to ethyl acetate/:heptane/1:5). The appropriate fractions were collected and evaporated to afford 12.6 g (58%) of product1; $[\alpha]_D^{25}=+41.3°$ (c. 1.47, chloroform).

ANALYSIS: Calculated for $C_{29}H_{36}BrNO_4S$: 60.62%C 6.32%H 2.44%N Found: 60.78%C 6.62%H 2.58%N

EXAMPLE 172

(4S)-3-{2'R,3'S)-2'-Azido-3'-hydroxy-3'-[4-(1-dodecynyl)- 2-thienyl]propanolyl}-4-(phenylmethyl)-2-oxazolidinone To a solution of (4S)-3-{2'S,3'R)-2'-bromo-3'-hydroxy-3'- [4-(1-dodecynyl)-2-thienyl]propanoyl}-4-(phenylmethyl)- 2-oxazolidinone (20.4 g) and dimethylsulfoxide (150 ml) was added (4.61 g) sodium azide in one portion. The reaction mixture was stirred at room temperature for 5 hrs, diluted with heptane/dichloromethane/2:1 (3 l), and washed with water. The organic phase was separated, dried over anhydrous magnesium sulfate, filtered, and the filtrate was concentrated in vacuo. The residue was flash chromatographed over silica gel (eluted with ethyl acetate/heptane/ 1:2). The appropriate fractions were collected and evaporated to afford 15.4 g (81%) of product. A 1.5 g-portion was rechromatographed over silica gel (eluted with chloroform) to afford the analytical sample as a yellow oil, $[\alpha]_D^{25}=+15.4°$ (c. 1.48, chloroform).

ANALYSIS: Calculated for $C_{29}H_{36}N_4O_4S$: 64.90%C 6.76%H 10.44%N Found: 64.61%C 6.87%H 10.06%N

EXAMPLE 173

Methyl (2R,3S)-2-Azido-3-hydroxy-3-[4-(1-dodecynyl)-2-thienyl]propionate

To a solution of (4S)-3-{(2'R,3'S)-2'-azido-3'-hydroxy-3'- [4-( 1-dodecynyl)-2-thienyl]propanoyl}-4-(phenylmethyl)- 2-oxazolidinone (13.2 g) in methanol/dichloromethane/1:1 at 0° C. was added a solution of methoxymagnesium bromide, prepared by the addition of methylmagnesium bromide (3.0M, diethyl ether) (9.0 ml) to methanol (35 ml). The solution was stirred for 20 min at 0° C., and 1N sodium bisulfate solution was added. The solution was partitioned between dichloromethane (500 ml) and water (200 ml). The aqueous phase was separated and extracted with dichloromethane. The organic phases were combined, dried over anhydrous magnesium sulfate, filtered, and the filtrate was concentrated in vacuo. The residue was flash chromatographed over 400 g of silica gel (eluted with ethyl acetate/ heptane/1:6). The appropriate fractions were collected and evaporated. A 1.07 g-sample of the residue was rechromatographed over silica gel (100 g) (eluted with chloroform) to afford 0.93 g (65%) of product, as an oil.

ANALYSIS: Calculated for $C_{20}H_{29}N_3O_3S$: 61.35%C 7.47%H 10.73%N Found: 61.26%C 7.32%H 10.17%N

EXAMPLE 174

(2S,3S)-2-Amino-1-[4-(1-dodecynyl)-2-thienyl]-1,3-propanediol maleate

To a solution of methyl (2R,3S)-2-azido-3-hydroxy-3-[4- (1-dodecynyl)-2-thienyl]propionate (5.50 g) and diethyl ether (100 ml) at 0° C. was added lithium aluminum hydride (1.74 g) in small portions. The mixture was stirred at 0° C. for 1 hr, allowed to warm to room temperature and stirred for 2 hrs. The solution was cooled to 0° C., and ethyl acetate was added. The suspension was diluted with ethyl acetate (700 ml) and washed with water (200 ml). The aqueous phase was extracted with ethyl acetate, and the organic phases were combined, dried over anhydrous magnesium sulfate, filtered, and the filtrate was concentrated in vacuo. The residue was flash chromatographed over silica gel (eluted with chloroform/methanol/1:1). The appropriate fractions were collected and evaporated. The residue was crystallized from ethyl acetate/heptane/1:4 to afford 2.15 g (45%) of product free base, $[\alpha]_D^{25}=-16.3$ (c. 0.69, chloroform). The N-t-butylcarbamate was prepared from di-tert-butyldicarbonate in methylene chloride according to the procedure of Example 154 and was optically pure by chiral high pressure liquid chromatographic analysis. A second reaction yielded 1.05 g of product free base, $[\alpha]_D^{25}=-17.1°$ (c. 0.52, chloroform).

To a solution of 2.78 g of product free base in ethyl acetate (50 ml) was added maleic acid (1.16 g). The precipitate was recrystallized two times from ethyl acetate to afford 3.26 g (87%) of product, mp 121°–122° C., $[\alpha]_D^{25}=-18.0°$ (c. 0.54, ethanol)

ANALYSIS: Calculated for $C_{23}H_{35}NO_6S$: 60.90%C 7.78%H 3.09%N Found: 60.66%C 7.87%H 2.99%N

EXAMPLE 175

(4R)-3-{2'R,3'S)-2'-Bromo-3'-[4-(1-dodecynyl)-2-thienyl] propanoyl}-4-(phenylmethyl)-2-oxazolidinone To a solution of 4(R)-3(bromoacetyl)-2-oxazolidinone (22.6 g) in diethyl ether (180 ml) at −78° C. was added di-n-butylboron triflate (21 ml) followed by triethylamine (15 ml). The reaction mixture was stirred for 5 min at −78° C., allowed to warm to room temperature, and stirred for 2.5 hrs. The mixture was gradually cooled to −78° C. and 4-(1-dodecynyl)-2-thiophene carboxaldehyde (23 g) was added slowly by means of a syringe. The mixture was stirred at −78° C. for 20 min, allowed to warm to 0° C., and stirred for 2.5 hrs. The mixture was diluted with diethyl ether (700 ml), and the solution was washed 1N sodium bisulfate solution (two times with 300 ml) followed by water (300 ml). The organic phase was separated and concentrated in vacuo. The residue was dissolved in diethyl ether (100 ml) and cooled to 0° C. To the resulting solution was added 30% hydrogen peroxide/methanol/1:1 (180 ml). The solution was stirred for 1 hr and poured into saturated sodium bicarbonate solution (300 ml). The aqueous phase was extracted with ethyl acetate. The organic phases were combined, dried over anhydrous magnesium sulfate, filtered, and the filtrate was concentrated in vacuo. The residue was flash chromatographed over silica gel (eluted with ethyl acetate/heptane/ 1:12 followed by ethyl acetate/heptane/1:5). The appropriate fractions were collected and evaporated. A 1.0 g-sample of the residue was rechromatographed over silica gel (eluted with chloroform) to afford 0.93 g (47%) of product, as an oil.

ANALYSIS: Calculated for $C_{29}H_{36}O_4BrSN$: 60.62%C 6.31%H 2.43%N Found: 60.42%C 6.43%H 2.52%N

EXAMPLE 176

(4R)-3-{2'S,3'R)-2'-Azido-3'-hydroxy-3'-[4-(1-dodecynyl)-2-thienyl]propanoyl}-4-(phenylmethyl)-2-oxazolidinone To a solution of (4R)-3-{2'S,3'R)-2'-azido- 3'-hydroxy-3'-[4-(1-dodecynyl)-2-thienyl]propanoyl}-4-(phenylmethyl)-2-oxazolidinone (15.0 g) in dimethylsulfoxide (120 ml) was added sodium azide (3.4 g). The reaction mixture was stirred at room temperature for 6 hrs, diluted with a solution of heptane/dichloromethane/2:1 (3 l), and washed with water. The organic phase was separated, dried over anhydrous magnesium sulfate, filtered, and the filtrate was concentrated in vacuo. The residue was flash chromatographed over silica gel (eluted with ethyl acetate/heptane/1:2). The appropriate fractions were collected and evaporated. A 1.00 g-sample of the residue was rechromatographed over silica gel (eluted with chloroform) to afford 800 mg (71%) of product, $[\alpha]_D^{25}=17.3°$ (c. 0.48, chloroform).

ANALYSIS: Calculated for $C_{29}H_{36}N_4O_4S$: 64.90%C 6.76%H 10.44%N Found: 65.45%C 6.86%H 9.98%N

EXAMPLE 177

(2R,3R)-2-Amino-1-[4-(1-dodecynyl)-2-thienyl]-1,3-propanediol maleate

To a solution of (4R)-3-{2'S,3'R)-2'-azido-3'-hydroxy-3'-[4-( 1-dodecynyl)-2-thienyl]propanoyl}-4-(phenylmethyl)-2-oxazolidinone (11.4 g) and dichloromethane:methanol/1:1 (140 ml) at 0° C. was added a slurry of methoxymagnesium bromide, prepared by the addition of methylmagnesium bromide (3.0M, diethyl ether (7.8 ml) to methanol (35 ml). The mixture was stirred for 20 mins, at 0° C. and quenched with 1N aqueous sodium bisulfate solution (50 ml). The mixture was partitioned between dichloromethane (500 ml) and water (100 ml). The aqueous phase was extracted with dichloromethane and the organic phases were combined, dried over anhydrous magnesium sulfate, filtered, and the filtrate was concentrated in vacuo. The residue was flash chromatographed over silica gel (eluted with ethyl acetate-:heptane/1:5). The appropriate fractions were collected and evaporated to afford 5.38 g (65%) of methyl (2S,3R)-2-azido-3-hydroxy-3-[4-(1-dodecynyl)-2-thienyl]propionate.

To a solution of (2S,3R)-2-azido-3-hydroxy-3-[4-(1-dodecynyl)-2-thienyl]propionate (5.38 g) and diethyl ether (100 ml) at 0° C. was added lithium aluminum hydride (1.70 g) in small portions. The mixture was stirred for 30 mins at 0° C., allowed to warm to room temperature, and stirred for 2 hrs. The mixture was cooled to 0° C., and ethyl acetate was added. The mixture was partitioned between water (100 ml) and ethyl acetate (700 ml). The emulsion was extracted with ethyl acetate, and the organic phases were combined, dried over anhydrous magnesium sulfate, filtered, and the filtrate was concentrated in vacuo. The residue was flash chromatographed over silica gel (eluted with chloroform/methanol/ 7:1 followed by chloroform/methanol/5:1). The appropriate fractions were collected and evaporated to afford 2.25 g (49%) of product free base, $[\alpha]_D^{25}=+17.2°$ (c. 0.54, chloroform).

A small sample of the N-t-butylcarbamate derivative was prepared as in Example 154 and was optically pure by chiral high pressure liquid chromatography analysis.

To a solution of product free base (1.47 g) in ethyl acetate (50 ml) was added maleic acid (615 mg). The precipitate was recrystallized to afford 1.88 g (95%) of product, mp 121°–122° C., $[\alpha]_D^{25}=+18.9°$ (c. 0.57, ethanol).

ANALYSIS: Calculated for $C_{23}H_{35}NO_6S$: 60.90%C 7.78%H 3.09%N Found: 60.84%C 7.77%H 3.04%N

EXAMPLE 178 trans-3-[3-(1-Dodecynyl)phenyl]propen-1-ol

To a solution of ethyl trans-3-[3-(1-dodecynyl)phenyl]-2-propenoate (10.0 g) and dry tetrahydrofuran (100 ml) at −78° C. was added diisobutylaluminum hydride (1.5M in toluene) (49 ml) slowly. The reaction mixture was stirred for 20 mins at −78° C., and 25% sodium hydroxide solution (3 ml) was added. The mixture was slowly warmed to room temperature and an additional 25% sodium hydroxide solution (3 ml) was added. The mixture was diluted with ethyl acetate and washed with water and brine. The organic phase was separated, dried over anhydrous magnesium sulfate, filtered, and the filtrate was concentrated in vacuo. The residue was flash chromatographed over silica gel (eluted with ethyl acetate/hexane/1:3). The appropriate fractions were collected and evaporated to afford 7.14 g (81%) of product.

ANALYSIS: Calculated for $C_{21}H_{30}O$: 84.51%C 10.13%H Found: 84.43%C 10.23%H

EXAMPLE 179

2-(1-Dodecynyl)thiophene

To a solution of 2-iodothiophene (31.5 g), 1-dodecyne (2.5 g), triethylamine (105 ml), and tetrahydrofuran (100 ml) was added (bis)triphenylphosphine palladium(II)chloride (1.73 g) followed by copper(I)iodide (0.24 g). The reaction mixture was warmed to 55° C. and stirred for 7 hr. The solution was allowed to cool to room temperature and stirred overnight. The mixture was filtered, and the precipitate was washed with ethyl acetate. The filtrate was diluted with ethyl acetate and washed with water and brine. The organic phase was separated, dried over anhydrous magnesium sulfate, filtered, and the filtrate was concentrated in vacuo. The residue was flash chromatographed over silica gel (eluted with hexane). The appropriate fractions were collected and evaporated. The residue was distilled to afford 27.6 g (74%) of product, bp 145°–150° C. at 0.7 mm Hg.

ANALYSIS: Calculated for $C_{16}H_{24}S$: 77.36%C 9.74%H Found: 77.25%C 9.69%H

EXAMPLE 180

2-(1-Dodecynyl)fluorobenzene

To a solution of 2-bromofluorobenzene (49 g), 1-dodecyne (210 ml) triethylamine (210 ml), and tetrahydrofuran (50 ml) was added (bis)triphenylphosphine palladium(II)chloride (532 mg) and copper(I)iodide (532 mg). The reaction mixture was warmed to 55° C. and stirred for 24 hr. The mixture was allowed to cool to room temperature and filtered. The precipitate was washed with ethyl acetate, and the filtrate was diluted with ethyl acetate and washed with water and brine. The organic phase was separated, dried over anhydrous magnesium sulfate, filtered and the filtrate was concentrated in vacuo. The residue was flash chromatographed over silica gel (eluted with hexane). The appropriate fractions were collected and evaporated. The residue was distilled to afford 11 g (15%) of product, bp 175°–180° C. at 1 mm Hg.

ANALYSIS: Calculated for $C_{18}H_{25}F$: 83.03%C 9.68%H Found: 83.11%C 9.80%H

EXAMPLE 181

2-(1-Undecynyl) fluorobenzene

To a solution of 2-bromofluorobenzene (17.5 g), 1-undecyne (18.3 g), tetrahydrofuran (50 ml), and triethylamine (70 ml) was added bistriphenylphosphine palladium(II)chloride (1.2 g) and copper(I) iodide (162 mg). The reaction mixture was stirred at 55° C. for 3 hr, and an additional 2-bromofluorobenzene (2.0 g) and bistriphenylphosphine palladium(II)chloride (200 mg) were added. The mixture was stirred at 55° C. overnight, allowed to cool to room temperature, diluted with ethyl acetate and washed with water. The organic phase was dried over anhydrous magnesium sulfate, filtered, and the filtrate was concentrated in vacuo. The residue was chromatographed over silica gel (eluted with hexane). The appropriate fractions were collected and evaporated. The residue was distilled twice under vacuum to give 13.1 g (53%) of product.

ANALYSIS: Calculated for $C_{17}H_{23}F$: 82.88%C 9.41%H Found: 83.11%C 9.81%H

EXAMPLE 182

2-Fluoro-3-(1-undecynyl)benzaldehyde

To a solution of 2-(1-undecynyl)fluorobenzene (7.00 g) and tetrahydrofuran (70 ml) was added slowly n-butyllithium (1.6M, 17.8 ml) at −78° C. The reaction mixture was stirred at −78° C. for 1.5 hrs. Dimethylformamide (2.28 ml) was added slowly, and the solution was allowed to warm to room temperature over 1 hr, with stirring. Methylene chloride (300 ml) was added, and the solution was washed with 50% hydrochloric acid. The aqueous phase was extracted with methylene chloride. The extracts were combined, dried over anhydrous magnesium sulfate, filtered, and the filtrate was evaporated. The residue was chromatographed on silica (250 g), eluting with hexane followed by ethyl acetate/hexane (1:4). The appropriate fractions were collected and evaporated to provide 3.53 g (45.2%) of product as an oil.

EXAMPLE 183 erythro-2-Amino-1-[6-(7-phenyl-1-heptynyl)-2-pyridinyl]-1,3-propanediol maleate

A solution of erythro-N-{1,3-dihydroxy-1-[6-(7-phenyl-1-heptynyl)-2-pyridinyl]-2-propanyl}acetamide (4.3 g), 2N sodium hydroxide (40 ml), and ethanol (25 ml) were heated at 60° C., under nitrogen, for 23 hrs. The reaction mixture was cooled and extracted with chloroform. The extract was washed with sodium chloride solution, dried over anhydrous magnesium sulfate, filtered, and the filtrate was evaporated. The residue was chromatographed three times on silica gel eluting with chloroform:methanol:2N ammonium hydroxide/950:50:3. The appropriate fractions were combined, evaporated and the residue was dried each time to give 1.7 g (46% yield) of product free base. Maleic acid (0.6 g) in ethyl acetate was added to the product free base. The precipitate was collected and recrystallized from ethyl acetate to give which gave 1.10 g (22% yield) of product, mp 142°–143° C.

Analysis: Calculated for $C_{25}H_{30}N_2O_6$: 66.06%C 6.65%H 6.16%N Found: 66.07%C 6.76%H 6.12%N

EXAMPLE 184 erythro-N-{1,3-Diacetyloxy-1-[6-(7-phenyl-1-heptynyl)-2-pyridinyl]-2-propanyl}acetamide A mixture of N-{1,3-dihydroxy-1-[6-(7-phenyl-1-heptynyl)-2-pyridinyl]-2-propanyl}acetamide (9.4 g), acetic anhydride (14.5 ml), triethylamine (32 ml), and 4-dimethylaminopyridine (0.31 g), and tetrahydrofuran (140 ml) was stirred at room temperature overnight. The reaction mixture was evaporated, methanol was added to the residue, and the solution was warmed at 50° C. for 20 min. The mixture was evaporated and azeotroped with toluene. A solution of 7.5% sodium bicarbonate was added to the residue until pH 8.5, and the mixture was extracted with chloroform. The extract was dried over anhydrous magnesium sulfate, filtered, and the filtrate was evaporated. The residue was chromatographed on silica gel eluting with chloroform:2-propanol (0.5% to 1%). The appropriate fractions were collected and evaporated to give 9.8 g (85% yield) of product. Portions were rechromatographed twice, eluting with hexane:chloroform:2-propanol to give the analytical sample, as an oil.

Analysis: Calculated for $C_{27}H_{32}N_2O_5$: 69.81%C 6.94%N 6.03%N Found: 69.56%C 7.05%H 5.93%N

EXAMPLE 185 erythro-2-Amino-1-[6-(1-decynyl)-2-pyridinyl]-1,3-propanediol maleate

A solution of erythro-N-{1-[6-(1-decynyl)-2-pyridinyl]-1,3-dihydroxy-2-propanyl}acetamide (3.0 g), 2N sodium hydroxide (45 ml), and ethanol (45 ml) was heated at 100° C., under nitrogen, for 4 hrs. The reaction mixture was cooled, water was added, and the mixture was extracted with chloroform:2-propanol/3:1. The combined extracts were washed with sodium chloride solution, dried over anhydrous magnesium sulfate, filtered, and the filtrate was evaporated. The residue was chromatographed twice on silica gel, eluting with chloroform:methanol:2N ammonium hydroxide solution/960:40:3. The appropriate fractions were collected and evaporated each time to give 0.93 g (35%) of product free base, as an oil. A 0.76 g-portion of product free base was treated with maleic acid (0.29 g) in ethyl acetate to give 0.50 g of the analytical sample of product, mp 126°–128° C.

Analysis: Calculated for $C_{22}H_{32}N_2O_6$: 62.84%C 7.67%H 6.66%N Found: 62.58%C 7.72%H 6.84%N

EXAMPLE 186 erythro-2-Amino-1-[4-(1-dodecynyl)-2-thiazolyl]-1,3-propanediol hydrochloride

A solution of erythro-N-{1-[4-(1-dodecynyl)-2-thiazolyl]-1,3-dihydroxy-2-propanyl}acetamide (5.8 g), 2N sodium hydroxide solution (39 ml) and ethanol (25 ml) was heated at 60° C., under nitrogen, for 23 hrs. The reaction mixture was cooled, water was added, and the mixture was extracted with chloroform. The extracts were washed with brine solution, dried over anhydrous magnesium sulfate, filtered, and the filtrate was evaporated. The residue was chromatographed on silica gel eluting with chloroform:methanol:2N ammonium hydroxide solution/950:50:3. The appropriate fractions were collected and concentrated. A 2.4 g-portion of the residue (4.3 g) was dissolved in ethyl acetate, concentrated hydrochloric acid (0.6 ml) was added, and the mixture was evaporated. The residue was redissolved and evaporated with ethyl acetate and then 2-propanol. The residue was dried under vacuum to give 2.4 g (76.0%) of product, mp 194°–197° C.

Analysis: Calculated for $C_{18}H_{30}N_2O_2S\cdot HCl$: 57.66%C 8.33%H 7.47%N Found: 57.35%C 8.48%H 7.25%N

EXAMPLE 187

Ethyl erythro-2-acetamido-3-[4-(1-dodecynyl)-2-thiazolyl]-3-hydroxypropionate

A solution of 4-(1-dodecynyl)-2-thiazolecarboxaldehyde (18.3 g), acetamidomalonic acid monoethyl ester (14.1 g), and triethylamine (8.3 g) in dry tetrahydrofuran (70 ml) was stirred, under nitrogen, for 4 hrs. The precipitate was collected, the filter cake washed with heptane, and recrystallized from ethyl acetate to give 16.0 g (57.0%) of product, mp 131°–132.5° C.

Analysis: Calculated for $C_{22}H_{34}N_2O_4S$: 62.53%C 8.11%H 6.63%N Found: 62.36%C 8.28%H 6.58%N

EXAMPLE 188 erythro-N-{1-[4-(1-Dodecynyl)-2-thiazolyl]-1,3-dihydroxy-2-propanyl}acetamide

To a solution of ethyl erythro-2-acetamido-3-[4-(1-dodecynyl)-2-thiazolyl]-3-hydroxypropionate (13.8 g) in dry tetrahydrofuran (275 ml) was added slowly 2M lithium borohydride/tetrahydrofuran (14 ml) at 5° C., under nitrogen, and the mixture was stirred at room temperature over the weekend. The reaction mixture was chilled, and methanol:water/ 1:1 was added slowly, followed by glacial acetic acid (1.8 ml) in methanol:water/1:1 (25 ml). The solution was stirred at room temperature for 1 hr, evaporated, and then azeotroped with methanol. Ethyl acetate was added to the residue, saturated sodium bicarbonate solution was added until pH 8, and the mixture was extracted with ethyl acetate. The extract was washed with brine, dried over anhydrous magnesium sulfate, filtered, and the filtrate was concentrated. The residue was flash chromatographed on silica gel eluting with ethyl acetate to ethyl acetate:0.5% methanol. The appropriate fractions were collected and evaporated. An 8.0 g-portion of the residue (11.1 g) was recrystallized from ethyl acetate to give 6.90 g (77.0% yield) of product, mp 93°–95° C.

Analysis: Calculated for $C_{20}H_{32}N_2O_3S$: 63.12%C 8.48%H 7.36%N Found: 63.26%C 8.82%H 7.30%N

EXAMPLE 189 erythro-2-Amino-1-[4-(1-dodecynyl)-2-thiazolyl]-1,3-propanediol erythro-N-{1-[4-(1-dodecynyl)-2-thiazolyl]-1,3-dihydroxy-2-propanyl}acetamide (5.8 g), 39 ml 2N sodium hydroxide and ethanol was heated at 60° C., under nitrogen, for 23 hrs. The reaction mixture was cooled, water was added, and the mixture was extracted with chloroform. The extract was washed with brine, dried over anhydrous magnesium sulfate, filtered, and the filtrate was evaporated. The residue was chromatographed on silica gel eluting with chloroform. The appropriate fractions were collected and evaporated. A 1.9 g-portion of the residue (4.3 g) was recrystallized from ethyl acetate to give 1.6 g (71.0% yield) of product, mp 110°–112° C.

Analysis: Calculated for $C_{18}H_{30}N_2O_2S$: 63.87%C 8.93%H 8.28%N Found: 64.02%C 8.95%H 8.23%N

EXAMPLE 190

(2S,3S)-2-Amino-1-[4-(1-dodecynyl)-2-thienyl]-1,3-propanediol hydrochloride

A solution of (2S,3S)-2-amino-1-[4-(1-dodecynyl)-2-thienyl]-1,3-propanediol maleate (2.8 g) and ethyl acetate was washed two times with 10% aqueous sodium hydroxide solution and then with water. The organic phase was separated, dried over anhydrous magnesium sulfate, filtered, and the filtrate was concentrated in vacuo. The residue was dissolved in ethyl acetate (30 ml) and concentrated hydrochloric acid (0.55 ml) was added. The solution was concentrated in vacuo, and the residue was recrystallized from 2-propanol to give 1.47 g (64%) of product, $[\alpha]_D^{25}=-22°$ (c. 0.58, ethanol), mp 78° (decomp).

Analysis: Calculated for $C_{19}H_{32}ClNO_2S$: 61.02%C 8.62%H 3.75%N Found: 61.29%C 8.74%H 3.71%N

EXAMPLE 191

(2R,3R)-2-Amino-1-[4-(1-dodecynyl)-2-thienyl]-1,3-propanediol hydrochloride

A solution of (2R,3R)-2-amino-1-[4-(1-dodecynyl)-2-thienyl]-1,3-propanediol maleate (1.3 g) and ethyl acetate was washed two times with 10% aqueous sodium hydroxide solution and then with water. The organic phase was separated, dried over magnesium sulfate, filtered, and the filtrate was concentrated in vacuo. The residue was dissolved in ethyl acetate (30 ml), and concentrated hydrochloric acid (0.25 ml) was added. The solution was concentrated in vacuo, and the residue was recrystallized from 2-propanol to give 840 mg (78%) of product, $[\alpha]_D^{25}=+27.2°$ (c. 051, ethanol), mp 78° (decomp).

Analysis: Calculated for $C_{19}H_{32}ClNO_2S$: 61.02%C 8.62%H 3.75%N Found: 60.83%C 8.90%H 3.70%N

EXAMPLE 192 erythro-2-Amino-1-[2-(1-dodecynyl)-4-thienyl]-1,3-propanediol hydrochloride

A solution of erythro-N-{1-[2-(1-dodecynyl)-4-thienyl]-1,3-dihydroxy-2-propanyl}acetamide (7.1 g), 2N sodium hydroxide solution (46.5 ml) and ethanol (23 ml) was heated at 60° C., under nitrogen, for 20 hrs. The reaction mixture was cooled, water was added, and the mixture was extracted with chloroform. The extracts were washed with brine, dried over anhydrous magnesium sulfate, filtered, and the filtrate was evaporated. The residue was chromatographed on silica gel, eluting with chloroform:methanol:2N ammonium hydroxide solution/950:50:3 to 925:75:4. The appropriate fractions were collected and evaporated. A 3.5 g-portion of the residue (4.84 g) was dissolved in 2-propanol, cooled, and concentrated hydrochloric acid (0.9 ml) was added. The mixture was evaporated, 2-propanol was added several times and evaporated, and the residue was dried under high vacuum to yield 3.7 g (73% yield) of product.

Analysis: Calculated for $C_{19}H_{32}ClNO_2S$: 61.02%C 8.62%H 3.75%N Found: 60.64%C 8.77%H 3.51%N

EXAMPLE 193 erythro-[2-(2-Amino-1,3-dihydroxy-1-propyl)-4-thienyl]-1-dodecanone

A solution of erythro-2-amino-1-[4-(1-dodecynyl)-2-thienyl]-1,3-propanediol (2.00 g), dissolved in tetrahydrofuran (10 ml) was stirred at room temperature as 3M sulfuric acid (5 ml), followed by mercury (II) oxide (642 mg) was added. The reaction mixture was stirred overnight. The reaction was repeated on the same scale, and the two reaction mixtures were combined. The combined reaction mixture was basified with sodium bicarbonate solution, chloroform was added, and the biphasic mixture was filtered through a bed of celite. The filtercake was washed with warm chloroform, and the combined organic phases were dried over anhydrous sodium sulfate, filtered, and the filtrate was evaporated. The residue was flash chromatographed (silica; 90:9:1 dichloromethane:methanol:ammonium hydroxide). The appropriate fractions were collected and evaporated. The residue was crystallized from ethyl acetate-petroleum ether to give 2.1 g (50%) of product, mp 96°–99° C.

Analysis: Calculated for $C_{19}H_{33}NO_3S$: 64.19%C 9.36%H 3.94%N Found: 64.21%C 9.47%H 3.84%N

EXAMPLE 194

N-[1-[4-(1-dodecynyl)-2-thienyl]-3-hydroxy-2-propyl]acetamide

To a solution of diethyl (acetamido)[[4-(1-dodecynyl)-2-thienyl]methyl]propanedioate (12.3 g) in dry tetrahydrofuran (100 ml) was added 2M lithium borohydride/tetrahydrofuran (12.8 ml), and the mixture was stirred at 60° C. for 4 hrs. The solution was cooled, quenched with a 50:50:10 solution of methanol:water:acetic acid, and extracted with ethyl acetate. The organic extracts were evaporated, and the residue was chromatographed on silica gel (9:1 ethyl acetate:dichloromethane). The appropriate fractions were collected and evaporated. The residue was crystallized from ether:heptane to give 5.3 g (57%) of product, mp 55°–58° C.

Analysis: Calculated for $C_{21}H_{33}NO_2S$: 69.38%C 9.15%H 3.85%N Found: 68.94%C 8.95%N 3.61%N

EXAMPLE 195

2-Amino-3-[4-(1-dodecynyl)-2-thienyl]-1-propanol

To a solution of N-[1-[4-(1-dodecynyl)-2-thienyl]-3-hydroxy-2-propyl]acetamide (4.6 g) in 95% ethanol (30 ml) was added degassed 2N sodium hydroxide solution. The reaction mixture was stirred at 65° C. overnight. The solution was diluted with saturated ammonium chloride solution and extracted with ethyl acetate. The organic extracts were evaporated, and the residue was flashed chromatographed on silica gel (9:1 dichloromethane:methanol). The appropriate fractions were collected and evaporated. The residue was taken up in ether, an ethereal hydrogen chloride was added, and the mixture was stirred at room temperature for 30 mins. The precipitate was collected and air-dried to give 2.05 g (45.4%) of product, mp 85°–135° C.

Analysis: Calculated for $C_{19}H_{32}ClNOS$: 63.75%C 9.01%H 3.91%N Found: 63.66%C 9.21%H 3.76%N

EXAMPLE 196

Diethyl(acetamido)[4-(1-(dodecynyl)-2-thienyl]methyl]propandioate.

To a solution of 4-(1-dodecynyl)-2-thiophene methanol (32 g), triethylamine (13.3 g), and dry dichloromethane (250 ml) was added methanesulfonyl chloride (10.7 g) over 5 mins, and the mixture was stirred at room temperatures for 3 hrs. The solution was evaporated, the residue was taken up in absolute ethanol (100 ml) and was added dropwise to a solution of diethyl acetamido malonate (29.0 g) and 21 wt % sodium ethoxide (51.5 ml) in absolute ethanol (200 ml). The solution was stirred, under nitrogen, at 90° C. for 1 hr and then evaporated. The residue was taken up in ethyl acetate. The mixture was washed with water and dilute hydrochloric acid, dried over magnesium sulfate, filtered, and the filtrate was evaporated. The residue was chromatographed (50:1 dichloromethane/ethyl acetate). The appropriate fractions were collected and evaporated to give 27.1 g (49.1%) of product, as an oil.

Analysis: Calculated for $C_{26}H_{39}NO_5S$: 65.38%C 8.23%H 2.39%N Found: 64.94%C 7.88%H 3.23%N

EXAMPLE 197

Ethyl erythro-2-acetamido-3-[5-(1-decynyl)-2-benzo[b]thienyl]-3-hydroxypropionate A solution of 5-(1-decynyl)-2-benzo[b]thiophenecarboxaldehyde (36.8 g) acetamidomalonic acid monoethyl ester (24.5 g), triethylamine (13.1 g), and dry tetrahydrofuran (150 m) was degassed and stirred at room temperature, under nitrogen, for five days. Acetamidomalonic acid monoethyl ester (11.7 g) was added, and the solution was degassed and stirred at room temperature, under nitrogen, for 2 days. The reaction mixture was evaporated. The residue was flash chromatographed (silica; 1:1 ethyl acetate::heptane). The appropriate fractions were collected and evaporated and the residue was crystallized from ether-petroleum ether. Recrystallization of the residue from ethyl acetate:heptane gave 36.7 g (67%) of product, mp 95°–97° C.

Analysis: Calculated for $C_{25}H_{33}NO_4S$: 67.69%C 7.50%H 3.16%N Found: 67.30%C 7.45%H 3.00%N

EXAMPLE 198 erythro-N-[1-[5-(1-decynyl)-2-benzo[b]thienyl]-1,3-dihydroxy-2-propyl]acetamide

A solution of ethyl erythro-2-acetamido-3-[5-(1-decynyl)-2-benzo[b]thienyl]-3-hydroxypropionate (11.4 g) in dry tetrahydrofuran (100 ml) was stirred at 0° C., under nitrogen, as lithium borohydride (2.0M in tetrahydrofuran) (16.7 ml) was added dropwise. The reaction mixture was stirred under a nitrogen atmosphere for three hrs, cooled to 0° C., and quenched by the dropwise addition of a 20:20:3 methanol:water:acetic acid solution. The solution was diluted with ammonium chloride solution (300 ml) and extracted with ethyl acetate. The combined organic extracts were dried over anhydrous sodium sulfate, filtered, and the filtrate was evaporated. The residue was flash chromatographed (silica, 7% methanol:dichloromethane). The appropriate fractions were collected and evaporated. The residue was recrystallized from ethyl acetate:heptane to give 7.3 g (71%) of product, mp 130°–132° C.

Analysis: Calculated for $C_{23}H_{35}NO_3S$: 68.11%C 8.70%H 3.45%N Found: 67.89%C 8.82%H 3.47%N

EXAMPLE 199 erythro-2-Amino-1-[5-(1-decynyl)-2-benzo[b]thienyl-1,3-propanediol

A solution of erythro-N-[1-[5-(1-decynyl)-2-benzo[b]thienyl]-1,3-dihydroxy-2-propyl]acetamide (10.5 g), 2N sodium hydroxide solution (100 ml) and 95% ethanol (75 ml) was stirred at 50° C. overnight. The reaction mixture was cooled to room temperature, diluted with ammonium chloride solution (300 ml) and extracted with ethyl acetate. The combined organic extracts were dried over anhydrous sodium sulfate, filtered, and the filtrate was evaporated. The residue was flash chromatographed (silica; 90:9:1 dichloromethane:methanol:ammonium hydroxide). The appropriate fractions were collected and evaporated. The residue was recrystallized from ethyl acetate to give 5.7 g of product, mp 146°–149° C.

Analysis: Calculated for $C_{21}H_{29}NO_2S$: 70.16%C 8.13%H 3.90%N Found: 69.88%C 8.35%H 3.75%N

EXAMPLE 200 erythro-N-[1-[5-(1-decyl)-2-benzo[b]thienyl]-1,3-dihydroxy-2-propyl]acetamide

A mixture of erythro-N-[1-[5-(1-decynyl)-2-benzo[b]thienyl]-1,3-dihydroxypropyl]acetamide (6.00 g) and 5% palladium-on-carbon (600 mg) in absolute ethanol (200 ml) was shaken under 50 psi of hydrogen overnight. The catalyst was filtered and washed with ethanol. The filtrate was evaporated, and the residue was recrystallized from ethyl acetate to give 5.0 g (83%) of product, mp 115°–117° C.

Analysis: Calculated for $C_{23}H_{35}NO_3S$: 68.11%C 8.70%H 3.45%N Found: 67.89%C 8.82%H 3.47%N

EXAMPLE 201 erythro-2-Amino-1-[5-(1-decyl)-2-benzo[b]thienyl]-1,3-propanediol

A solution of erythro-N-[1-[5-(1-decyl)-2-benzo[b]thienyl]-1,3-dihydroxy-2-propyl]acetamide (3.90 g), 2N sodium hydroxide solution (100 ml), and 95% ethanol (75 ml) was stirred at 50° C. overnight. The reaction mixture was cooled to room temperature, diluted with ammonium chloride solution (300 ml) and extracted with ethyl acetate. The combined organic extracts were dried over anhydrous sodium sulfate, filtered, and the filtrate was evaporated. The residue was flash chromatographed (silica, 90:9:1/dichloromethane:methanol:ammonium hydroxide). The appropriate fractions were collected and evaporated. The residue was recrystallized from ethyl acetate and then ethanol to give 2.3 g of product, mp 138°–139° C.

Analysis: Calculated for $C_{21}H_{33}NO_2S$: 69.38%C 9.155H 3.85%N Found: 69.36%C 9.36%H 3.83%N

EXAMPLE 202

Ethyl erythro-2-acetamido-3-[6-(1-decynyl)-2-quinolinyl]-3-hydroxypropionate

A solution of 6-(1-decynyl)-2-quinolinecarboxaldehyde (21.4), acetamidomalonic acid monoethyl ester (13.8 g), and triethylamine (8.1 g) in dry tetrahydrofuran (140 ml) was stirred overnight, under nitrogen, for 3 days. The reaction mixture was evaporated, ethyl acetate was added, and the solution was washed with saturated sodium bicarbonate and sodium chloride solutions. The organic layer was dried over anhydrous magnesium sulfate, filtered, and the filtrate was concentrated. The residue was chromatographed on silica gel, eluting with heptane:ethyl acetate/4:1 to 1:2. The appropriate fractions were collected and evaporated. A 11.45 g-portion of the residue (22.7 g) was recrystallized from hexane:ethyl acetate/9:1 to give 9.9 g (61.5%) of product, mp 86°–88° C.

Analysis: Calculated for $C_{26}H_{34}N_2O_4$: 71.21%C 7.81%H 6.39%N Found: 71.17%C 7.93%H 6.43%N

EXAMPLE 203 erythro-2-Amino-1-[6-(1-decynyl)-2-quinolinyl]-1,3-propanediol maleate

A solution of erythro-N-{1-[6-(1-decynyl-2-quinolinyl]-1,3-dihydroxy-2-propanyl}acetamide (4.9 g), 2N sodium hydroxide solution (31 ml), and ethanol (30 ml) was heated at 60° C., under nitrogen, for 24 hrs. The reaction mixture was cooled, water was added, and the mixture was extracted with chloroform. The extract was washed with brine, dried over anhydrous magnesium sulfate, filtered, and the filtrate was evaporated. The residue was chromatographed twice on silica gel eluting with chloroform:methanol:2N ammonium hydroxide/950:50:3 to 925:75:4. The appropriate fractions were collected and evaporated each time. The residue was dissolved in ethyl acetate, maleic acid (0.20 g) was added, and the solution was chilled. The precipitate was collected to yield 0.65 g (11%) of product, mp 119°–120° C.

Analysis: Calculated for $C_{26}H_{34}N_2O_6$: 66.36%C 7.28%H 5.95%N Found: 66.37%C 7.42%H 5.92%N

EXAMPLE 204 erythro-N-{1-[6-(1-Decynyl)-2-quinolinyl]-1,3-dihydroxy-2-propanyl}acetamide

To a solution of erythro-2-acetamido-3-[6-(1-decynyl)-2-quinolinyl]-3-hydroxypropionate (12.9 g) in dry tetrahydrofuran (125 ml) was added slowly 2M lithium borohydride tetrahydrofuran (12.5 ml) at 5° C., under nitrogen, at room temperature, with stirring overnight. The reaction mixture was stirred overnight, chilled, and methanol:water/1:1 (25 ml) was added slowly, followed by glacial acetic acid (1.6 ml) in methanol:water/1:1 (25 ml). The solution was stirred at room temperature for 1 hr, evaporated, and the residue was azeotroped with methanol. Saturated sodium bicarbonate solution was added to the residue until pH 8, and the mixture was extracted with ethyl acetate. The extract was washed with brine, dried over anhydrous magnesium sulfate, filtered, and the filtrate was concentrated. The residue was flash chromatographed on silica gel, eluting with ethyl acetate:methanol (1–5%). The appropriate fractions were collected and evaporated.

A 4.4 g-portion of the residue (8.5 g) was recrystallized from ethyl acetate to give 2.45 g (40.5%) of product, mp 145°–147° C.

Analysis: Calculated for $C_{24}H_{32}N_2O_3$: 72.70%C 8.13%H 7.06%N Found: 72.30%C 8.13%H 7.12%N

EXAMPLE 205

Ethyl erythro-2-acetamido-3-hydroxy-[1-(4-methylphenylsulfonyl)-5-(1-decynyl)-3-(1H)-indolyl]propionate To a solution containing 1-(4-methylphenylsulfonyl)-5-(1-decynyl)-1H-indole-3-carboxaldehyde (11.6 g) and acetamidomalonic acid monoethyl ester (4.8 g) in dry tetrahydrofuran (150 ml) was added 1.5 equivalents of triethylamine (3.7 ml). The mixture was stirred at room temperature overnight. Additional 0.5 equivalents of acetamidomalonic acid monoethyl ester (total 19.5 g) were added every morning for 8 additional days. The reaction mixture was evaporated and the residue flash chromatographed on silica gel (9:1 dichloromethane:ethyl acetate). The appropriate fractions were collected and evaporated. The residue was crystallized from ether to give 9.3 g (62.0%) of product, mp 56°–58° C.

Analysis: Calculated for $C_{26}H_{29}NO_3S$: 66.18%C 6.94%H 4.80%N Found: 61.18%C 7.14%H 4.74%N

EXAMPLE 206 erythro-N-[1-[5-(1-Decynyl)-1-(4-methylphenylsulfonyl)-3-(1H)-indolyl]- 1,3-dihydroxy-2-proponylacetamide To a solution of ethyl erythro-2-acetamido-3-hydroxy-[1-(4-methylphenylsulfonyl)-5-(1-decynyl)-3-(1H)-indolyl]propionate (21.2 g) in dry tetrahydrofuran (150 ml) was added 2M lithium borohydride (23.1 ml) over 10 mins, and the mixture was then stirred at room temperature for 3 hrs. The reaction mixture was quenched with methanol:water:acetic acid 5:5:1 and extracted with ethyl acetate. The residue was flash chromatographed on silica gel (ethyl acetate to 20:1 ethyl acetate:methanol). The appropriate fractions were collected and evaporated. The residue was recrystallized from ethyl acetate:heptane to give 8.7 g (45.3%) of product, mp 116°–118° C.

Analysis: Calculated for $C_{31}H_{40}N_2O_5S$: 66.89%C 7.11%H 5.20%N Found: 66.47%C 7.22%H 5.14%N

EXAMPLE 207 erythro-N-{1-[3-(1-Dodecynyl)-2-fluorophenyl]-1,3-dihydroxy-2-propanyl}acetamide A solution of erythro-N-{1,3-diacetyloxy-1-[3-(1-dodecynyl)-2-fluorophenyl]-2-propanyl}acetamide (14.7 g), 25% sodium hydroxide solution (50 ml), and ethanol (125 ml) was heated at 70° C., under nitrogen, for 3 hrs. The reaction mixture was cooled, water was added, and the mixture was extracted with ethyl acetate. The extract was washed with sodium chloride solution, dried over anhydrous magnesium sulfate, filtered, and the filtrate was evaporated. The residue was chromatographed on silica gel eluting with chloroform:methanol: 2N ammonium hydroxide solution 950:50:3. The appropriate fractions were collected and evaporated to give 7.8 g (64%) of product. Recrystallization from heptane:ethyl acetate/1:1 gave the analytical sample, mp 77°–79° C.

Analysis: Calculated for $C_{23}H_{34}FNO_3$: 70.56%C 8.75%H 3.58%N Found: 70.92%C 8.90%H 3.53%N

EXAMPLE 208 erythro-[3-(2-Amino-1,3-dihydroxy-1-propyl)phenyl]-1-dodecanone hydrochloride

To a solution of erythro-2-amino-1-[3-(1-dodecynyl)phenyl]-1,3-propanediol in tetrahydrofuran (150 ml) was added mercury (II) oxide (1.9 g) in a single portion, followed by 3N sulfuric acid (100 ml). The mixture was stirred at room temperature for 4 days, diluted with ethyl acetate and washed with 10% aqueous sodium hydroxide. The aqueous phase was extracted with chloroform and the organic phases were combined, dried over anhydrous magnesium sulfate, filtered, and the filtrate was concentrated in vacuo. The residue was diluted with ethyl acetate (100 ml) and concentrated hydrochloric acid (0.5 ml) was added, with stirring. The precipitate was filtered and recrystallized from ethyl acetate:methanol/10:1 to give 1.65 g (22%) of product, mp 120° C. (decomp.).

Analysis: Calculated for $C_{21}H_{36}ClNO_3$: 65.35%C 9.40%H 3.63%N Found: 65.35%C 9.54%H 3.55%N

EXAMPLE 209

Ethyl erythro-2-acetamido-3-hydroxy-3-(3-acetoxyphenyl)propionate

To a solution of 3-acetoxybenzaldehyde (40.5 g) in tetrahydrofuran (200 ml) at room temperature was added acetamido malonic acid monoethylester (49.2 g), followed by triethylamine (36 ml). The mixture was stirred at 48 hrs at room temperature, at the end of which time, an additional 0.5 equivalents of both acetamido malonic acid monoethylester and triethylamine were added. The reaction mixture was stirred for an additional 48 hrs and another 0.5 equivalents of acetamido malonic acid monoethylester and triethylamine were added. The reaction mixture was stirred for an additional 72 hrs, concentrated to ⅓ of its original volume, diluted with ethyl acetate and washed with saturated aqueous sodium bicarbonate, and then with water. The organic phase was separated, dried over anhydrous magnesium sulfate, filtered, and the filtrate concentrated in vacuo. The appropriate fractions were collected and evaporated. The residue was flash chromatographed over silica gel (eluted with ethyl acetate:heptane/2:1). The appropriate fractions were collected and concentrated. The residue was recrystallized from ethyl acetate:heptane/5:1 to give 32.6 g (43%) of product, mp 119°–120° C.

Analysis: Calculated for $C_{15}H_{19}O_6N$: 58.25%C 6.19%H 4.53%N Found: 58.15%C 6.11%H 4.36%N

EXAMPLE 210 erythro-N-[1,3-Dihydroxy-1-(3-undecyloxyphenyl)-2-propanyl]acetamide

To a solution of ethyl erythro-2-acetamido-3-hydroxy-3-(3-acetoxyphenyl)propionate (15 g) in tetrahydrofuran (200 ml) at 0° C. was added lithium borohydride (2.0M, tetrahydrofuran) (48.4 ml). The solution was allowed to warm to room temperature and stirred for 48 hrs. The reaction mixture was quenched with methanol (50 ml), diluted with water (500 ml) and extracted with two 500 ml-portions of ethyl acetate. The aqueous phase was concentrated in vacuo. The residue was diluted with water (50 ml) and acetone (300 ml), and the precipitate was collected. The filtrate was concentrated in vacuo, and the residue was flash chromatographed over silica gel (eluted with chloroform:methanol/ 4:1). The appropriate fractions were collected and evaporated to give 5.24 g (48%) of erythro-N-[1,3-dihydroxy-1-(3-hydroxyphenyl)-α-propanyl]acetamide as white solid.

To a solution of erythro-N-[1,3-dihydroxy-1-(3-hydroxyphenyl)-α-propanyl]acetamide (4.33 g) in dimethylformamide (40 ml) was added cesium carbonate (6.8 g) followed by bromoundecane (4.54 g). The mixture was stirred at room temperature for 48 hrs. The mixture was partitioned between dichloromethane (500 ml) and water (200 ml). The aqueous phase was extracted with dichloromethane, and the organic phases were combined, dried over anhydrous magnesium sulfate, filtered, and the filtrate was concentrated in vacuo. The residue was recrystallized from ethyl acetate to give 5.0 g (69%) of the product.

Analysis: Calculated for $C_{22}H_{37}NO_4$: 69.62%C 9.83%H 3.69%N Found: 69.18%C 9.96%H 3.64%N

EXAMPLE 211 erythro-2-Amino-1-[3-(1-undecyloxy)phenyl]-1,3-propanediol hydrochloride

To a solution of erythro-N-[1,3-dihydroxy-1-(3-undecyloxyphenyl)-2-propanyl]acetamide in ethanol (50 ml) was added potassium hydroxide (1.68 g) in one portion. The mixture was warmed to 70° C. and stirred overnight. The reaction mixture was allowed to cool to room temperature, concentrated in vacuo, and the concentrate was diluted with ethyl acetate and washed with water. The aqueous phase was extracted with ethyl acetate, and the organic phases were combined, dried over magnesium sulfate, filtered, and the filtrate was concentrated in vacuo. The residue was dissolved in ethyl acetate (100 ml) and concentrated hydrochloric acid (1 ml) was added dropwise, with stirring. The precipitate was collected and recrystallized from ethyl acetate to give 1.57 g of product, mp 92°–93° C. (decomp).

Analysis: Calculated for $C_{20}H_{36}ClNO_3$: 64.24%C 9.70%H 3.75%N Found: 64.23%C 9.74%H 3.67%N

EXAMPLE 212

4-(1-Dodecynyl)-2-thiazolecarboxaldehyde

A solution of 4-bromo-2-thiazolecarboxaldehyde (14.8 g), 1-dodecyne (14.1 g), and triethylamine (23.5 g) in dry tetrahydrofuran (85 m) was chilled to 5° C. and degassed under nitrogen. bis(Triphenylphosphine)palladium (II) chloride (0.54 g) and copper (I) iodide (0.07 g) were added to the mixture, which was degassed, and stirred, under nitrogen, at room temperature for 2.5 hrs. The reaction mixture was heated at 40° C. for 7 hrs, during which time additional amounts of 1-dodecyne (3.9 g), bis(triphenylphosphine)palladium (II) chloride (0.11 g), and copper (I) iodide (0.02 g) were added. The mixture was cooled to room temperature, the precipitate was collected, and the filter cake was washed with ethyl acetate. The filtrate was diluted with ethyl acetate (300 ml). Water was added in portions, and the organic layer was washed with brine, dried over magnesium sulfate, filtered, and the filtrate was concentrated. The residue was chromatographed on silica gel, eluting with heptane to heptane: 1% ethyl acetate. A portion (1.05 g) of the residue was rechromatographed, eluting with hexane:(0.3 to 1%) ethyl acetate. The appropriate fractions were collected and evaporated to yield 0.79 g (76.5% yield) of product, mp 25.5°14 26° C.

Analysis: Calculated for $C_{16}H_{23}NOS$: 69.27%C 8.36%H 5.05%N Found: 69.51%C 8.65%H 4.94%N

EXAMPLE 213

5-(1-decynyl)-2-benzo[b]thiophenecarboxaldehyde

To a solution of 5-(1-decynyl)benzo[b]thiophene (20.0 g) in dry ether (150 ml), under nitrogen, was added n-butyllithium (2.5M in hexanes) (32.6 ml) dropwise, with stirring at room temperature. The solution was stirred at room temperature, under nitrogen, for 2.5 hrs and then cooled to −60° C. A solution of dry dimethylformamide (5.95 g) in dry ether (15 ml) was added dropwise, and the reaction mixture was allow to warm to room temperature. The reaction mixture was quenched with ammonium chloride solution and the layers separated. The aqueous phase was extracted with ether, the organic extracts combined, dried over anhydrous sodium sulfate, filtered, and the filtrate was evaporated. The residue was flash chromatographed (silica: 3–4%, ethyl acetate:heptane). The appropriate fractions were collected and evaporated. The residue was recrystallized from heptane to give 11.5 g (52.0%) of product, mp 45°–47° C.

Analysis: Calculated for $C_{19}H_{22}OS$: 76.47%C 7.43%H Found: 76.63%C 7.36%H

EXAMPLE 214

6-(1-Decynyl)-2-quinolinecarboxaldehyde

A solution of 6-bromo-2-quinolinecarboxaldehyde (18.9 g), 1-decyne (12.2 g) and triethylamine (24.3 g) in dry tetrahydrofuran (300 ml) was chilled to 5° C. and degassed, under nitrogen. bis(Triphenylphosphine)palladium (II) chloride (0.56 g) and copper (I) iodide (0.08 g) were added to the reaction mixture, which was degassed and stirred under nitrogen at room temperature for 30 mins, and then heated at 40° C. for 19 hrs. The mixture was cooled to room temperature, the precipitate was filtered, and the filter cake was washed with ethyl acetate, and the filtrate was evaporated. The residue was dissolved in ethyl acetate, washed with water and brine, dried over anhydrous magnesium sulfate, filtered, and the filtrate was concentrated. The residue was chromatographed on silica gel, eluting with heptane to heptane:2% ethyl acetate. The appropriate fractions were collected and evaporated. A 2 g-portion of the residue (23.4 g) was chromatographed, eluting with hexane:dichloromethane/2:1 give 1.3 g (64.0%) of product, mp 46.5°–47.5° C.

Analysis: Calculated for $C_{20}H_{23}NO$: 81.87%C 7.90%H 4.77%N Found: 81.51%C 7.94%H 4.82%N

EXAMPLE 215

1-(4-Methylphenylsulfonyl)-5-(1-dodecynyl)indole-3-carboxaldehyde

To a degassed mixture of 1-(4-methylphenylsulfonyl)-5-bromoindole-3-carboxaldehyde (36.9 g), 1-decyne (16.8 g), in dry triethylamine (200 ml) and dry tetrahydrofuran (150 ml) was added, 1 mole percent of copper (II) iodide and 2 mole percent of bis(triphenylphosphine)palladium (II) chloride. The reaction mixture was stirred at 65° C. for 7 days. The solution was evaporated, and the residue was flash chromatographed (silica gel:4:1, dichloromethane:heptane). The appropriate fractions were collected and evaporated. The residue was recrystallized from hexane to give 23.1 g (50.8%) of product, mp 84°–86° C.

Analysis: Calculated for $C_{26}H_{29}NO_3S$: 71.69%C 6.71%H 3.22%N Found: 71.69%C 6.75%H 3.21%N

EXAMPLE 216

5-(1-Decynyl)benzo[b]thiophene

To a solution of 5-bromobenzothiophene (50.0 g), 1-decyne (35.7 g), triethylamine (71.2 g) and dry tetrahydrofuran (150 ml), under nitrogen, was added bis(triphenylphosphine)palladium (II) chloride (1.65 g) followed by copper (I) iodide (0.233 g) with stirring, at room temperature. The reaction mixture was covered with foil and stirred at reflux, under nitrogen, over the weekend. Additional bis-triphenylphosphine)palladium (II) chloride (0.5%) and 0.25% copper (I) iodide were added, and the reaction mixture was stirred at reflux for three days, cooled, filtered through a bed of celite and the filter cake was washed with ether. The residue was flash chromatographed (silica, 1% ethyl acetate-heptane). The appropriate fractions were collected and evaporated to give 56.3 g (89%) of product.

EXAMPLE 217

5-Bromoindole-3-carboxaldehyde

To a solution of phosphorous oxychloride (26.1 g) and dry dimethylformamide (50.9 ml), cooled to −10° C., was added 5-bromoindole (30 g) in portions. The reaction mixture was stirred at 10° C. for 1 hr. and at 35° C. for 1 hr. Ice (100 g) was added to the reaction mixture, followed by sodium hydroxide solution (50 ml). The mixture was heated on a steam bath for one-half hour. The precipitate was collected and recrystallized from ethanol to give 35.5 g (97.7%) of product.

EXAMPLE 218

5-Bromo-1-(4-methyphenylsulfonyl)indole-3-carboxaldehyde

To a solution of 5-bromoindole-3-carboxaldehyde (10 g) in dry tetrahydrofuran (75 ml), cooled to −78° C., was added with 2M lithium diisopropylamide/tetrahydrofuran (22.5 ml). After 30 min., the mixture was treated with a solution of tosyl chloride (9.5 g) in dry tetrahydrofuran (75 ml). The mixture was allowed to warm to room temperature overnight and evaporated. Tile residue was dissolved in dimethylformamide, filtered, and the filtrate was diluted with water. The precipitate was collected and recrystallized from ethanol to give 42 g (25%) of product.

EXAMPLE 219

1-(7-Bromo)naphthoyl-N,N-diethylcarbamate

To a solution of 7-bromo-1-naphthol (35.0 g) in dry pyridine (60 ml) was added N,N-diethylcarbamylchloride (25.6 ml) in one portion. The solution was warmed to 80° C. overnight. The reaction mixture was allowed to cool to room temperature and poured over ice water. The mixture was extracted with ethyl acetate, and the organic phase was washed with 5% hydrochloric acid and water. The organic phase was separated, dried over anhydrous magnesium sulfate, filtered, and the filtrate concentrated in vacuo. The residue was flash chromatographed over silica gel (eluted with ethyl acetate:hexane/1:5). The appropriate fractions were collected and concentrated. The residue was crystallized from diethyl ether:hexane/1:10 to afford 15.5 g (31%) of product, mp 74°–76° C.

Analysis: Calculated for $C_{15}H_{16}BrNO_2$: 55.92%C 5.01%H 4.35%N Found: 55.60%C 5.04%H 4.21%N

EXAMPLE 220 erythro-2-Amino-1-[3-(1-Undecyloxy)phenyl]-1,3-propanediol maleate erythro-2-Amino-1-[3-(1-undecyloxy)phenyl]-1,3-propanediol hydrochloride (2.15 g) was neutralized in 10% aqueous sodium hydroxide, and the mixture was extracted with ethyl acetate. The organic phase was separated, dried over anhydrous magnesium sulfate, filtered, and the filtrate was concentrated in vacuo. The residue was dissolved in ethyl acetate (15 ml) and treated with 1 eq of maleic acid. The solution was concentrated, and the residue was recrystallized from ethyl acetate to afford 0.85 g (33%) of product, mp 120°–122° C.

Analysis: Calculated for $C_{24}H_{39}NO_7$: 63.55%C 8.67%H 3.09%N Found: 63.71%C 8.65%H 3.01%N

EXAMPLE 221 erythro-1-[3-(2-Amino-1,3-dihydroxy-1-propanyl)-2-fluoro-1-phenyl]-1-dodecanon hydrochloride To a solution of erythro-2-amino-1-[3-(1-dodecynyl)-2-fluoro-1-phenyl]-1,3-propanediol (7.56 g) dissolved in tetrahydrofuran (120 ml) was added mercuric(II)oxide (2.3 g) and 3M sulfuric acid (72 ml). The reaction mixture was stirred for six days, ethyl acetate was added, and the mixture was basified with 10% sodium hydroxide solution. The mixture was extracted with ethyl acetate, and the extracts were washed with sodium chloride solution, dried over anhydrous magnesium sulfate, filtered, and the filtrate was evaporated. The residue was fractionally recrystallized to give 2.4 g (30%) of product free base. A portion was recrystallized from ethyl acetate: 10% ethanol with 1 eq. of hydrochloric acid to give product, mp 135°–137° C.

Analysis: Calculated for $C_{21}H_{35}ClFNO_3$: 62.44%C 8.73%H 3.47%N Found: 62.51%C 8.78%H 3.41%N

EXAMPLE 222 erythro-1-[3-(2-Amino-1,3-dihydroxy-1-propanyl-2-fluoro-1-phenyl]-1-dodecanone maleate To a solution of erythro-2-amino-1-[3-(1-dodecynyl)-2-fluoro-1-phenyl]-1,3-propanediol (7.56 g) dissolved in tetrahydrofuran (120 ml) was added mercuric(II)oxide (2.3 g) and 3M sulfuric acid (72 ml). The reaction mixture was stirred for six days, ethyl acetate was added, and the mixture was basified with 10% sodium hydroxide solution. The reaction mixture was extracted with ethyl acetate, and the extracts were washed with sodium chloride solution, dried over anhydrous magnesium sulfate, filtered, and the filtrate was evaporated. The residue was fractionally recrystallized to give 2.4 g (30%) of product free base. A portion was recrystallized from ethyl acetate: 1% ethanol with 1 eq. of maleic acid to give product, mp 114°–116° C.

Analysis: Calculated for $C_{25}H_{38}FNO_7$: 62.09%C 7.92%H 2.90%N Found: 62.14%C 8.07%H 2.85%N

EXAMPLE 223 erythro-1-[5-(2-Amino-1,3-dihydroxy-1-propanyl)-2-thienyl]-1-dodecanone

To a solution of erythro-2-amino-1-[5-(1-dodecynyl)-2-thienyl]-1,3-propanediol (10.1 g) dissolved in tetrahydrofuran (150 ml), was added mercuric(II)oxide (3.3 g) and 3M sulfuric acid (100 ml). The reaction mixture was stirred overnight, ethyl acetate was added, and the mixture was basified with 10% sodium hydroxide solution. The reaction mixture was extracted with ethyl acetate, and the extracts were washed with sodium chloride solution, dried over anhydrous magnesium sulfate, filtered, and the filtrate was evaporated. The residue was chromatographed on silica gel, eluting with chloroform:methanol:2N ammonium hydroxide/950:50:3. The appropriate fractions were collected and evaporated. The residue was dried to give 5.5 g (51%) of product, mp 121°–125° C.

Analysis: Calculated for $C_{19}H_{33}NO_{3}S$: 64.19%C 9.36%H 3.94%N Found: 64.33%C 9.58%H 3.86%N

EXAMPLE 224 erythro-1-[5-(2-Amino-1,3-dihydroxy-1-propanyl)-2-thienyl]-1-dodecanone maleate

To a solution of erythro-2-amino-1-[5-(1-dodecynyl)-2-thienyl]-1,3-propanediol (10.1 g) dissolved in tetrahydrofuran (150 ml) was added mercuric(II)oxide (3.3 g) and 3M sulfuric acid (100 ml). The reaction mixture was stirred overnight, ethyl acetate was added, and the mixture was basified with 10% sodium hydroxide solution. The reaction mixture was extracted with ethyl acetate, and the extracts were washed with sodium chloride solution, dried over anhydrous magnesium sulfate, filtered, and the filtrate was evaporated. The residue was chromatographed on silica gel, eluting with chloroform:methanol:2N ammonium hydroxide/950:50:3. The appropriate fractions were collected and evaporated. The residue was recrystallized with 1 eq. of maleic acid from ethyl acetate to give 2.6 g (51%) of product, mp 133°–135° C.

Analysis: Calculated for $C_{23}H_{37}NO_{7}S$: 58.58%C 7.91%H 2.97%N Found: 58.78%C 7.95%H 3.00%N

EXAMPLE 225 erythro-1-[5-(2-Amino-1,3-dihydroxy-1-propanyl)-2-thienyl]-1-dodecanone hydrochloride To a solution of erythro-2-amino-1-[5-(1-dodecynyl)-2-thienyl]-1,3-propanediol (10.1 g) dissolved in tetrahydrofuran (150 ml) was added mercuric(II)oxide (3.3 g) and 3M sulfuric acid (100 ml). The reaction mixture was stirred overnight, ethyl acetate was added, and the mixture was basified with 10% sodium hydroxide solution. The reaction mixture was extracted with ethyl acetate, and the extracts were washed with sodium chloride solution, dried over anhydrous magnesium sulfate, filtered and the filtrate was evaporated. The residue was chromatographed on silica gel, eluting with chloroform:methanol:2N ammonium hydroxide/950:50:3. The appropriate fractions were collected and evaporated. The residue was dried and recrystallized with 1 eq. of hydrochloric acid from ethyl acetate to give 1.8 g (47%) of product, mp 140°–143° C.

Analysis: Calculated for $C_{19}H_{34}ClNO_{3}S$: 58.22%C 8.74%H 3.57%N Found: 58.38%C 9.06%H 3.58%N

EXAMPLE 226 erythro-1-[5-(2-Ethylamino-1,3-dihydroxy-1-propanyl)-2-thienyl]-dodecanone hydrochloride To a solution of erythro-1-[5-(1-dodecynyl)-2-thienyl]-2-ethylamino-1,3-propanediol (4.75 g) dissolved in tetrahydrofuran (60 ml) was added mercuric(II)oxide (1.4 g), and 3M sulfuric acid (43 ml). The reaction mixture stirred overnight, ethyl acetate was added, and the mixture was basified with 10% sodium hydroxide solution. The reaction mixture was extracted with ethyl acetate, and the extracts were washed with sodium chloride solution, dried over anhydrous magnesium sulfate, filtered and the filtrate was evaporated. The residue was chromatographed on silica gel, eluting with chloroform:methanol:2N ammonium hydroxide/950:50:3. The appropriate fractions were collected and evaporated. The residue was dried and recrystallized from ethyl acetate:4% ethanol with 1 eq. of hydrochloric acid to give 1.4 g (42%) of product, mp 103°–105° C.

Analysis: Calculated for $C_{21}H_{38}ClNO_{3}S$: 60.05%C 9.12%H 3.33%N Found: 60.41%C 9.50%H 3.29%N

EXAMPLE 227 erythro-1-[5-(2-Ethylamino-1,3-dihydroxy-1-propanyl)-2-thienyl]-1-dodecanoe maleate To a solution of erythro-1-[5-(1-dodecynyl)-2-thienyl]-2-ethylamino-1,3-propanediol (4.75 g), dissolved in tetrahydrofuran (60 ml), was added mercuric(II)oxide (1.4 g) and 3M sulfuric acid (43 ml). The reaction mixture was stirred overnight, ethyl acetate was added, and the mixture was basified with 10% sodium hydroxide solution. The reaction mixture was extracted with ethyl acetate, and the extracts were washed with sodium chloride solution, dried over anhydrous magnesium sulfate, filtered, and the filtrate was evaporated. The residue was chromatographed on silica gel, eluting with chloroform:methanol:2N ammonium hydroxide/950:50:3. The appropriate fractions were collected and evaporated and dried to give 2.7 g of product free base. A portion (1.06 g) of product free base was recrystallized from ethyl acetate:2% ethanol with 1 eq. of maleic acid to give 1.1 g (44.5%) of product, mp 128°–130° C.

Analysis: Calculated for $C_{25}H_{41}NO_{7}S$: 60.10%C 8.27%H 2.80%N Found: 60.39%C 8.52%H 2.77%N

EXAMPLE 228

(2S,3R)-2-Amino-3-[7-(1-decynyl)-1-hydroxy-2-n  hthalenyl]-3-methoxy- 1-propanol maleate To a solution of 1-(7-bromo)naphthoyl-N,N-c  ylcarbamate (28 g) and tetrahydrofuran (100 ml) wa added of 1-decyne (15.6 g), followed by bistriphenylphos ne palladium(II) chloride (1.2 g), copper(I) iodide (16.5 mg), and triethylamine (61 ml). The solution was warmed to 50° C. and stirred for 2 hrs. The slurry was filtered, the filtercake was washed with ethyl acetate, and the filtrate was washed with water, followed by brine. The organic phase was separate, dried over anhydrous magnesium sulfate, filtered, and the filtrate was concentrated. The residue was flash chromatographed over silica gel (eluted with ethyl acetate-:heptane/1:8). The appropriate fractions were collected and evaporated to afford 31.5 g (95%) of 1-[7-(1-decynyl)naphthoyl]-N,N-diethylcarbamate.

To a solution of 1-[7-(1-decynyl)naphthoyl]-N,N-diethylcarbamate (7.58 g) and tetraethylenediamine (3.3 ml) in tetrahydrofuran (50 ml) at −78° C. was slowly added s-butyllithium (1.3M in cyclohexane) (17 ml) over 15 mins. The solution was stirred for ten mins and a solution of 1,1-dimethylethyl (S)-4-formyl-2,2-dimethyl-3-oxazolidinecarboxylate (5.0 g) in tetrahydrofuran (20 ml) was added. The solution was stirred for 20 mins at −78° C., quenched with water, and extracted with ethyl acetate. The organic phase was separated, dried over anhydrous magnesium sulfate, filtered, and the filtrate was concentrated. The residue was flashed chromatographed over silica gel (eluted with ethyl acetate:heptane/1:4). The appropriate fractions were collected and evaporated to give 6.57 g (54%) of mixture of erythro- and threo aldols. An identical reaction was carried out to afford and additional 5.43 g of this product.

To a solution of the aldols (11.5 g) in methanol (100 ml) at room temperature was added 3.6 g of p-toluenesulfonic acid. The mixture was stirred at room temperature for 1 hr, whereupon an additional equivalent of p-toluenesulfuric acid was added. The solution was stirred overnight, the mixture was diluted with ethyl acetate, and the solution was washed with water and brine. The organic phase was separated, dried over anhydrous magnesium sulfate, filtered, and the filtrate was concentrated. The residue was flash chromatographed over silica gel (eluted with chloroform:methanol/8:1). The appropriate fractions were collected and evaporated to afford 2.3 g of an aminodiolcarbamate as a single diastereomer and 4.3 g of an aminodiolcarbamate as a mixture of diastereomers. A second reaction afforded 1.92 g of pure amino diol carbamate.

To a solution of the aminodiolcarbamates (2.31 g) in methanol (40 ml) at room temperature was added potassium hydroxide (1.37 g). The solution was warmed to 50° C. and stirred for 30 mins. The solution was allowed to cool to room temperature, diluted with ethyl acetate and washed with 5% hydrochloric acid, followed by saturated sodium bicarbonate and brine. The organic phase was separated, dried over anhydrous magnesium sulfate, filtered, and the filtrate was concentrated. The residue was flash chromatographed over silica gel (eluted with chloroform:methanol/8:1). The appropriate fractions were collected and concentrated to afford 722 mg of the product free base. A second reaction afforded 510 mg of additional product.

To a solution of product free base (1.2 g) in ethyl acetate (10 ml) was added maleic acid (363 mg). The solution was concentrated in vacuo, and the residue recrystallized twice from ethyl acetate to afford 1.32 g (11% overall) of product, mp 134°–135° C., $[\alpha]p^{23}=+58.7°$ (c.0.64, ethanol.

Analysis: Calculated for $C_{28}H_{37}NO_7$: 67.32%C 7.46%H 2.80%N Found: 67.37%C 7.61%H 2.76%N

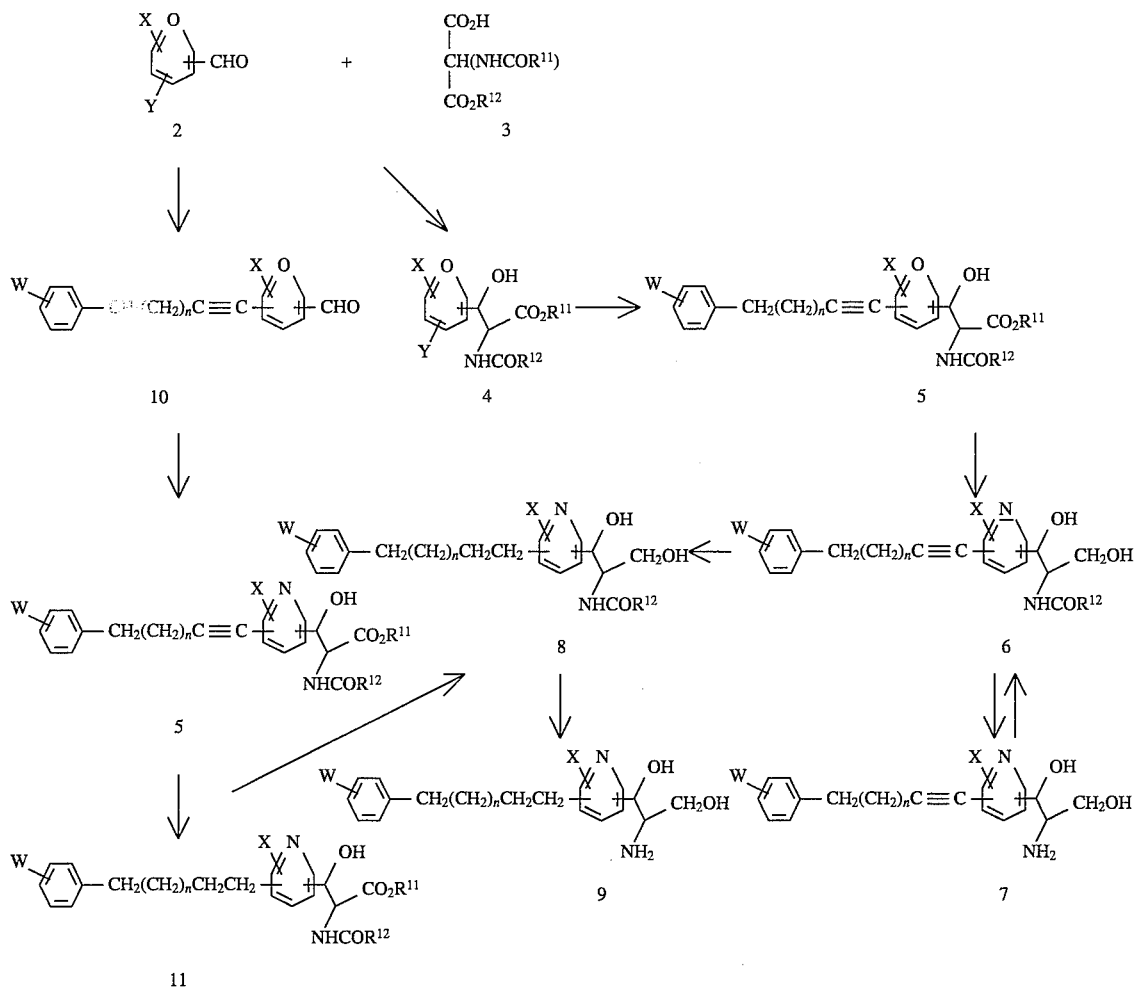

REACTION SCHEME A wherein $R^{11}$, $R^{12}$, X, W, Y, and n are as hereinbeforedescribed

REACTION SCHEME B
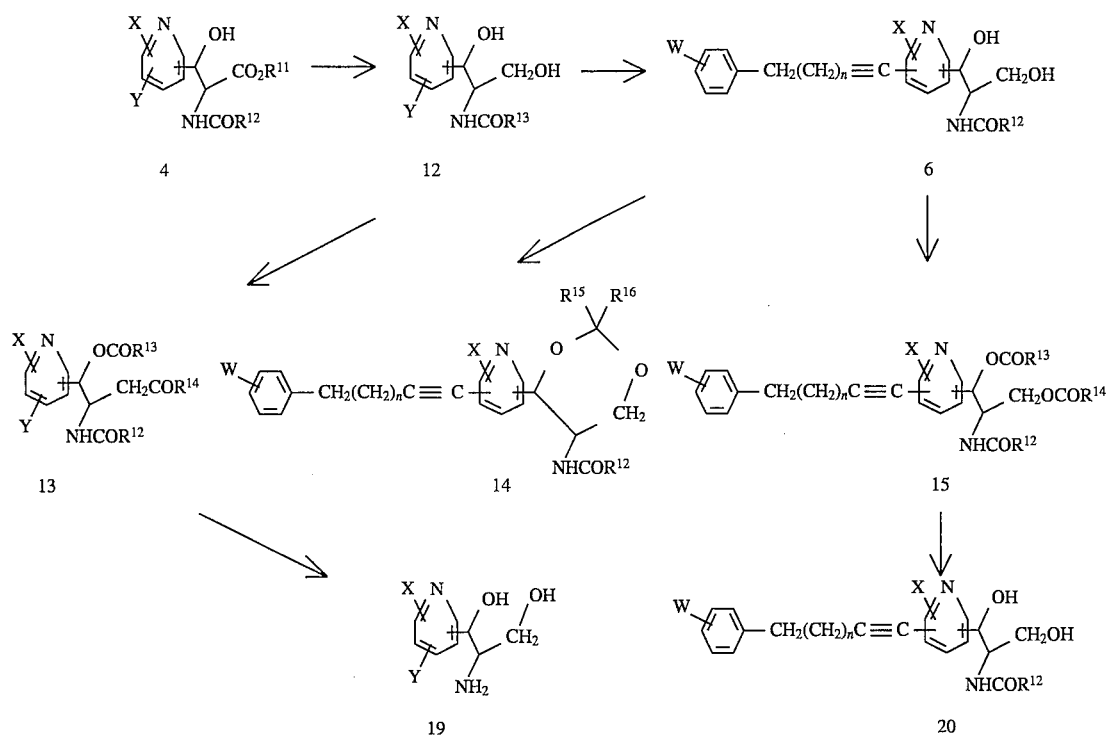
wherein $R^{11}$, $R^{12}$, $R^{13}$, $R^{14}$, X, Y, W, and n are as hereinbeforedescribed
REACTION SCHEME C
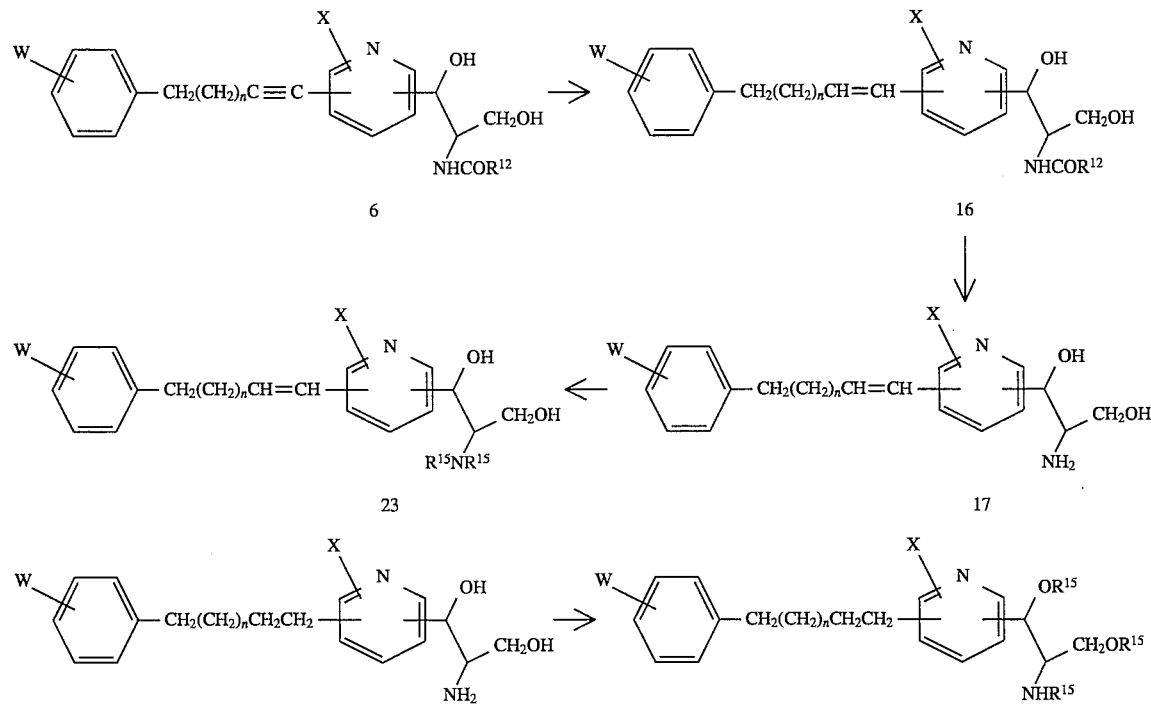
wherein W, X, $R^{12}$, $R^{15}$, and n are as hereinbeforedescribed

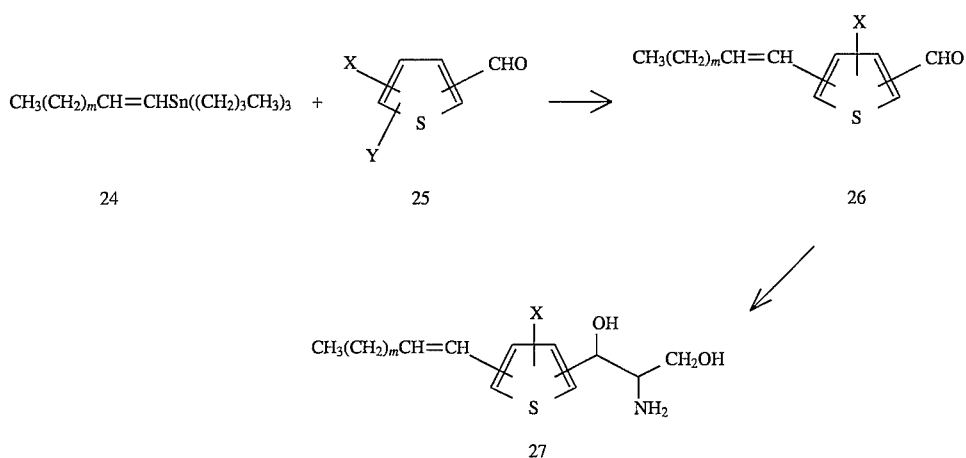
wherein X, Y, and m are as hereinbeforedescribed
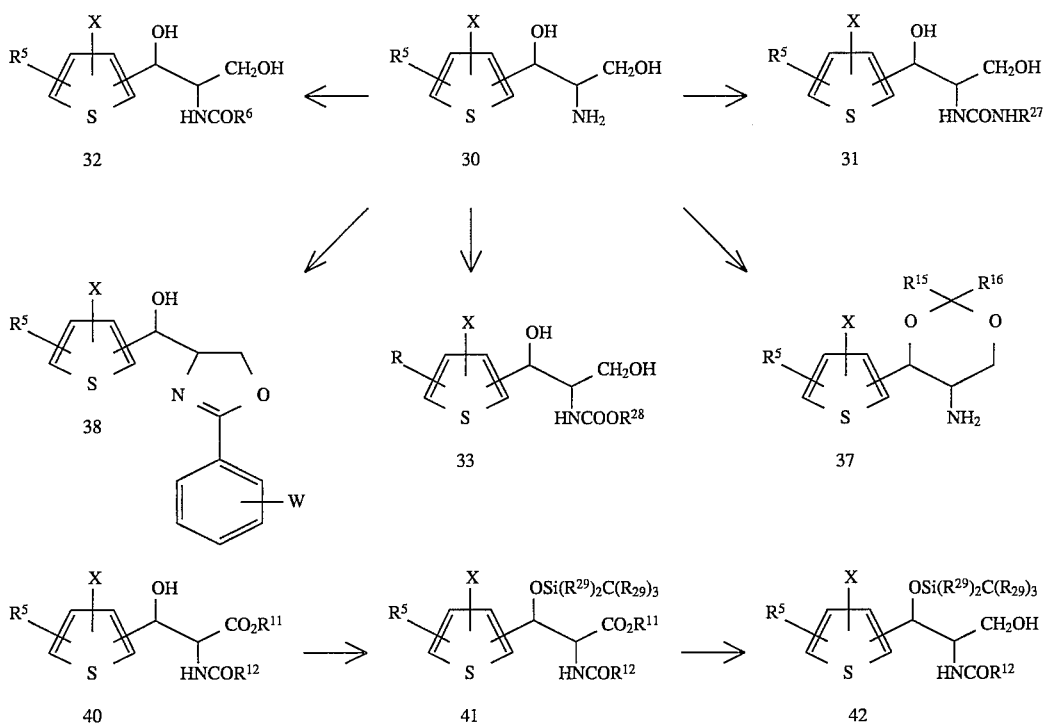
Wherein $R^5$, $R^6$, $R^{11}$, $R^{12}$, $R^{27}$, $R^{28}$, and X are as hereinbeforedescribed REACTION SCHEME F
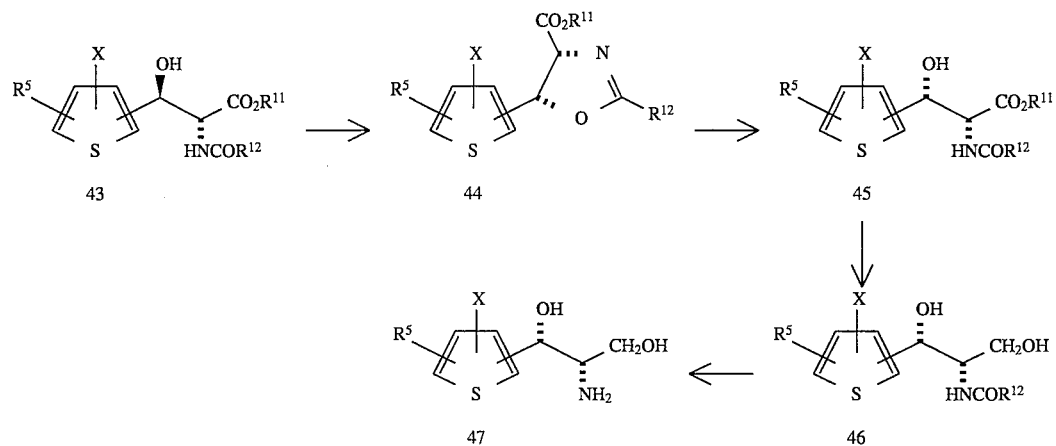
Wherein $R^5$, $R^{11}$, $R^{12}$, and X are as hereinbeforedescribed
REACTION SCHEME G
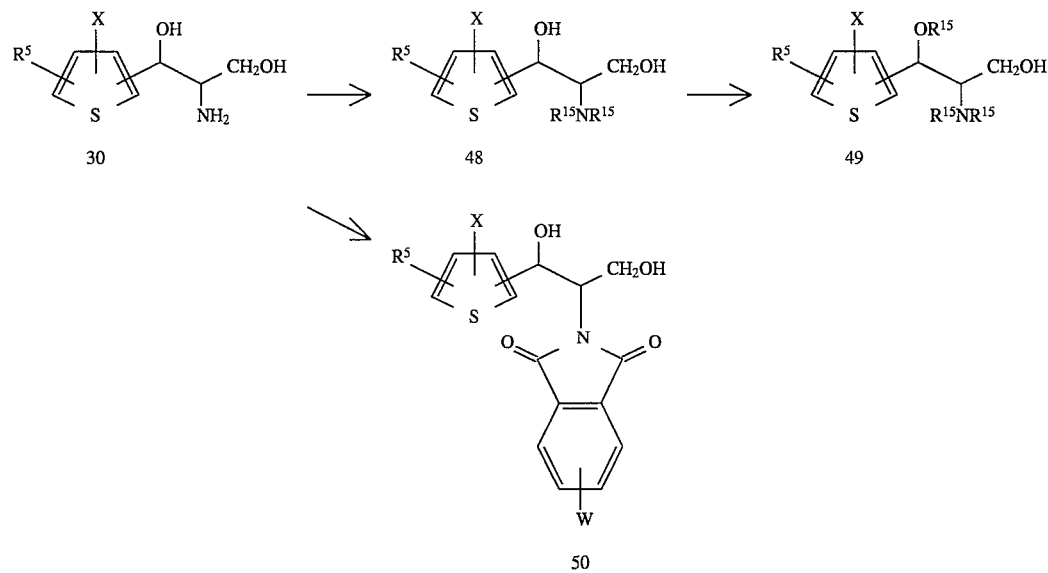
wherein $R^5$, $R^{15}$, X, and W are as hereinbeforedescribed

REACTION SCHEME H
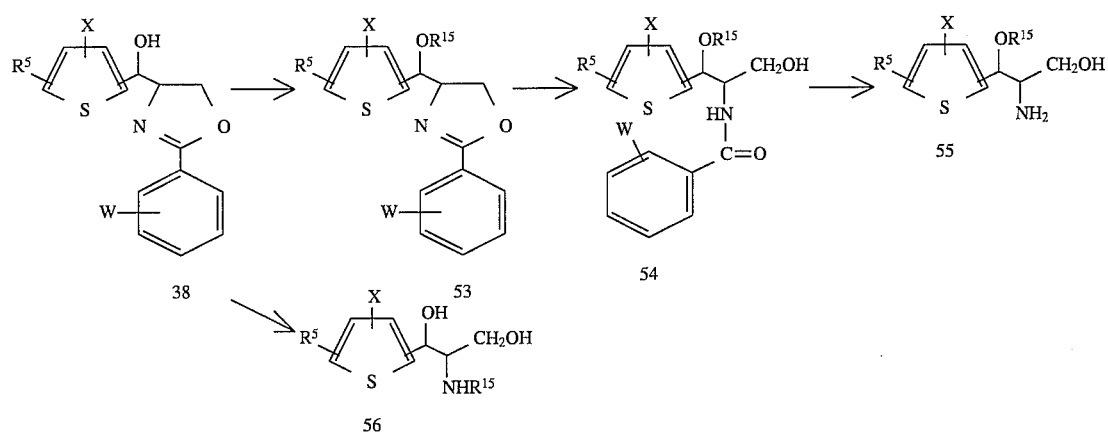
Wherein $R^5$, $R^{15}$, and X are as hereinbeforedescribed
REACTION SCHEME I
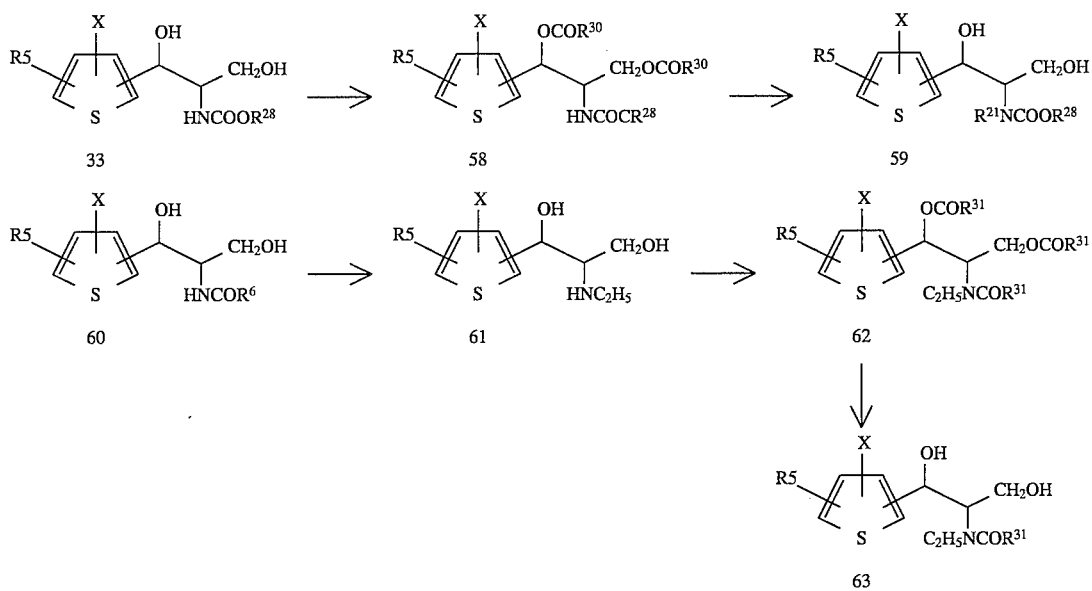
Wherein $R^5$, $R^6$, $R^{28}$, $R^{30}$, and X are as hereinbeforedescribed
REACTION SCHEME J
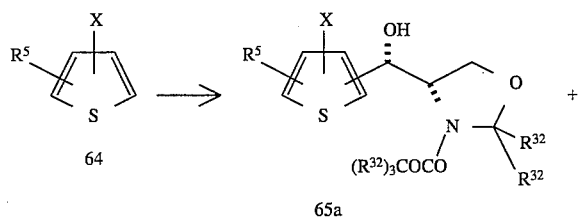

-continued
REACTION SCHEME J
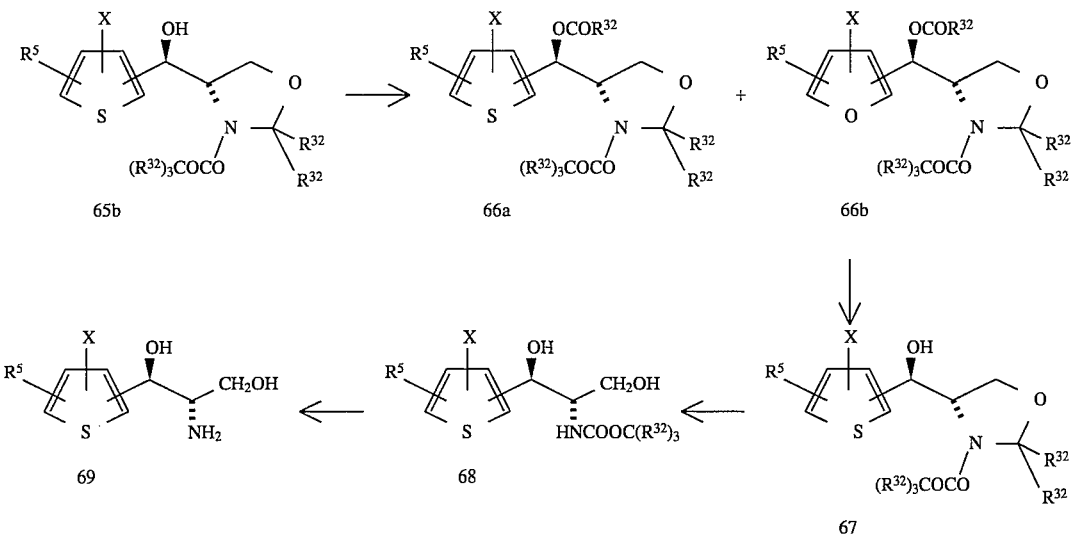
Wherein $R^5$, $R^{32}$, and X are as hereinbeforedescribed
REACTION SCHEME K
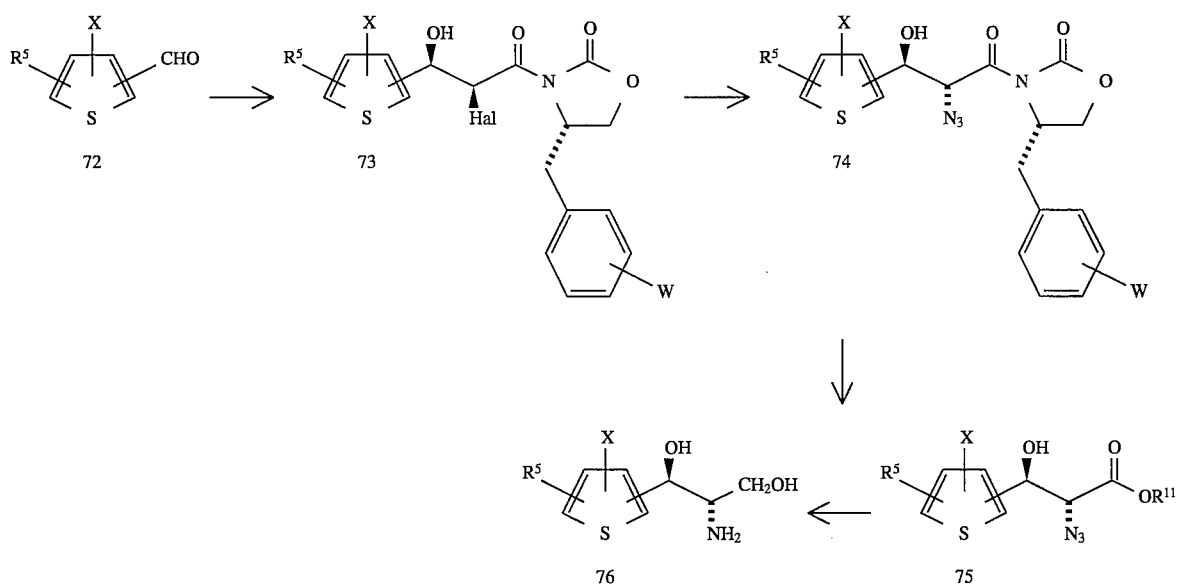
Wherein $R^5$, $R^{11}$, Hal, W, and X are as hereinbeforedescribed

REACTION SCHEME L
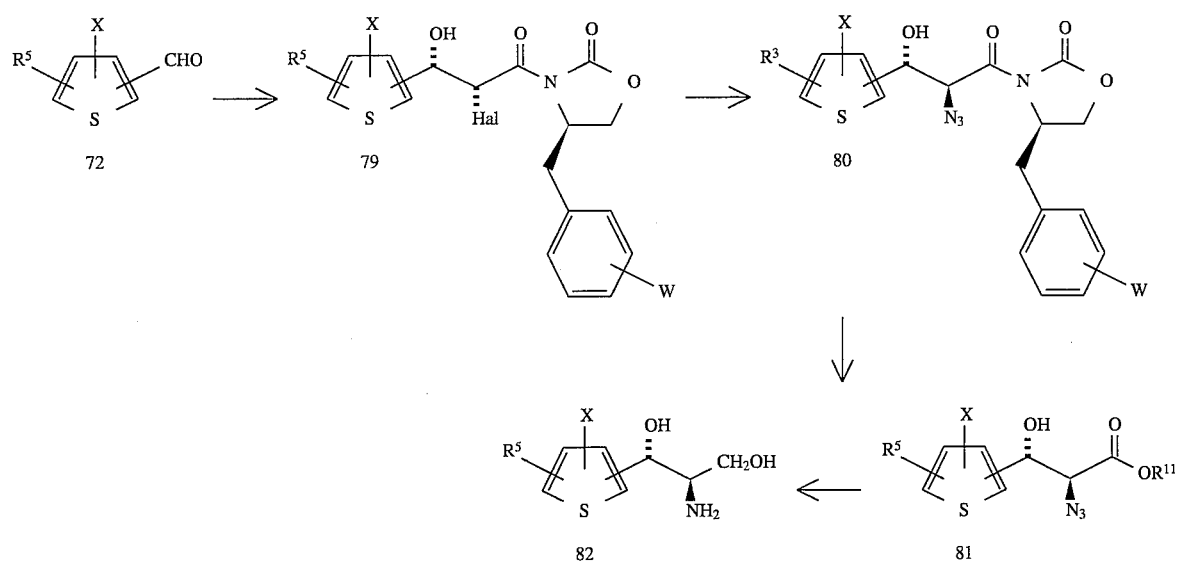
Wherein $R^5$, $R^{11}$, Hal, W, and X are as hereinbeforedescribed
REACTION SCHEME M
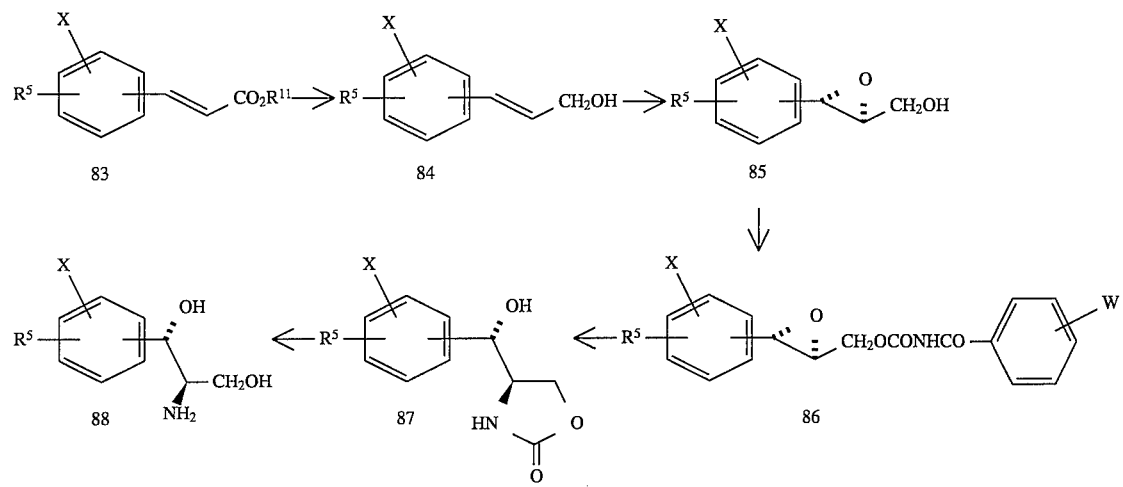
Wherein $R^5$, $R^{11}$, X, and W are as hereinbeforedefined
REACTION SCHEME N
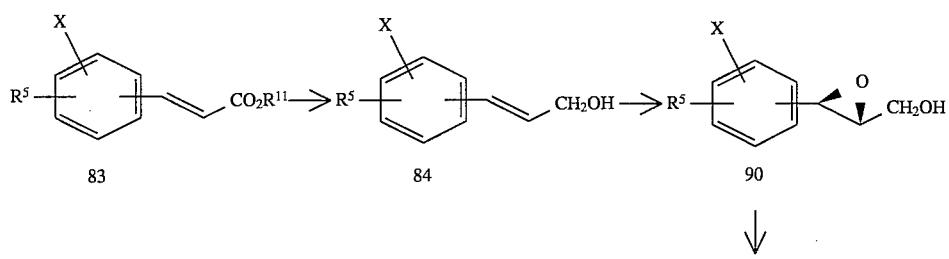

-continued
REACTION SCHEME N
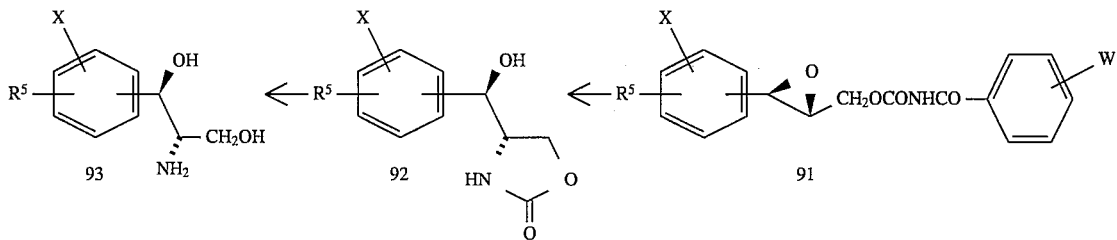
Wherein $R^5$, $R^{11}$, X, and W are as hereinbeforedefined
REACTION SCHEME O
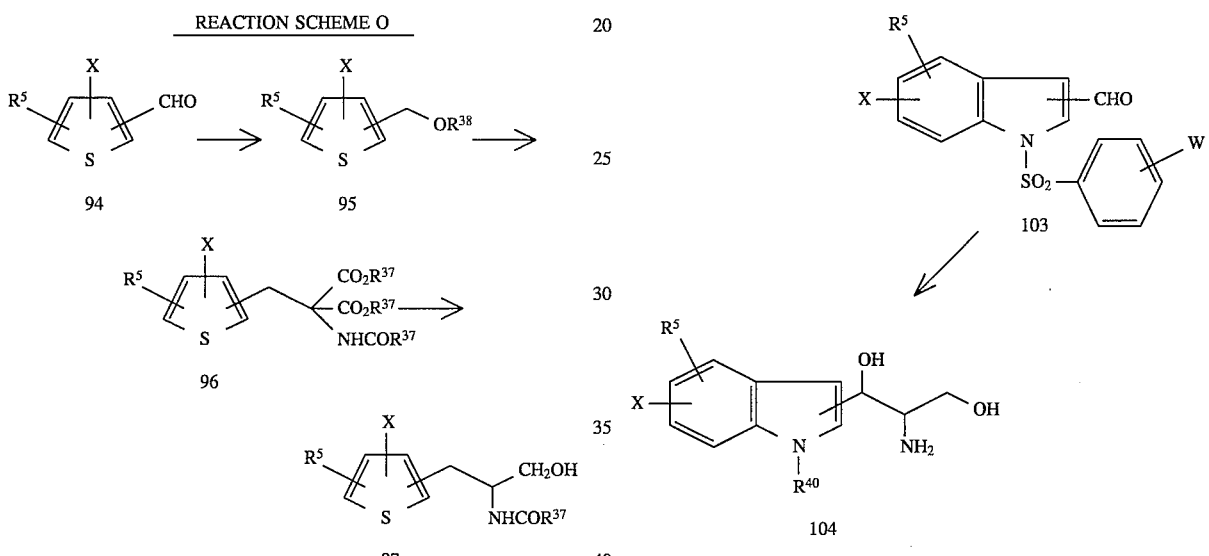
Wherein $R^5$, $R^{37}$, $R^{38}$, and X are as hereinbeforedescribed
REACTION SCHEME P
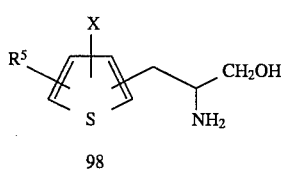
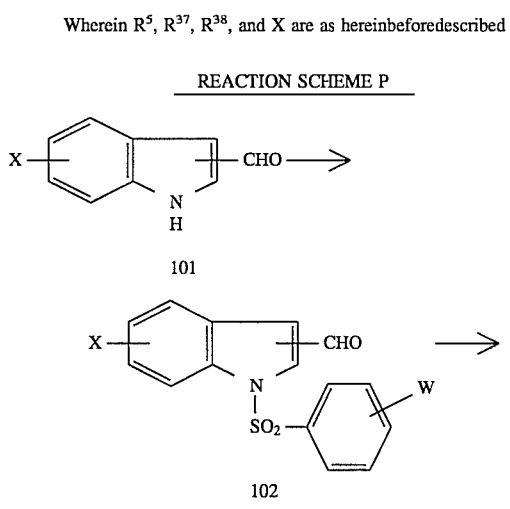
-continued
REACTION SCHEME P
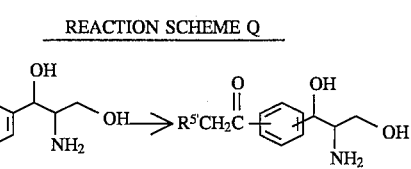
Wherein $R^5$, $R^{40}$, and X are as hereinbeforedescribed
REACTION SCHEME Q

123
-continued
REACTION SCHEME Q

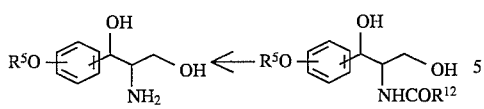

Wherein $R^5$, $R^{5'}$, $R^{11}$, and $R^{12}$ are as hereinbeforedescribed

We claim:

1. A compound of the formula

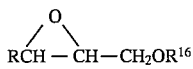

wherein R is

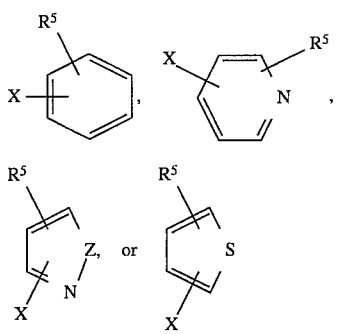

wherein $R^5$ is $CH_3(CH_2)_mC\equiv C$, $CH_3(CH_2)_mCH=CH$, $CH_3(CH_2)_mCH_2CH_2$, or

124 wherein m is 3 to 15, n is 0 to 12, $R^{16}$ is hydrogen or

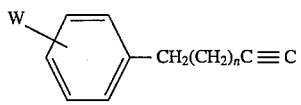

W and X are a group of the formula

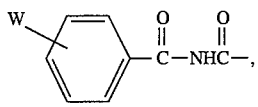

independently hydrogen, loweralkyl, loweralkoxy, halogen, or trifluoromethyl, and Z is O, with the proviso that R is

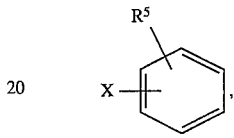

$R^5$ is not $CH_3(CH_2)_mCH_2CH_2$.

2. The compound of claim 1 which is (2S-trans)-3-[3-(1-dodecynyl)phenyl]oxiranemethanol.

3. The compound of claim 1 which is (2R-trans)-3-[3-(1-dodecynyl)phenyl]oxiranemethanol.

4. The compound of claim 1 which is (2S-trans)-3-[3-(1-dododecynyl)phenyl]epoxypropyl benzoyl carbamate.

5. The compound of claim 1 which is (2R-trans)-3-[3-(1-dodecynyl)phenyl)epoxypropyl benzoyl carbamate.

* * * * *